United States Patent [19]

Young et al.

[11] Patent Number: 5,472,964
[45] Date of Patent: Dec. 5, 1995

[54] DIARYL 5,6-FUSED HETEROCYCLIC ACIDS AS LEUKOTRIENE ANTAGONISTS

[75] Inventors: Robert N. Young, Senneville; Marc Labelle, lle Perrot; Yves Leblanc, Kirkland, all of Canada; Yi B. Xiang, Acton, Mass.; Cheuk K. Lau, lle Bizard, Canada; Claude Dufresne, Dollard Des Ormeaux, Canada; Yves Gareau, N.D. lle-Perrot, Canada

[73] Assignee: Merck Frosst Canada, Inc., Kirkland, Canada

[21] Appl. No.: 260,592

[22] Filed: Jun. 16, 1994

Related U.S. Application Data

[63] Continuation-in-part of Ser. No. 174,937, Dec. 28, 1993, abandoned, which is a continuation-in-part of Ser. No. 994,869, Dec. 22, 1992, abandoned.

[51] Int. Cl.$^6$ ............ A61K 31/435; C07D 495/04; C07D 513/04; C07D 491/048
[52] U.S. Cl. ............ 514/243; 514/249; 514/258; 514/301; 514/302; 544/184; 544/255; 544/278; 544/350; 546/114; 546/115; 546/116
[58] Field of Search ............ 544/184, 255, 544/278, 350; 546/114, 115, 116; 514/243, 249, 258, 301, 302

[56] References Cited

U.S. PATENT DOCUMENTS 4,794,188 12/1988 Musser et al. ............ 546/152
4,957,932 9/1990 Young et al. ............ 514/375

FOREIGN PATENT DOCUMENTS

| | | |
|---|---|---|
| 0318084 | 5/1989 | European Pat. Off. . |
| 0367235 | 5/1990 | European Pat. Off. . |
| 0480716 | 4/1992 | European Pat. Off. . |
| 0480717 | 4/1992 | European Pat. Off. . |
| 0535925 | 4/1993 | European Pat. Off. . |

*Primary Examiner*—Bernard Dentz
*Attorney, Agent, or Firm*—Mollie M. Yang; David L. Rose

[57] ABSTRACT

Compounds having the formula I:

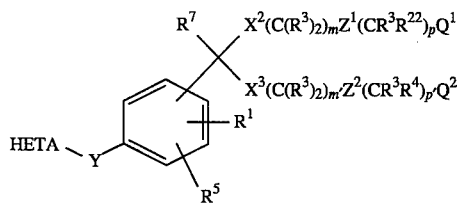

are antagonists of the actions of leukotrienes. These compounds are useful as anti-asthmatic, anti-allergic, anti-inflammatory, and cytoprotective agents. They are also useful in treating angina, cerebral spasm, glomerular nephritis, hepatitis, endotoxemia, uveitis, and allograft rejection.

17 Claims, No Drawings

DIARYL 5,6-FUSED HETEROCYCLIC ACIDS AS LEUKOTRIENE ANTAGONISTS

CROSS REFERENCE TO RELATED APPLICATION

This application is a continuation-in-part of co-pending application Ser. No. 174,937 filed Dec. 28, 1993, now abandoned, which is a continuation-in-part of Ser. No. 994,869 filed Dec. 22, 1992, now abandoned; the aforementioned applications are hereby incorporated in their entirety.

BACKGROUND OF THE INVENTION

The leukotrienes constitute a group of locally acting hormones, produced in living systems from arachidonic acid. The is major leukotrienes are Leukotriene $B_4$ (abbreviated as $LTB_4$), $LTC_4$, $LTD_4$, and $LTE_4$. The biosynthesis of these leukotrienes begins with the action of the enzyme 5-lipoxygenase on arachidonic acid to produce the epoxide known as Leukotriene $A_4$ ($LTA_4$), which is convened to the other leukotrienes by subsequent enzymatic steps. Further details of the biosynthesis as well as the metabolism of the leukotrienes are to be found in the book *Leukotrienes and Lipoxygenases*, ed. J. Rokach, Elsevier, Amsterdam (1989). The actions of the leukotrienes in living systems and their contribution to various diseases states are also discussed in the book by Rokach.

U.S. Pat. No. 4,957,932, Young et al., discloses compounds of Formula 1 as leukotriene antagonists and inhibitors of leukotriene biosynthesis. The present compounds differ from Young's primarily in having a different heterocyclic ring on the left side of the structure. Fujikawa describes the thieno[2,3-b]-pyridine 2 in EP 367,235 but the point of attachment and the nature of the principal substituent are different from the present compounds. Musser et al., describe compound 3 in U.S. Pat. No. 4,794,188 as being lipoxygenase inhibitors and possessing anti-inflammatory and anti-allergic activities. However, compound 3 differs from the present compounds principally in that $Ar_1$ is different from our HETA grouping. Thus, the compounds of the present invention are novel.

SUMMARY OF THE INVENTION

The present invention relates to 5,6-fused heterocyclic acids having activity as leukotriene antagonists, to methods for their preparation, and to methods and pharmaceutical formulations for using these compounds in mammals (especially humans).

Because of their activity as leukotriene antagonists, the compounds of the present invention are useful as anti-asthmatic, anti-allergic, anti-inflammatory, and cytoprotective agents. They are also useful in treating angina, cerebral spasm, glomerular nephritis, hepatitis, endotoxemia, uveitis, and allograft rejection.

DETAILED DESCRIPTION OF THE INVENTION

The compounds of the invention are best realized by the Formula I:

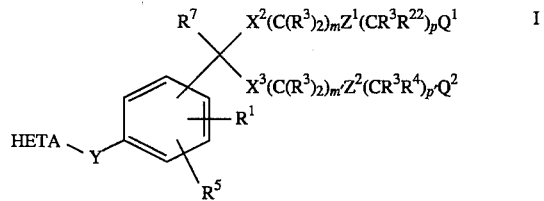

wherein:

$R^1$ is H or $R^2$;

$R^2$ is lower alkyl, lower alkenyl, lower alkynyl, $-CF_3$, $-CH_2F$, $-CHF_2$, $Ph(R^{26})_2$, $CH_2Ph(R^{26})_2$, or $CH_2CH_2Ph(R^{26})_2$ or two $R^2$ groups joined to the same atom may form a monocyclic or bicyclic ring of up to 8 members comprising carbon atoms and up to 2 heteroatoms chosen from O, S, and N;

$R^3$ is H or $R^2$;

$R^4$ is $R^3$, halogen, $-NO_2$, $-CN$, $-OR^3$, $-SR^3$, $N(R^3)_2$, $NR^3COR^7$, $S(O)R^2$, or $S(O)_2R^2$;

$CR^3R^{22}$ may be the radical of a standard amino acid;

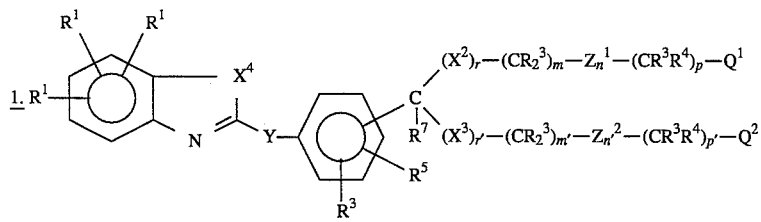

Young, et al.
U.S.P. 4,957,932

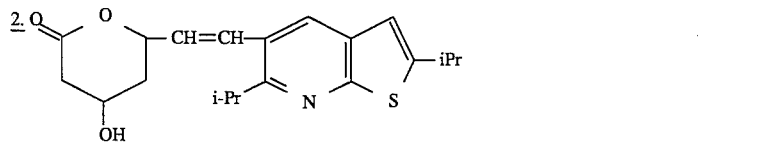

Fujikawa
EP 367,235

3. $Ar_1-X-Ar-Z-(R)_{n'}$
Musser et al.
U.S.P. 4,794,188

$R^5$ is H, halogen, $-NO_2$, $-N_3$, $-CN$, $-SR^2$, $-S(O)R^2$, $S(O)_2R^2$, $-N(R^3)_2$, $-OR^3$, $-COR^3$, or lower alkyl;

$R^6$ is $-(CH_2)_s-C(R^7)_2-(CH_2)_s-R^8$ or $-CH_2CON(R^{20})_2$;

$R^7$ is H or lower alkyl;

$R^8$ is A) a monocyclic or bicyclic heterocyclic radical containing from 3 to 12 nuclear carbon atoms and 1 or 2 nuclear heteroatoms selected from N, S, and O and with each ring in the heterocyclic radical being formed of 5 or 6 atoms, or B) the radical $W-R^9$;

$R^9$ contains up to 21 carbon atoms and is (1) a hydrocarbon radical or (2) an acyl radical of an organic acyclic or monocyclic carboxylic acid containing not more than 1 heteratom in the ring;

$R^{10}$ is H, lower alkyl, or benzyl;

$R^{11}$ is lower alkyl, $-COR^{14}$, $ph(R^{26})_2$, $CH_2Ph(R^{26})_2$, or $CH_2CH_2Ph(R^{26})_2$;

$R^{12}$ is H, $R^{11}$, or two $R^{12}$ groups joined to the same N may form a saturated ring of 5 or 6 members comprising carbon atoms and up to two heteroatoms chosen from O, S, and N;

$R^{13}$ is lower alkyl, lower alkenyl, lower alkynyl, $-CF_3$, $Ph(R^{26})_2$, $CH_2Ph(R^{26})_2$, or $CH_2CH_2Ph(R^{26})_2$;

$R^{14}$ is H or $R^{13}$;

$R^{15}$ is H, oxetanyl or $R^{11}$;

$R^{16}$ is H, lower alkyl, or OH;

$R^{17}$ is lower alkyl, lower alkenyl, lower alkynyl, $Ph(R^{26})_2$, $CH_2Ph(R^{26})_2$, or $CH_2CH_2Ph(R^{26})_2$;

$R^{18}$ is $R^{13}$;

$R^{19}$ is H, lower alkyl, lower alkenyl, lower alkynyl,— $CF_3$, Ph, $CH_2Ph$, or $CH_2CH_2Ph$;

$R^{20}$ is H, lower alkyl, $Ph(R^{26})_2$, $CH_2Ph(R^{26})_2$, or $CH_2CH_2Ph(R^{26})_2$ or two $R^{20}$ groups joined to the same N may form a saturated ring of 5 or 6 members comprising carbon atoms and up to two heteroatoms chosen from O, S, and N;

$R^{21}$ is H or $R^{17}$;

$R^{22}$ is $R^4$, $CHR^7OR^3$, or $CHR^7SR^2$;

$R^{23}$, $R^{24}$, and $R^{25}$ is each independently H, lower alkyl, $-CN$, $-CF_3$, $C(R^3)_2OH$, $COR^3$, $CO_2R^7$, $CON(R^{20})_2$, $OR^3$, $SR^2$, $S(O)_2R^2$, $S(O)_2R^2$, $N(R^{12})_2$, halogen, or an electron pair;

$R^{26}$ is H, lower alkyl, $-SR^{27}$, $-OR^{28}$, $-N(R^{28})_2$, $-CO_2R^7$, $CON(R^{28})_2$, $-COR^7$, $-CN$, $CF_3$, $NO_2$, $SCF_3$, or halogen;

$R^{27}$ is lower alkyl, phenyl, or benzyl;

$R^{28}$ is $R^{27}$, H, or $COR^7$, or two $R^{28}$ groups joined to the same N may form a saturated ting of 5 or 6 members comprising carbon atoms and up to 2 heteroatoms chosen from O, S, or N;

m and m' are independently 0–8;

p and p' are independently 0–8;

m+p is 1–10 when $X^2$ is O, S, S(O), or $S(O)_2$ and $Z^1$ is a bond;

m+p is 0–10 when $Z^1$ is $HET(R^{23}R^{24}R^{25})$;

m+p is 0–10 when $X^2$ is $CR^3R^{16}$;

m'+p' is 1–10 when $X^3$ is O, S, S(O), or $S(O)_2$ and $Z^2$ is a bond;

m'+p' is 0–10 when $Z^2$ is $HET(R^{23}R^{24}R^{25})$;

m'+p' is 0–10 when $X^3$ is $CR^3R^{16}$;

s is 0–3;

$Q^1$ is tetrazol-5-yl, $-CO_2R^3$, $-CO_2R^6$, $-CONHS(O)_2R^{13}$, $-CN$, $-CON(R^{20})_2$, $NR^{21}S(O)_2R^{13}$, $-NR^{21}CON(R^{20})_2$, $-NR^{21}COR^{14}$, $OCON(R^{20})_2$, $-COR^{19}$, $-S(O)R^{18}$, $-S(O)_2R^{18}$, $-S(O)_2N(R^{20})_2$, $-NO_2$, $NR^{21}CO_2R^{17}$, $-C(N(R^{12})_2)=NR^{21}$, $-C(R^{19})=NOH$, $P(O)(OR^{10})_2$ or $C(R^3)_2OR^3$; or if $Q^1$ is $CO_2H$ and $R^{22}$ is $-OH$, $-SH$, $CHR^7OH$ or $-NHR^3$, then $Q^1$ and $R^{22}$ and the carbons through which they are attached may form a heterocyclic ring by loss of water;

$Q^2$ is H, $OR^{15}$, lower alkyl, halogen, or $Q^1$;

W is O, S, or $NR^3$;

$X^1$ is O, S, $-S(O)-$, $-S(O)_2-$, $=NR^3$, $-C(R^3)_2-$, or a bond;

$X^2$ and $X^3$ are independently O, S, S(O), $S(O)_2$, $CR^3R^{16}$, or a bond;

Y is $-CR^3=CR^3-$, $-C(R^3)_2-X^1-$, $-X^1-C(R^3)_2-$, $-C(R^3)_2-X^1-C(R^3)_2-$, $-CH(CH_2)CH-$, $-C\equiv C-$, $-CO-$, $-NR^3CO-$, $-CONR^3-$, O, S, or $NR^3$;

$Z^1$ and $Z^2$ are independently $HET(R^{23}R^{24}R^{25})$ or a bond;

HET is the diradical of benzene, pyridine, furan, thiophene, thiazole, or 1,2,5-thiadiazole;

HETA is $HE^1$ or $HE^2$;

$HE^1$ is

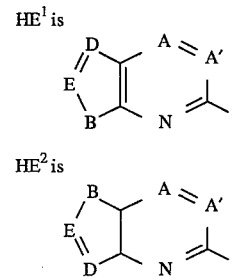

$HE^2$ is

A and $A^1$ is each independently N or $CR^5$;

B is O, S, or S(O);

D is N or $CR^4$;

E is $CR^4$ when D is $CR^4$;

E is $CR^3$ when D is N;

or a pharmaceutically acceptable salt thereof.

Preferred compounds of Formula I are those of Formula Ia:

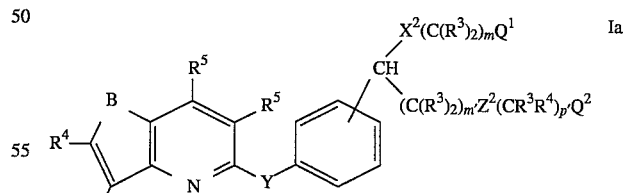

wherein:

B is S or O;

$R^4$ is H, lower alkyl, halogen, CN, $CF_3$, or $S(O)_2R^2$;

$R^5$ is H or halogen;

m and m' is each independently 1–6;

p' is 0 or 1;

$Q^1$ is $CO_2R^3$, $CO_2R^6$, $-CONHS(O)_2R^{13}$, tetrazol-5-yl or $C(R^3)_2OH$;

$Q^2$ is H, $C(R^3)_2OH$, halogen, $OR^{15}$, $CON(R^{20})_2$, $P(O)(OR^{10})_2$, $SO_2R^{18}$, $CO_2R^3$ or lower alkyl;

$X^2$ is S or O;

Y is —CH=CH—, —CH$_2$—O—, —O—CH$_2$—, CH$_2$—CH$_2$—, —C≡C—, —C(CH$_2$)$_2$— or —CH(CH$_2$)CH—;

$Z^2$ is HET ($R^{23}R^{24}$) or a bond; and

HET is a diradical of benzene, 1,2,5-thiadiazole, thiazole or thiophene; and the remaining substituents are as defined for Formula I.

A group of more preferred compounds of Formula I is described by Formula Ib:

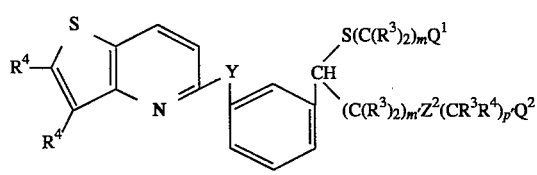

wherein:

$R^3$ is H, lower alkyl, or two $R^3$ joined to the same carbon may form a monocyclic ring from 3 to 6 members, optionally containing one oxygen or one sulfur;

$R^4$ is H, lower alkyl, halogen, —CN, $CF_3$, or —$S(O)_2R^2$;

$R^{23}$ and $R^{24}$ are independently H, halogen, lower alkyl, $SR^2$, $CF_3$, $COR^3$ or $C(R^3)_2OR^3$;

m and m' are independently 1–5;

p' is 0 or 1;

$Q^1$ is —$CO_2R^3$, tetrazol-5-yl, or —$CONHS(O)_2R^{13}$; and $Q^2$ is H, $C(R^3)_2OH$, $P(O)(OR^{10})_2$, $SO_2R^{18}$, $CO_2R^3$ or $OR^{15}$;

Y is —CH=CH—, —$CH_2O$—, or —$OCH_2$—;

$Z^2$ is HET($R^{23}R^{24}$); and

HET is a diradical of benzene, 1,2,5-thiadiazole, thiazole or thiophene; and the remaining substituents are as defined for Formula I.

A group of most preferred compounds of Formula I is described by Formula Ic:

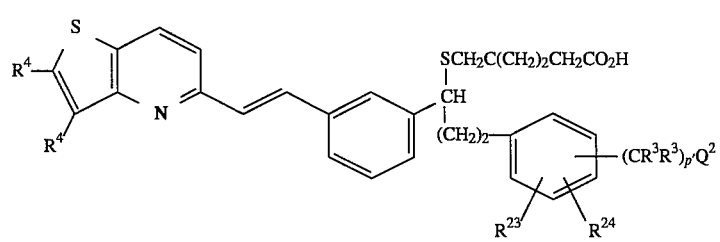

wherein:

$R^2$ is lower alkyl or phenyl;

$R^3$ is H, lower alkyl or two $R^3$ joined to the same carbon may form a monocyclic ring from 3 to 6 members, optionally containing one oxygen or one sulfur;

$R^4$ is H, halogen or —$S(O)_2R^2$;

$R^{15}$ is H, oxetanyl or lower alkyl;

$R^{18}$ is lower alkyl;

$R^{23}$ and $R^{24}$ are independently H, halogen, lower alkyl, $SR^2$, $CF_3$, $COR^3$ or $C(R^3)_2OH$;

$R^{10}$ is H, lower alkyl or benzyl;

p' is 0 or 1; and $Q^2$ is H, $C(R^3)_2OH$, $P(O)(OR^{10})_2$, $S(O)_2R^{18}$, $CO_2R^3$ or $OR^{15}$.

Definitions

The following abbreviations have the indicated meanings:

| | |
|---|---|
| Ac = | acetyl |
| Ac$_2$O = | acetic anhydride |
| AIBN = | 2,2'-azobisisobutyronitrile |
| Bn = | benzyl |
| DHP = | 2,3-dihydro-4H-pyran |
| DIBAL = | diisobutyl aluminum hydride |
| DIPHOS = | 1,2-bis(diphenylphosphino)ethane |
| DMAP = | 4-(dimethylamino)pyridine |
| DMF = | N,N-dimethylformamide |
| DMSO = | dimethyl sulfoxide |
| DX = | 6,8-dioxobicyclo[3.2.1]octan-3-yl |
| Et$_3$N = | triethylamine |
| EtOAc = | ethyl acetate |
| Fur = | furandiyl |
| KHMDS = | potassium hexamethyldisilazane |
| LDA = | lithium diisopropylamide |
| MCPBA = | metachloroperbenzoic acid |
| Ms = | methanesulfonyl = mesyl |
| MsO = | methanesulfonate = mesylate |
| NBS = | N-bromosuccinimide |
| NCS = | N-chlorosuccinimide |
| NSAID = | non-steroidal anti-inflammatory drug |
| OX = | oxetan-3-yl |
| PCC = | pyridinium chlorochromate |
| PDC = | pyridinium dichromate |
| Ph = | phenyl |
| Phe = | benzenediyl |
| PPTS = | pyridinium p-toluene sulfonate |
| pTSA = | p-toluene sulfonic acid |
| Pye = | pyridinediyl |
| r.t. = | room temperature |
| rac. = | racemic |
| Tdz = | 1,2,5-thiadiazol-3,4-diyl |
| Tf = | trifluoromethanesulfonyl = triflyl |
| TfO = | trifluoromethanesulfonate = triflate |
| Th = | 2- or 3-thienyl |
| THF = | tetrahydrofuran |
| Thi = | thiophenediyl |
| THP = | tetrahydropyran-2-yl |
| Thz = | thiazol-2-yl |
| T4P = | tetrahydropyran-4-yl |

-continued

| | |
|---|---|
| TLC = | thin layer chromatography |
| Ts = | p-toluenesulfonyl = tosyl |
| TsO = | p-toluenesulfonate = tosylate |
| Tz = | 1H (or 2H)-tetrazol-5-yl |
| C$_3$H$_5$ = | allyl |

Alkyl group abbreviations

| | |
|---|---|
| Me = | methyl |
| Et = | ethyl |
| n-Pr = | normal propyl |
| i-Pr = | isopropyl |
| n-Bu = | normal butyl |
| i-Bu = | isobutyl |
| s-Bu = | secondary butyl |
| t-Bu = | tertiary butyl |
| c-Pr = | cyclopropyl |
| c-Bu = | cyclobutyl |
| c-Pen = | cyclopentyl |
| c-Hex = | cyclohexyl |

The terms alkyl, alkenyl, and alkynyl mean linear, branched, and cyclic structures and combinations thereof.

The term "alkyl" includes "cycloalkyl" and "lower alkyl" and extends to cover carbon fragments having up to 20 carbon atoms. Examples of alkyl groups include octyl, nonyl, undecyl, dodecyl, tridecyl, tetradecyl, pentadecyl, eicosyl, 3,7-diethyl-2,2-dimethyl-4-propylnonyl, and the like.

"Lower alkyl" includes "lower cycloalkyl" and means alkyl groups of from 1 to 7 carbon atoms. Examples of lower alkyl groups include methyl, ethyl, propyl, isopropyl, butyl, s- and t-butyl, pentyl, hexyl, heptyl, and the like.

"Cycloalkyl" includes "lower cycloalkyl" and means a hydrocarbon, containing one or more rings of from 3 to 12 carbon atoms, with the hydrocarbon having up to a total of 20 carbon atoms. Examples of cycloalkyl groups are cyclopropyl, cyclopentyl, cycloheptyl, aldamantyl, cyclododecylmethyl, 2-ethyl-1-bicyclo[4.4.0]decyl, and the like.

"Lower cycloalkyl" means a hydrocarbon containing one or more rings of from 3 to 7 carbon atoms, with the hydrocarbon having up to a total of 7 carbon atoms. Examples of lower cycloalkyl groups are cyclopropyl, cyclopropylmethyl, cyclobutyl, 2-cyclopentylethyl, cycloheptyl, bicyclo[2.2.1]hept-2-yl, and the like.

The term "alkenyl" includes "cycloalkenyl" and "lower alkenyl" and means alkenyl groups of 2 to 20 carbon atoms. Examples of alkenyl groups include allyl, 5-decen-1-yl, 2-dodecen-1-yl, and the like.

"Lower alkenyl" includes "lower cycloalkenyl" and means alkenyl groups of 2 to 7 carbon atoms. Examples of lower alkenyl groups include vinyl, allyl, isopropenyl, pentenyl, hexenyl, heptenyl, 1-propenyl, 2-butenyl, 2-methyl-2-butenyl, and the like.

"Cycloalkenyl" includes "lower cycloalkenyl" and means alkenyl groups of 3 to 20 carbon atoms, which include a ring of 3 to 12 carbon atoms, and in which the alkenyl double bond may be located anywhere in the structure. Examples of cycloalkenyl groups are cyclopropen-1-yl, cyclohexen-3-yl, 2-vinyladamant-1-yl, 5-methylenedodec-1-yl, and the like.

"Lower cycloalkenyl" means alkenyl groups of 3 to 7 carbon atoms, which include a ting of 3 to 7 carbon atoms and in which the double bond may be located anywhere in the structure. Examples of lower cycloalkenyl groups are cyclopropen-1-yl, cyclohexen-3-yl, 2-cyclopentylethen-1-yl, and the like.

The term "alkynyl" includes "cycloalkynyl" and "lower alkynyl" and means alkynyl groups of 2 to 20 carbon atoms. Examples of alkynyl groups are ethynyl, 2-pentadecyn-1-yl, 1-eicosyn-1-yl, and the like.

"Lower alkynyl" includes "lower cycloalkynyl" and means alkynyl groups of 2 to 7 carbon atoms. Examples of lower alkynyl groups include ethynyl, propargyl, 3-methyl-1-pentynyl, 2-heptynyl and the like.

"Cycloalkynyl" includes "lower cycloalkynyl" and means alkynyl groups of 5 to 20 carbon atoms, which include a ring of 3 to 20 carbon atoms. The alkynyl triple bond may be located anywhere in the group, with the proviso that if it is within a ring, such a ring must be of 10 members or greater. Examples of cycloalkynyl are cyclododecyn-3-yl, 3-cyclohexyl-1-propyn-1-yl, and the like.

"Lower cycloalkynyl" means alkynyl groups of 5 to 7 carbon atoms which include a ring of 3 to 5 carbon atoms. Examples of lower cycloalkynyl are cyclopropylethynyl, 3-(cyclobutyl)-1-propynyl, and the like.

"Lower alkoxy" means alkoxy groups of from 1 to 7 carbon atoms of a straight, branched, or cyclic configuration. Examples of lower alkoxy groups include methoxy, ethoxy, propoxy, isopropoxy, cyclopropyloxy, cyclohexyloxy, and the like.

"Lower alkylthio" means alkylthio groups of from 1 to 7 carbon atoms of a straight, branched, or cyclic configuration. Examples of lower alkylthio groups include methylthio, propylthio, isopropylthio, cycloheptylthio, etc. By way of illustration, the propylthio group signifies $-SCH_2CH_2CH_3$.

"Lower alkylsulfonyl" means alkylsulfonyl groups of from 1 to 7 carbon atoms of a straight, branched, or cyclic configuration. Examples of lower alkylsulfonyl groups are methylsulfonyl, 2-butyl-sulfonyl, cyclohexylmethylsulfonyl, etc. By way of illustration the 2-butylsulfonyl group signifies $-S(O)_2CH(CH_3)CH_2CH_3$.

The term "alkylcarbonyl" includes "lower alkylcarbonyl" and means alkylcarbonyl groups of 1 to 20 carbon atoms of a straight, branched, or cyclic configuration. Examples of alkylcarbonyl groups are formyl, 2-methylbutanoyl, octadecanoyl, 11-cyclohexylundecanoyl and the like. Thus, the 11-cyclohexylundecanoyl group is c-Hex-$(CH_2)_{10}$—CO—.

"Lower alkylcarbonyl" means alkylcarbonyl groups of from 1 to 8 carbon atoms of a straight, branched, or cyclic configuration. Examples of lower alkylcarbonyl groups are formyl, 2-methylbutanoyl, cyclohexylacetyl, etc. By way of illustration, the 2-methylbutanoyl groups signifies $-COCH(CH_3)CH_2CH_3$.

The term $Ph(R^{26})_2$ indicates a phenyl group substituted with two $R^{26}$ substituents.

Halogen includes F, Cl, Br, and I.

It is intended that the definition of any substituent (e.g., $R^7$, $R^{12}$, $R^{26}$, etc.) in a particular molecule be independent of its definition elsewhere in the molecule. Thus, $-N(R^{12})_2$ represents $-NHH$, $-NHCH_3$, $-NHC_6H_5$, etc.

The rings formed when two $R^2$ groups join include cyclopropane, cyclobutane, cyclopentane, cyclohexane, cycloheptane, cyclooctane, oxetane, tetrahydrofuran, tetrahydropyran, 6,8-dioxabicyclo[3.2.1]octane, tetrahydrothiophene, tetrahydrothiopyran, pyrrolidine, piperidine, morpholine, thiamorpholine, and piperazine.

The heterocycles formed when two $R^{12}$, $R^{20}$, or $R^{28}$ groups join through N include pyrrolidine, piperidine, morpholine, thiamorpholine, piperazine, and N-methylpiperazine.

When $Q^1$ and $R^{22}$ and the carbons through which they are attached form a ring, the rings thus formed include lactones, lactams, and thiolactones.

The prodrug esters of Q (i.e., when Q=COOR$^6$) are intended to include the esters such as are described by Saari et al., *J. Med. Chem.*, 21, No. 8, 746–753 (1978), Sakamoto et al., *Chem. Pharm. Bull.*, 32, No. 6, 2241–2248 (1984) and Bundgaard et al., *J. Med. Chem.*, 30, No. 3,451–454 (1987). Within the definition of $R^8$, some representative monocyclic or bicyclic heterocyclic radicals are:

2,5-dioxo-1-pyrrolidinyl, (3-Pyridinylcarbonyl)amino, 1,3-dihydro-1,3-dioxo-2H-isoindol-2-yl, 1,3-dihydro-2H-isoindol-2-yl,
2,4-imidazolinedion-1-yl,
2,6-piperidinedion-1-yl,
2-imidazolyl,
2-oxo-1,3-dioxolen-4-yl,
piperidin-1-yl,
morpholin-1-yl, and
piperazin-1-yl.

The term "standard amino acid" means the following amino acids: alanine, asparagine, aspartic acid, arginine, cysteine, glutamic acid, glutamine, glycine, histidine, isoleucine, leucine, lysine, methionine, phenylalanine, proline, serine, threonine, tryptophan, tyrosine, and valine. (See F. H. C. Crick, *Symposium of the Society of Experimental Biology,* 1958 (12), p. 140.)

Optical Isomers—Diastereomers—Geometric Isomers

Some of the compounds described herein contain one or more asymmetric centers and may thus give rise to diastereomers and optical isomers. The present invention is meant to comprehend such possible diastereomers as well as their racemic and resolved, enantiomerically pure forms and pharmaceutically acceptable salts thereof.

Some of the compounds described herein contain olefinic double bonds, and unless specified otherwise, are meant to include both E and Z geometric isomers.

Salts

The pharmaceutical compositions of the present invention comprise a compound of Formula I as an active ingredient or a pharmaceutically acceptable salt, thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that in the discussion of methods of treatment which follows, references to the compounds of Formula I are meant to also include the pharmaceutically acceptable salts.

Utilities

The ability of the compounds of Formula I to antagonize the actions of the leukotrienes makes them useful for preventing or reversing the symptoms induced by the leukotrienes in a human subject. This antagonism of the actions of leukotrienes indicates that the compounds and pharmaceutical compositions thereof are useful to treat, prevent, or ameliorate in mammals and especially in humans: 1) pulmonary disorders including diseases such as asthma, chronic bronchitis, and related obstructive airway diseases, 2) allergies and allergic reactions such as allergic rhinitis, contact dermatitis, allergic conjunctivitis, and the like, 3) inflammation such as arthritis or inflammatory bowel disease, 4) pain, 5) skin disorders such as atopic eczema, and the like, 6) cardiovascular disorders such as angina, myocardial ischemia, hypertension, platelet aggregation, and the like, 7) renal insufficiency arising from ischaemia induced by immunological or chemical (cyclosporin) etiology, 8) migraine or cluster headache, 9) ocular conditions such as uveitis, 10) hepatitis resulting from chemical, immunological or infectious stimuli, 11 ) trauma or shock states such as burn injuries, endotoxemia, and the like, 12) allograft rejection, 13) prevention of side effects associated with therapeutic administration of cytokines such as Interleukin II and tumor necrosis factor, 14) chronic lung diseases such as cystic fibrosis, bronchitis and other small- and large-airway diseases, and 15) cholecystitis.

Thus, the compounds of the present invention may also be used to treat or prevent mammalian (especially, human) disease states such as erosive gastritis; erosive esophagitis; diarrhea; cerebral spasm; premature labor; spontaneous abortion; dysmenorrhea; ischemia; noxious agent-induced damage or necrosis of hepatic, pancreatic, renal, or myocardial tissue; liver parenchymal damage caused by hepatoxic agents such as $CCl_4$ and D-galactosamine; ischemic renal failure; disease-induced hepatic damage; bile salt induced pancreatic or gastric damage; trauma- or stress-induced cell damage; and glycerol-induced renal failure. The compounds also exhibit cytoprotective action.

The cytoprotective activity of a compound may be observed in both animals and man by noting the increased resistance of the gastrointestinal mucosa to the noxious effects of strong irritants, for example, the ulcerogenic effects of aspirin or indomethacin. In addition to lessening the effect of non-steroidal anti-inflammatory drugs on the gastrointestinal tract, animal studies show that cytoprotective compounds will prevent gastric lesions induced by oral administration of strong acids, strong bases, ethanol, hypertonic saline solutions, and the like.

Two assays can be used to measure cytoprotective ability. These assays are; (A) an ethanol-induced lesion assay and (B) an indomethacin-induced ulcer assay and are described in EP 140,684.

Dose Ranges

The magnitude of prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range for anti-asthmatic, anti-allergic or anti-inflammatory use and generally, uses other than cytoprotection, lie within the range of from about 0.001 mg to about 100 mg per kg body weight of a mammal, preferably 0.01 mg to about 10 mg per kg, and most preferably 0.1 to 1 mg per kg, in single or divided doses. On the other hand, it may be necessary to use dosages outside these limits in some cases.

For use where a composition for intravenous administration is employed, a suitable dosage range for anti-asthmatic, anti-inflammatory, or anti-allergic use is from about 0.001 mg to about 25 mg (preferably from 0.01 mg to about 1 mg) of a compound of Formula I per kg of body weight per day and for cytoprotective use from about 0.1 mg to about 100 mg (preferably from about 1 mg to about 100 mg and more preferably from about 1 mg to about 10 mg) of a compound of Formula I per kg of body weight per day.

In the case where an oral composition is employed, a suitable dosage range for anti-asthmatic, anti-inflammatory or anti-allergic use is, e.g. from about 0.01 mg to about 100 mg of a compound of Formula I per kg of body weight per day, preferably from about 0.1 mg to about 10 mg per kg and for cytoprotective use from 0.1 mg to about 100 mg (preferably from about 1 mg to about 100 mg and more preferably from about 10 mg to about 100 mg) of a compound of Formula I per kg of body weight per day.

For the treatment of diseases of the eye, ophthalmic preparations for ocular administration comprising 0.001–1% by weight solutions or suspensions of the compounds of Formula I in an acceptable ophthalmic formulation may be used.

The exact amount of a compound of the Formula I to be used as a cytoprotective agent will depend on, inter alia, whether it is being administered to heal damaged cells or to avoid future damage, on the nature of the damaged cells (e.g., gastrointestinal ulcerations vs. nephrotic necrosis), and on the nature of the causative agent. An example of the use of a compound of the Formula I in avoiding future damage would be co-administration of a compound of the Formula I with an NSAID that might otherwise cause such damage (for example, indomethacin). For such use, the compound of Formula I is administered from 30 minutes prior up to 30 minutes after administration of the NSAID. Preferably it is administered prior to or simultaneously with the NSAID, (for example, in a combination dosage form).

Pharmaceutical Compositions

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the an of pharmacy.

For administration by inhalation, the compounds of the present invention are conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of a compound of Formula I in suitable propellants, such as fluorocarbons or hydrocarbons.

Suitable topical formulations of a compound of formula I include transdermal devices, aerosols, creams, ointments, lotions, dusting powders, and the like.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719, the disclosures of which are hereby incorporated herein by reference.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 1 mg to about 500 mg of the active ingredient and each cachet or capsule contains from about l to about 500 mg of the active ingredient.

The following are examples of representative pharmaceutical dosage forms for the compounds of Formula I:

| Injectable Suspension (I.M.) | mg/mL |
|---|---|
| Compound of Formula I | 10 |
| Methylcellulose | 5.0 |
| Tween 80 | 0.5 |
| Benzyl alcohol | 9.0 |
| Benzalkonium chloride | 1.0 |
| Water for injection to a total volume of 1 mL | |

| Tablet | mg/tablet |
|---|---|
| Compound of Formula 1 | 25 |
| Microcrystalline Cellulose | 415 |
| Povidone | 14.0 |
| Pregelatinized Starch | 43.5 |
| Magnesium Stearate | 2.5 |
| | 500 |

| Capsule | mg/capsule |
|---|---|
| Compound of Formula 1 | 25 |
| Lactose Powder | 573.5 |
| Magnesium Stearate | 1.5 |
| | 600 |

| Aerosol | Per canister |
|---|---|
| Compound of Formula I | 24 mg |
| Lecithin, NF Liquid Concentrate | 1.2 mg |
| Trichlorofluoromethane, NF | 4.025 g |
| Dichlorodifluoromethane, NF | 12.15 g |

Combinations with Other Drugs

In addition to the compounds of Formula I, the pharmaceutical compositions of the present invention can also contain other active ingredients, such as cyclooxygenase inhibitors, non-steroidal anti-inflammatory drugs (NSAIDs), peripheral analgesic agents such as zomepirac diflunisal and the like. The weight ratio of the compound of the Formula I to the second active ingredient may be varied and will depend upon the effective dose of each ingredient. Generally, an effective dose of each will be used. Thus, for example, when a compound of the Formula I is combined with an NSAID the weight ratio of the compound of the Formula I to the NSAID will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

NSAIDs can be characterized into five groups:

(1) propionic acid derivatives;

(2) acetic acid derivatives;

(3) fenamic acid derivatives;

(4) oxicams; and (5) biphenylcarboxylic acid derivatives, or a pharmaceutically acceptable salt thereof.

The propionic acid derivatives which may be used comprise: alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen. Structurally related propionic acid derivatives having similar analgesic and anti-inflammatory properties are also intended to be included in this group.

Thus, "propionic acid derivatives" as defined herein are non-narcotic analgesics/non-steroidal anti-inflammatory drugs having a free —CH(CH₃)COOH or —CH₂CH₂COOH group (which optionally can be in the form of a pharmaceutically acceptable salt group, e.g., —CH(CH₃)COO—Na⁺ or —CH₂CH₂COO—Na⁺), typically attached directly or via a carbonyl function to a ring system, preferably to an aromatic ring system.

The acetic acid derivatives which may be used comprise: indomethacin, which is a preferred NSAID, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac. Structurally related acetic acid derivatives having similar analgesic and anti-inflammatory properties are also intended to be encompassed by this group.

Thus, "acetic acid derivatives" as defined herein are non-narcotic analgesics/non-steroidal anti-inflammatory drugs having a free —CH₂COOH group (which optionally can be in the form of a pharmaceutically acceptable salt group, e.g. —CH₂COO—Na⁺), typically attached directly to a ring system, preferably to an aromatic or heteroaromatic ring system.

The fenamic acid derivatives which may be used comprise: flufenamic acid, meclofenamic acid, mefenamic acid, niflumic acid and tolfenamic acid. Structurally related fenamic acid derivatives having similar analgesic and anti-inflammatory properties are also intended to be encompassed by this group.

Thus, "fenamic acid derivatives" as defined herein are non-narcotic analgesics/non-steroidal anti-inflammatory drugs which contain the basic structure:

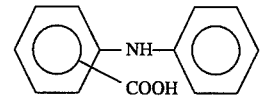

which can bear a variety of substituents and in which the free —COOH group can be in the form of a pharmaceutically acceptable salt group, e.g., —COO—Na⁺.

The biphenylcarboxylic acid derivatives which can be used comprise: diflunisal and flufenisal. Structurally related biphenylcarboxylic acid derivatives having similar analgesic and anti-inflammatory properties are also intended to be encompassed by this group.

Thus, "biphenylcarboxylic acid derivatives" as defined herein are non-narcotic analgesics/non-steroidal anti-inflammatory drugs which contain the basic structure:

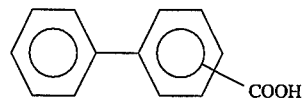

which can bear a variety of substituents and in which the free —COOH group can be in the form of a pharmaceutically acceptable salt group, e.g., —COO—Na⁺.

The oxicams which can be used in the present invention comprise: isoxicam, piroxicam, sudoxicam and tenoxican. Structurally related oxicams having similar analgesic and anti-inflammatory properties are also intended to be encompassed by this group.

Thus, "oxicams" as defined herein are non-narcotic analgesics/non-steroidal anti-inflammatory drugs which have the general formula:

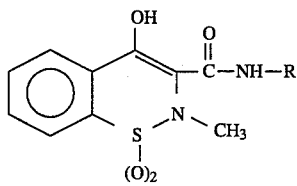

wherein R is an aryl or heteroaryl ring system.

The following NSAIDs may also be used: amfenac sodium, aminoprofen, anitrazafen, antrafenine, auranofin, bendazac lysinate, benzydanine, beprozin, broperamole, bufezolac, cinmetacin, ciproquazone, cloximate, dazidamine, deboxamet, delmetacin, detomidine, dexindoprofen, diacerein, di-fisalamine, difenpyramide, emorfazone, enfenamic acid, enolicam, epirizole, etersalate, etodolac, etofenamate, fanetizole mesylate, fenclorac, fendosal, fenflumizole, feprazone, floctafenine, flunixin, flunoxaprofen, fluproquazone, fopirtoline, fosfosal, furcloprofen, glucametacin, guaimesal, ibuproxam, isofezolac, isonixim, isoprofen, isoxicam, lefetamine HCl, leflunomide, lofemizole, lonazolac calcium, lotifazole, loxoprofen, lysin clonixinate, meclofenamate sodium, meseclazone, nabumetone, nictindole, nimesulide, orpanoxin, oxametacin, oxapadol, perisoxal citrate, pimeprofen, pimetacin, piproxen, pirazolac, pirfenidone, proglumetacin maleate, proquazone, pyridoxiprofen, sudoxicam, talmetacin, talniflumate, tenoxicam, thiazolinobutazone, thielavin B, tiaramide HCl, tiflamizole, timegadine, tolpadol, tryptamid, and ufenamate.

The following NSAIDs, designated by company code number (see e.g., *Pharmaprojects*), may also be used: 480156S, AA861, AD1590, AFP802, AFP860, AI77B, AP504, AU8001, BPPC, BW540C, CHINOIN 127, CN100, EB382, EL508, F1044, GV3658, ITF182, KCNTEI6090, KME4, LA2851, MR714, MR897, MY309, ONO3144, PR823, PV102, PV108, R830, RS2131, SCR152, SH440, SIR133, SPAS510, SQ27239, ST281, SY6001, TA60, TAI-901 (4-benzoyl-1- indancarboxylic acid), TVX2706, U60257, UR2301, and WY41770.

Finally, NSAIDs which may also be used include the salicylates, specifically acetyl salicylic acid and the phenylbutazones, and pharmaceutically acceptable salts thereof.

In addition to indomethacin, other preferred NSAIDs are acetyl salicylic acid, diclofenac, fenbufen, fenoprofen, flurbiprofen, ibuprofen, ketoprofen, naproxen, phenylbutazone, piroxicam, sulindac, and tolmetin.

Pharmaceutical compositions comprising the Formula I compounds may also contain inhibitors of the biosynthesis of the leukotrienes such as are disclosed in EP 138,481 (Apr. 24, 1985), EP 115,394 (Aug. 8, 1984), EP 136,893 (Apr. 10, 1985), and EP 140,709 (May 8, 1985), which are hereby incorporated herein by reference.

The compounds of the Formula I may also be used in combination with leukotriene antagonists such as those disclosed in EP 106,565 (Apr. 25, 1984) and EP 104,885 (Apr. 4, 1984) which are hereby incorporated herein by reference and others known in the art such as those disclosed in EP Application Nos. 56,172 (Jul. 21, 1982) and 61,800 (Jun. 10, 1982); and in U.K. Patent Specification No. 2,058, 785 (Apr. 15, 1981 ), which are hereby incorporated herein by reference.

Pharmaceutical compositions comprising the Formula I compounds may also contain as the second active ingredient, prostaglandin antagonists such as those disclosed in EP 11,067 (May 28, 1980) or thromboxane antagonists such as those disclosed in U.S. Pat. No. 4,237,160. They may also contain histidine decarboxylase inhibitors such as α-fluoromethyl-histidine, described in U.S. Pat. No. 4,325,961. The compounds of the Formula I may also be advantageously combined with an $H_1$- or $H_2$-receptor antagonist, such as for instance acetamazole, aminothiadiazoles disclosed in EP 40,696 (Dec. 2, 1981), benadryl, cimetidine, famotidine, framamine, histadyl, phenergan, ranitidine, terfenadine and like compounds, such as those disclosed in U.S. Pat. Nos. 4,283,408; 4,362,736; and 4,394,508. The pharmaceutical compositions may also contain a $K+/H+$ ATPase inhibitor such as omeprazole, disclosed in U.S. Pat. No. 4,255,431, and the like. Compounds of Formula I may also be usefully combined with most cell stabilizing agents, such as 1,3-bis(2-carboxychromon-5 -yloxy)-2-hydroxypropane and related compounds described in British Patent Specifications 1,144,905 and 1,144,906. Another useful pharmaceutical composition comprises the Formula I compounds in combination with serotonin antagonists such as methysergide, the serotonin antagonists described in *Nature*, 316, 126–131 (1985), and the like. Each of the references referred to in this paragraph is hereby incorporated herein by reference.

Other advantageous pharmaceutical compositions comprise the Formula I compounds in combination with anticholinergics such as ipratropium bromide, bronchodilators such as the beta agonist salbutamol, metaproterenol, terbutaline, fenoterol and the like, and the anti-asthmatic drugs theophylline, choline theophyllinate and enprofylline, the calcium antagonists nifedipine, diltiazem, nitrendipine, verapamil, nimodipine, felodipine, etc. and the corticosteroids, hydrocortisone, methylprednisolone, betamethasone, dexamethasone, beclomethasone, and the like.

Methods of Synthesis

Compounds of the present invention can be prepared according to the following methods. Temperatures are in degrees Celsius.

Method A

Methyl ester II is treated with an excess of a reducing reagent such as lithium aluminum hydride in a solvent like THF at 0° C. to afford an alcohol, which is oxidized with a reagent such as manganese dioxide to give aldehyde III. Compound III is condensed with acetone in a basic medium to form thieno[3,2-b]pyridine IV, which is transformed into 2- or 3-substituted or 2,3-di-substituted thienopyridine V according to the procedures described in Methods B, C and D. Treatment of thienopyridine V with a halogenating reagent such as NBS, followed by reaction with triphenylphosphine gives phosphonium salt VI. Reaction of VI with aldehyde VII in the presence of a strong base such as potassium tert-butoxide, potassium bis(trimethylsilyl)amide or butyl lithium, followed by hydrolysis with aqueous sodium hydroxide affords VIII. Examples of VII are described in U.S. Pat. No. 5,104,882, (Methods D and I), in EP 480,717 (Method H), as well as in the present examples.

Method B

Treatment of thienopyridine IV obtained by Method A, with a chlorinating reagent, such as trichloroisocyanuric acid or sulfuryl chloride gives 2,3-dichlorothienopyridine Ve. Reaction of IV with chlorine in conc. sulfuric acid in the presence of silver sulfate affords 3-chlorothieno-pyridine Vf. Treatment of IV with strong base such as alkyl lithium or LDA gives the thienopyridin-2-yl anion, which reacts with different electrophiles to give different substitution on the 2-position of IV; e.g., the anion 1) reacts with NCS or chlorine to give 2-chlorothienopyridine Va; 2) reacts with N-fluoro-bis(benzenesulfonyl)amide $(PhS(O)_2)_2NF$, or fluorine perchlorate ($FClO_4$) to give 2-fluorothienopyridine Vb;

3) reacts with cyanogen bromide (BrCN) to give 2-cyanothienopyridine Vc; and 4) reacts with trifluoromethane sulfonic anhydride to give 2-trifluoromethylsulfonyl thienopyridine Vd.

Method C

2-Chloro-, or 2-fluorothienopyridine (Va,b) is converted to different 2,3-disubstituted thienopyridines by the following sequences: 1) deprotonation of 2-chloro or 2-fluorothienopyridine (Va,b) with a strong base, such as an alkyl lithium or LDA gives 2-chloro- or 2-fluorothienopyridin-3-yl anion; 2) reaction of the anion with different electrophiles to form different 2,3-disubstituted thienopyridines: e.g., reaction with N-fluoro-bis(benzenesulfonyl)amide or fluorine perchlorate to give Vh; reaction with trifluoromethanesulfonic anhydride to give Vi; reaction with N-bromosuccinimide or bromine to give Vj; and reaction with N-chloro-succinimide or chlorine to give Vk.

2-Chloro-3-fluorothienopyridine (Vh, X=Cl) is converted to 3-fluorothienopyridine (Vg) by following the sequence: 1) reaction with tert-butyl lithium in THF; 2) protonation with water.

Method D

3-Chloro-, or 3-fluorothienopyridine (Vf,g), prepared by Method B and Method C, is deprotonated with a strong base, such as alkyl lithium or LDA, to form 3-chloro or 3-fluorothienopyridino-2-yl anion, which reacts with various electrophiles to give 2,3-disubstituted thienopyridines; e.g., reaction with cyanogen bromide gives VI; reaction with trifluoromethane-sulfonic anhydride gives Vm; reaction with methanesulfonyl chloride gives Vn; reaction with N-fluoro-bis(benzenesulfonyl)amide or fluorine perchlorate gives Vo; and reaction with N-chlorosuccinimide or chlorine gives Vp.

Method E

The double bond in compound VIII is reduced to a single bond by borane in THF. Thus, treatment of VIII methyl ester with excess of borane in THF, followed by hydrolysis of the methyl ester, gives acid IX.

Method F

The iodopyridine XI reacts with trimethylsilylacetylene (X) in the presence of copper(I) iodide and triphenylphosphine palladium(II) chloride complex to afford furano[3,2-b]pyridine XII, which is converted to 2,3-dichloro-furanopyridine XIVa by chlorination with trichloroisocyanuric acid or sulfuryl chloride or converted to XIII by desilylation with hydrogen fluoride in the presence of pyridine. Both XIVa and XIII are convened to different 2,3-disubstituted furanopyridines XIV by the reactions described in Methods B, C, D, and J. Finally, XIV is transformed into acid XV by using procedures described in Method A.

Method G

Aldehyde III, prepared according to Method A, is condensed with sodium pyruvate, followed by esterification with methanol in the presence of conc. hydrochloric acid, to give methyl ester XVI. Chlorination of XVI with either sulfuryl chloride or trichloroisocyanuric acid affords 2,3-dichloro-thienopyridine XVII. XVII is convened to phosphonium salt XVIII by the following sequence: 1) reduction with DIBAL in THF; 2) displacement of the hydroxy group with a chlorine by reaction with a chlorinating reagent, such as thionyl chloride; and 3) reaction with triphenylphosphine in an organic solvent, such as toluene or acetonitrile. XVIII is convened to the final product VIII by the procedure described in Method A.

Method H

The compound XIX is treated with an acid chloride in the presence of base, followed by reaction with phosphorus pentasulfide in THF in the presence of a base like $Na_2CO_3$, to afford thiazolopyridine XX. Oxidation of XX with MCPBA gives an N-oxide, which reacts with trimethylsilyl cyanide and a dialkyl carbamoyl chloride to form nitrile XXI. Nitrile XXI is convened to a phosphonium salt by the following sequence: 1) reduction of nitrile XXI with DIBAL in THF to give an aldehyde; 2) reduction of the aldehyde with $NaBH_4$ in THF—$CH_3OH$; 3) mesylation of the alcohol with mesyl chloride in the presence of triethylamine; and 4) reaction of the mesylate with triphenylphosphine. The phosphonium salt is convened to the final acid by the procedures described in Method A.

Method I

Thiophene ester XXIV, prepared according to the literature procedures (K. H. Weber and H. Daniel; *Annalen* (1979) 328; H. K. Gakhar, A. Khanna and P. Baveja; *Indian J. Chem.* 16B (1928) 305) is transformed into thieno[2,3-b]pyridine XXV by the following sequence: 1) reduction with lithium aluminum hydride in THF; 2) oxidation with manganese oxide; and 3) condensation with acetone in the presence of a base, such as sodium hydroxide. XXV is convened to XXVI by the methods described in Method J. Finally, the XXVI is convened to acid XXVII using the procedures described in Method A.

Method J

Thieno[2,3-b]pyridine XXV is chlorinated either with sulfuryl chloride or with trichloroisocyanuric acid to afford 2,3-dichloro-thienopyridine XXVIa.

Deprotonation of XXV with a strong base such as an alkyl lithium or LDA in THF forms the thienopyridin-2-yl anion, which reacts with N-chlorosuccinimide or chlorine to afford 2-chlorothienopyridine XXVIb; or it reacts with N-fluoro-bis(benzenesulfonyl)amide or fluorine perchlorate to give 2-fluorothienopyridine XXVIc.

Deprotonation of XXVIc with either an alkyl lithium or LDA followed by reaction with N-fluoro-bis(benzenesulfonyl) amide or fluorine perchlorate affords difluorothienopyridine XXVIi.

Deprotonation of XXVIb with either an alkyl lithium or LDA, followed by reaction with an electrophilic reagent, gives a 2,3-disubstituted thienopyridine; e.g., reaction with cyanogen bromide gives XXVIe; reaction with N-fluoro-bis(benzenesulfonyl)amide or fluorine perchlorate gives XXXIf; reaction with trifluoromethanesulfonic anhydride gives XXVId.

Treatment of XXVIa or XXVIf with ten-butyl lithium, followed by quenching with aqueous amonium chloride, affords XXVIh or XXVIg, respectively.

Method K

Ketone XXVIII is convened to chiral allylic alcohol XXIX by the following sequence: 1) chiral reduction by Corey's method ($BH_3$/oxazaborolidine complex (*J. Am. Chem. Soc.* 1987, 109, 5551 and 7925)); 2) reaction with α-bromomethyl acrylic ester in the presence of base; and 3) reduction with DIBAL. Treatment of XXIX with diazomethane/Pd(OAc)$_2$, then with mesyl chloride and triethyl amine, followed by displacement with sodium cyanide, and then hydrolysis with potassium hydroxide gives acid XXX. Acid XXX is transformed into ten-alcohol XXXI by lithiation with nBuLi, followed by addition of acetone. Both XXX and XXXI are convened to aldehydes XXXII and XXXIII by the following reactions: 1) esterification with diazomethane; 2) removal of THP-protecting group with PPTS, and 3) oxidation with manganese dioxide. The aldehydes XXXII and XXXIII are convened to the final acid XXXIIIa by the procedures described in Method A.

Method L

3-Aminothiophene XXXIV is converted to aminoketone XXXV by reaction with bromoketone XL (prepared from known compound α,α'-dihydroxyacetone in two steps: 1) monoprotection with TBDMSCl; and 2) bromination with $CBr_4$ and DIPHOS in the presence of a base such as $K_2CO_3$).

XXXV is transformed to thieno[2,3-b]pyrazine XXXVI by the following sequence: 1) bromination on the α-position of the thiophene ting with one equiv. of bromine; 2) treatment of the bromo-compound with liquid ammonia at −80° C.; and 3) oxidation with oxygen. XXXVI is converted to fluorothienopyrazine XXXVII by the procedures described in Method B.

Phosphonium salt XXXVIII is prepared from XXXVII by the following sequence: 1) removal of TBDMS ether with PPTS; 2) bromination with carbon tetrabromide and DIPHOS; and 3) reaction with triphenylphosphine. The final product XXXIX is prepared from phosphonium salt XXX-VIII by using procedures described in Method A.

Method M

Reaction of phosphonium salt VI with the monoprotected acetal of an isophthalaldehyde in the presence of strong base such as potassium tert-butoxide, potassium bis(trimethylsilyl)amide or butyllithium followed by pyridinium p-toluenesulfonate hydrolysis and treatment with vinyl magnesium bromide affords the allylic alcohol (XL). Treatment of alcohol (XL) with variously substituted aryl iodides (I-Ar-$R^{23}Q^2$) suitably protected when needed, in the presence of palladium (II) acetate, and a weak base such as lithium acetate in DMF, yields the ketone XLI. Reduction of the ketone with a chiral catalyst such as the Corey catalyst (CBS)* gives the corresponding alcohol XLII, which can be sulfonylated with a sulfonyl chloride or fluoride ($R_{13}S(O)_2Cl(F)$) in standard solvents such as methylene chloride, THF etc., in the presence of a weak base such as triethylamine, N-methylpiperidine and the like, and the sulfonate displaced with the dilithium salt of a thiolacid, prepared with 2 equivalent of butyllithium. The desired product is obtained after removal of the protecting group when needed.

* (Refs: Mathre et al., *J. Org. Chem.* 1991, 56, 751–762; Corey et al., *J. Am. Chem. Soc.* 1987, 109, 5551–5553).

Method N

Reaction of dichlorothienopyridine (Ve), prepared according to methods A and B, with an isophthalaldehyde between 100° and 200° C., and an acid such as camphorsulfonic acid in a neutral solvent such as mesitylene or xylene affords, after refluxing overnight, the aldehyde XLIV. Treatment of this aldehyde with vinylmagnesium bromide in toluene at 0° furnishes the allylic alcohol (XLV) which may be coupled with a methyl 2-iodobenzoate using a catalyst such as palladium(II) acetate to yield the ketoester XLVI. Chiral reduction of the ketone with a chiral catalyst such as (−)-DIP-Cl® (Aldrich trademark for B-chlorodiisopinocampheylborane) gives the corresponding alcohol XLVII. Reaction of this alcohol with MeMgCl previously treated with $CeCl_3$ in THF affords a diol which can be sulfonylated as in Method M and the sulfonate displaced with the dilithium salt of the thiolacid prepared with 2 equivalents of butyllithium, to give XLVIII.

Method O

The allylic alcohol XL, prepared according to method M, is oxidized in a solvent like ethyl acetate at 50° C. with a reagent such as manganese dioxide to give the corresponding ketone. Treatment of this ketone with a mild base such as triethylamine in THF at −5° C. with an aromatic thiol gives ketone XLIX. Chiral reduction of the ketone with a chiral catalyst such as (−)-DIP—Cl® gives the corresponding alcohol L, which can be sulfonylated with a sulfonyl chloride or fluoride ($R^{13}S(O)_2Cl(F)$) in standard solvents such as methylene chloride, THF etc., in the presence of a weak base such as triethylamine, N-methylpiperidine and the like. The resulting sulfonate is displaced with the dilithium salt of the thiolacid (see Example 4B), prepared with 2 equivalents of butyllithium to afford the desired product LI.

Method P

The tetrahydrothiophen-3-one LII is treated with hydroxylamine hydrochloride in a solvent such as ethanol and in the presence of a base such as barium carbonate at reflux to yield an oxime. This oxime is reacted with HCl in a solvent such as methanol to give 3-aminothiophene, which is treated with $Ac_2O$ and a base such as NaOH at 60° C. to give N-acetyl-3-aminothiophene. In the next step phosphorus oxychloride ($POCl_3$) is reacted with cold DMF neat. After a few minutes the reaction mixture is diluted with a solvent such as dichloroethane, the N-acetyl-3-aminothiopene in the same solvent is added thereto, and the mixture is refluxed to yield LIII. The chlorinated thienopyridine LIII is treated with a chlorinating reagent, such as trichloroisocyanuric acid or sulfuryl chloride to give LIV which, in the presence of compound LV and a base or a hydride such as sodium hydride, affords LVI. LV is obtained by the reduction of VII with a reducing agent such as sodium borohydride in methanol, followed by the hydrolysis of the ester with a base such as sodium hydroxide.

Method Q

Thienopyridine ester XVII is reduced to the alcohol with a hydride such as DIBAL at −78° C. in THF. The resulting alcohol is reacted with thionyl chloride ($SOCl_2$) to give the chloride LVII. Reaction of 3-(7-chloroquinoline-2-ylmethoxy)benzaldehyde (U.S. Pat. No. 4,851,409 example 16 step 1) with vinyl magnesium bromide followed by palladium-catalysed coupling of the resulting allylic alcohol with an ortho-halobenzoate (U.S. Pat. No. 5,266,568 Method J) yields the keto ester LVIII. Heating LVIII in DMF at 100° C. with a copper salt such as copper(II) chloride yields the ketophenol LIX. Chloride LVII is coupled with the phenol LIX in DMF and in the presence of a base such as cesium carbonate at 50° C. overnight to give LX. Reduction of the ketone LX with a chiral catalyst such as described in J. Org. Chem. 56, 751, (1991 ) gives the corresponding alcohol LXI, which can be sulfonylated with a sulfonyl chloride or fluoride in standard solvents such as methylene chloride, THF etc., in the presence of a weak base such as triethylamine, N-methylpiperidine and the like, and the resulting sulfonate displaced with the disodium salt of thiolacid (Example 4B), prepared with 2 equivalents of butyllithium. The final product LXII is obtained by reacting the carboxylic ester with MeMgCl previously treated with $CeCl_3$ in THF.

Method R

Compound VIII as its methyl ester is treated overnight with trimethylsulfoxonium iodide and a hydride such as sodium hydride in DMSO to yield LXIII after basic hydrolysis of the ester with NaOH.

Method S

Compound LXIV, an intermediate obtained in method M, is treated with a thiolacid and a thiolamide in the presence of a Lewis acid such as $BF_3·OEt_2$, trifluoroacetic acid, etc. in a solvent such as dichloromethane and the like at −15° C. to yield LXV, LXVI and LXVII which are readily separated from each other by chromatography.

It will be recognized by one skilled in the art that the various substituents ($R^1$, $R^5$, $R^{23}$, etc.) must be compatible with the specific chemistry in each case. Protecting groups known in the art may be used advantageously in certain cases.
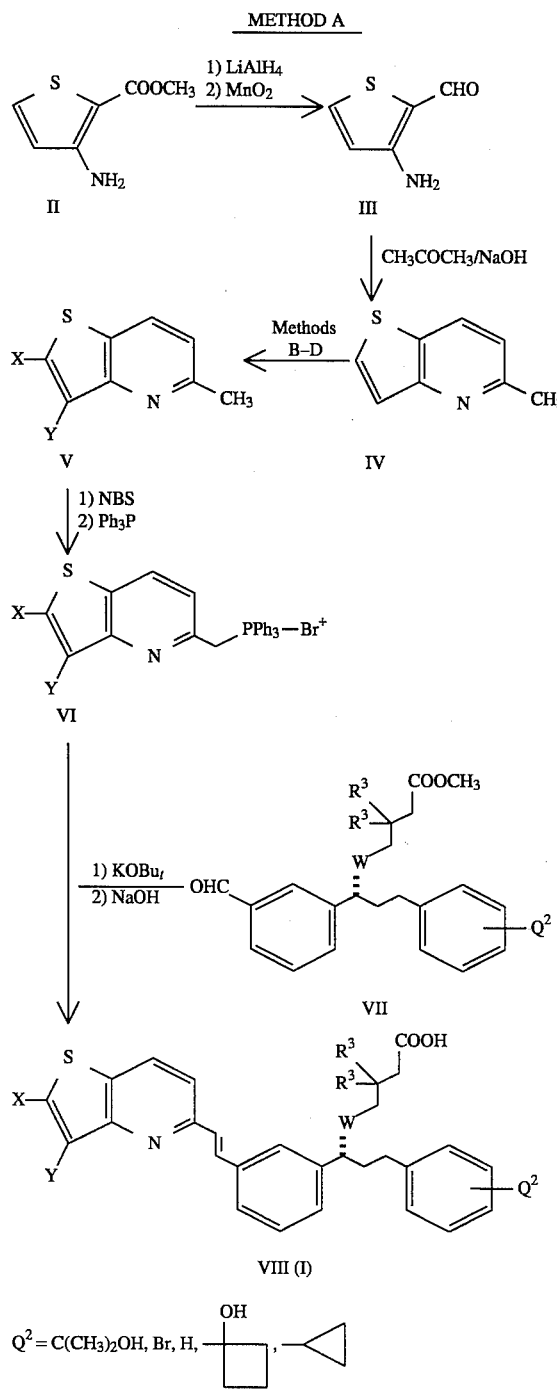
$Q^2 = C(CH_3)_2OH, Br, H,$ [cyclobutanol], cyclopropyl
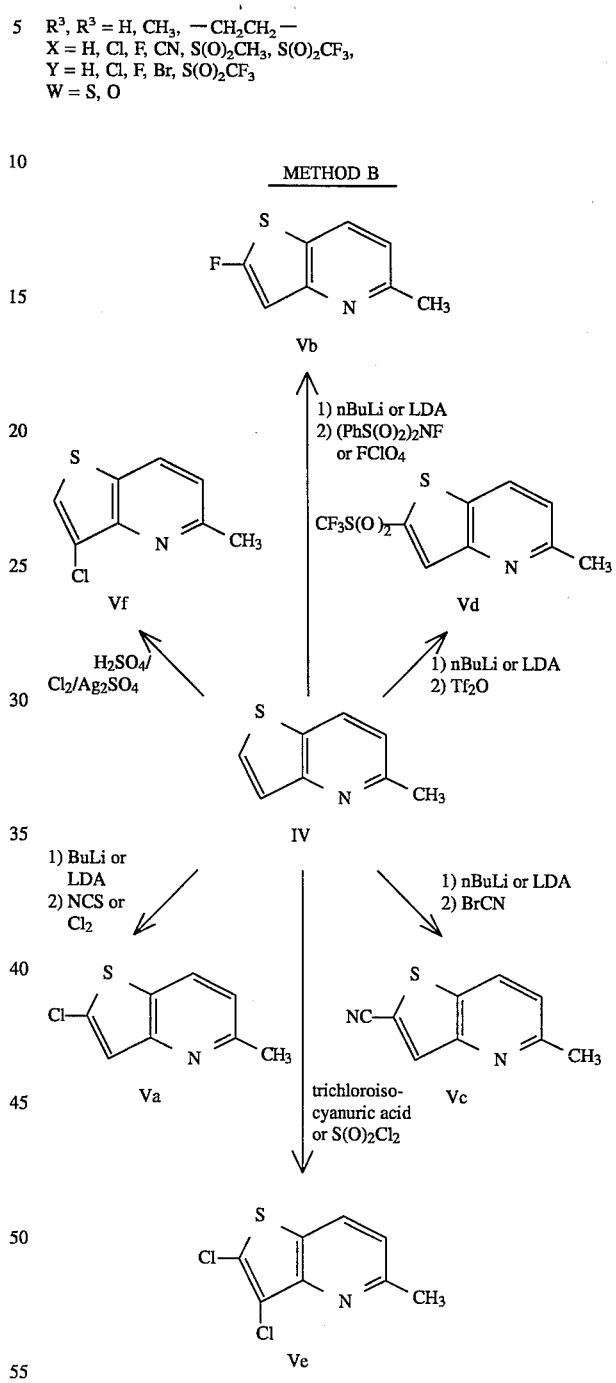
$R^3, R^3 = H, CH_3, -CH_2CH_2-$
$X = H, Cl, F, CN, S(O)_2CH_3, S(O)_2CF_3,$
$Y = H, Cl, F, Br, S(O)_2CF_3$
$W = S, O$

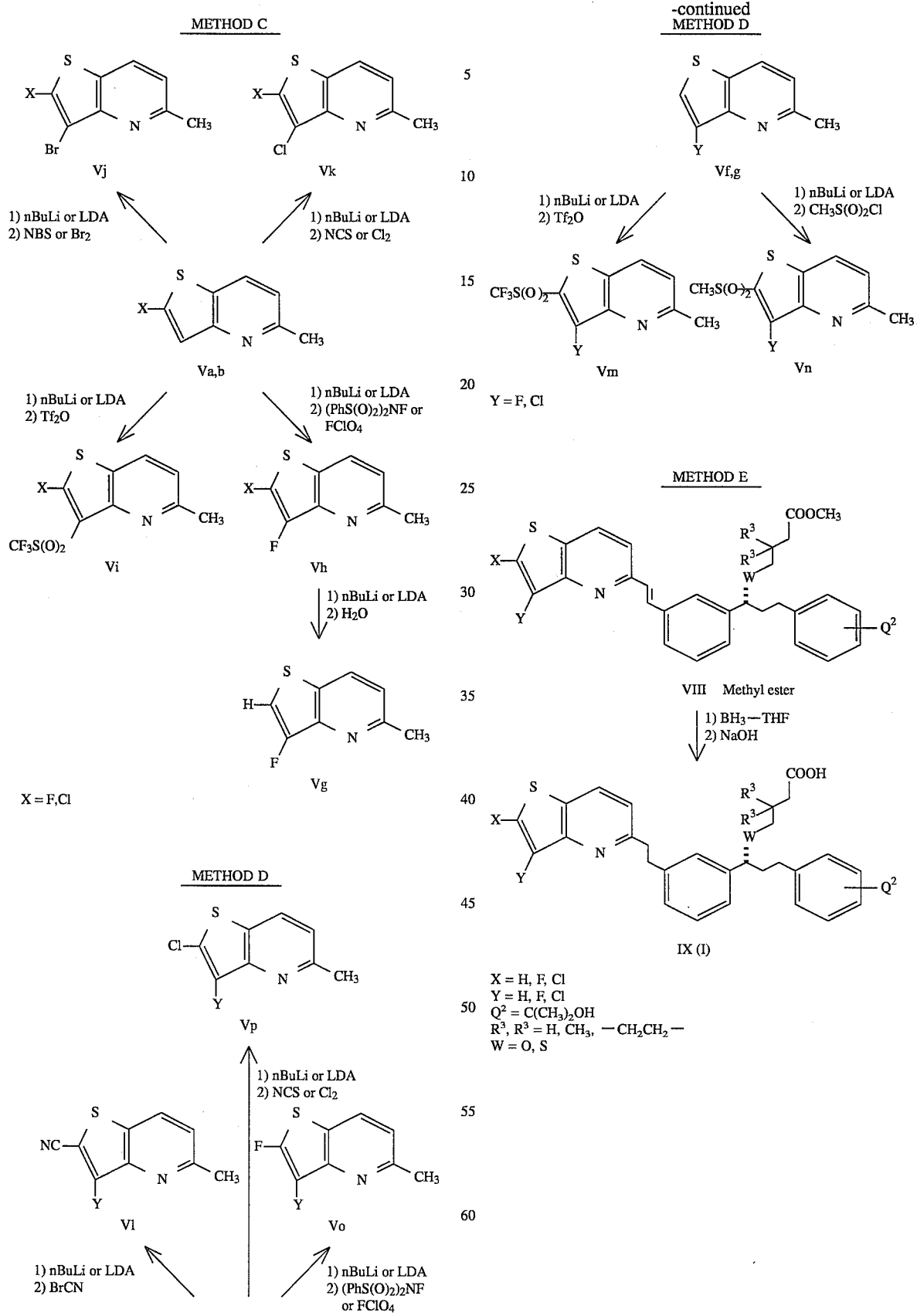

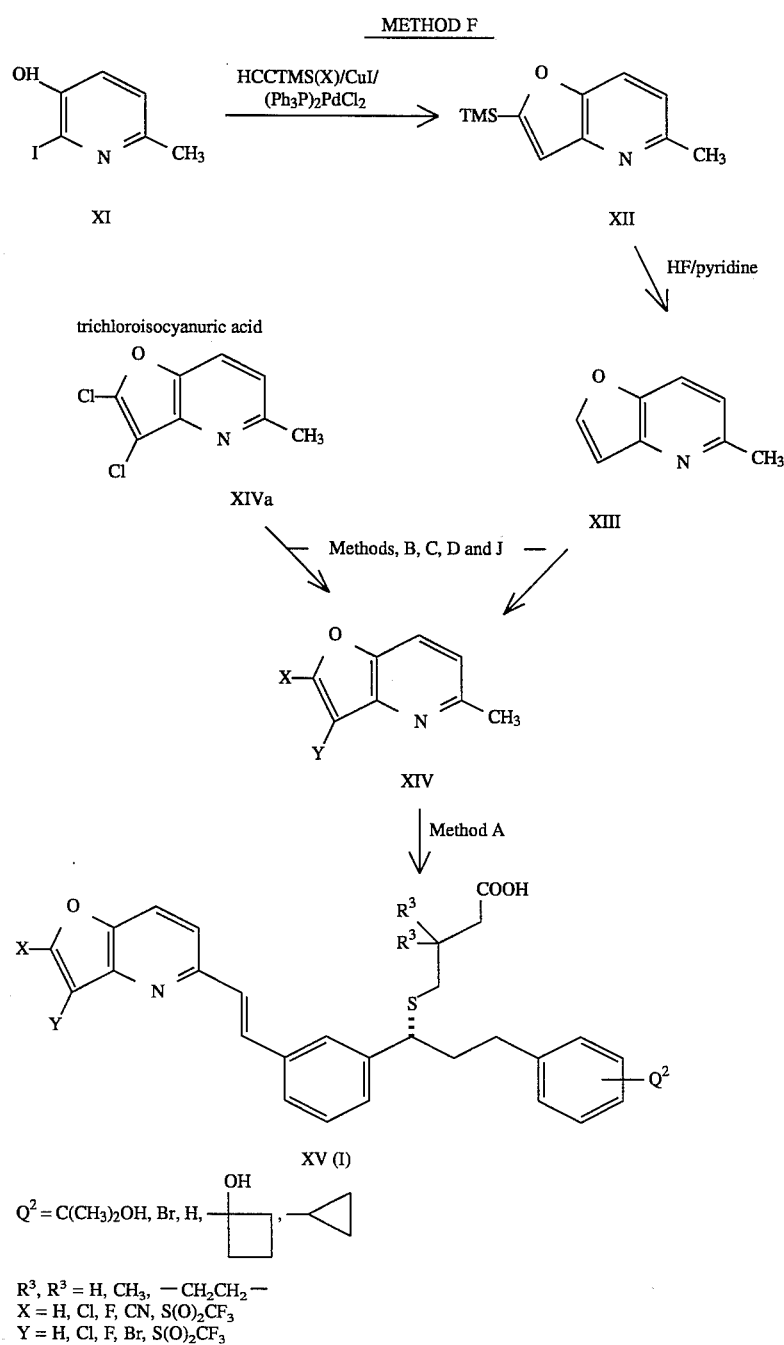

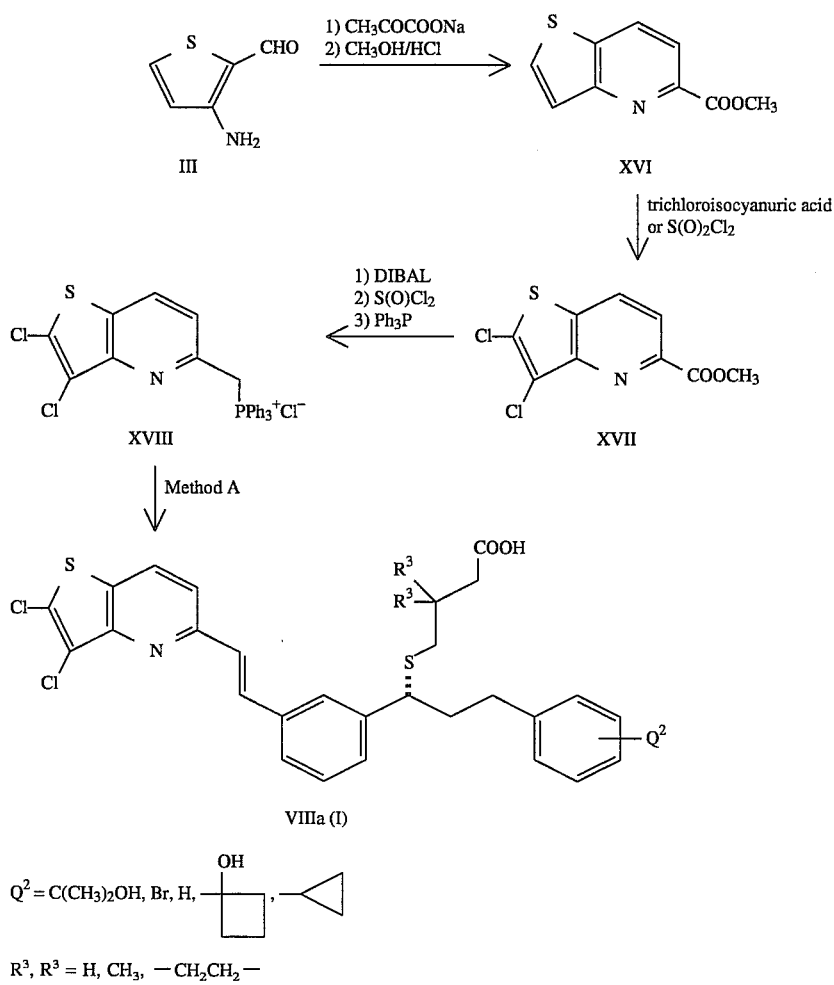

METHOD H
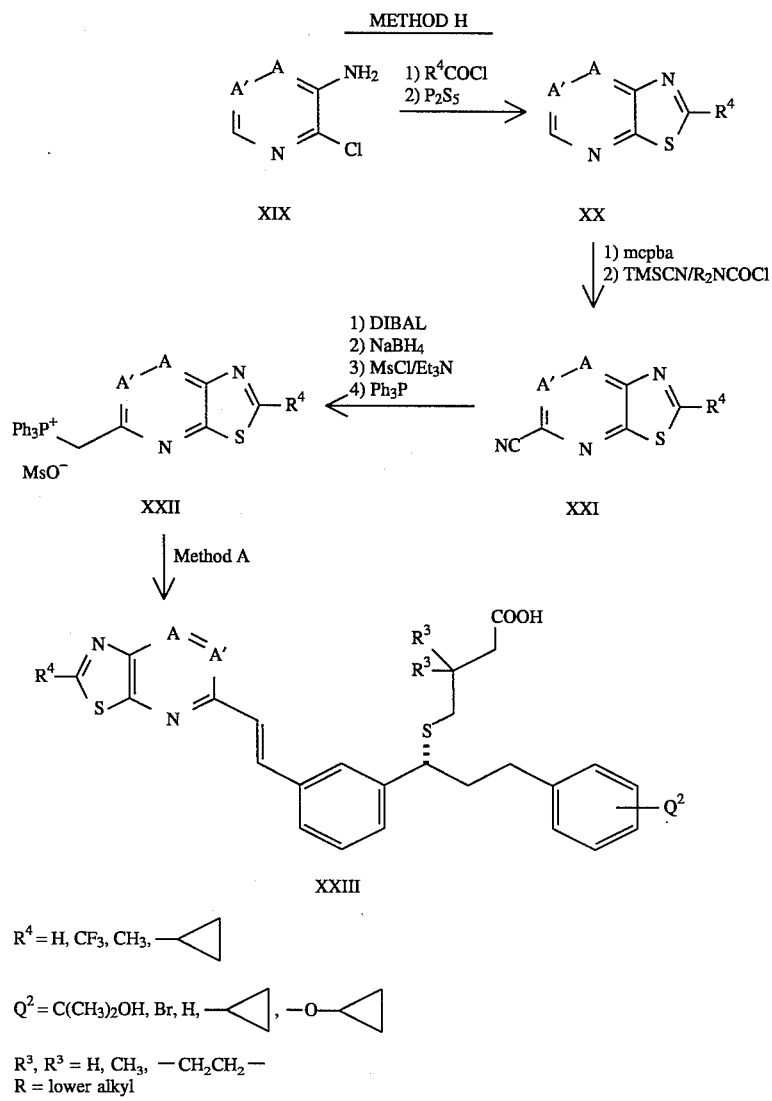
$R^4$ = H, CF$_3$, CH$_3$, —◁
$Q^2$ = C(CH$_3$)$_2$OH, Br, H, —◁, —O—◁
$R^3$, $R^3$ = H, CH$_3$, —CH$_2$CH$_2$—
R = lower alkyl
METHOD I
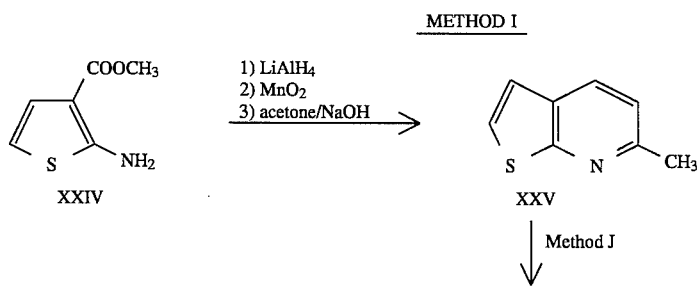

-continued
METHOD I
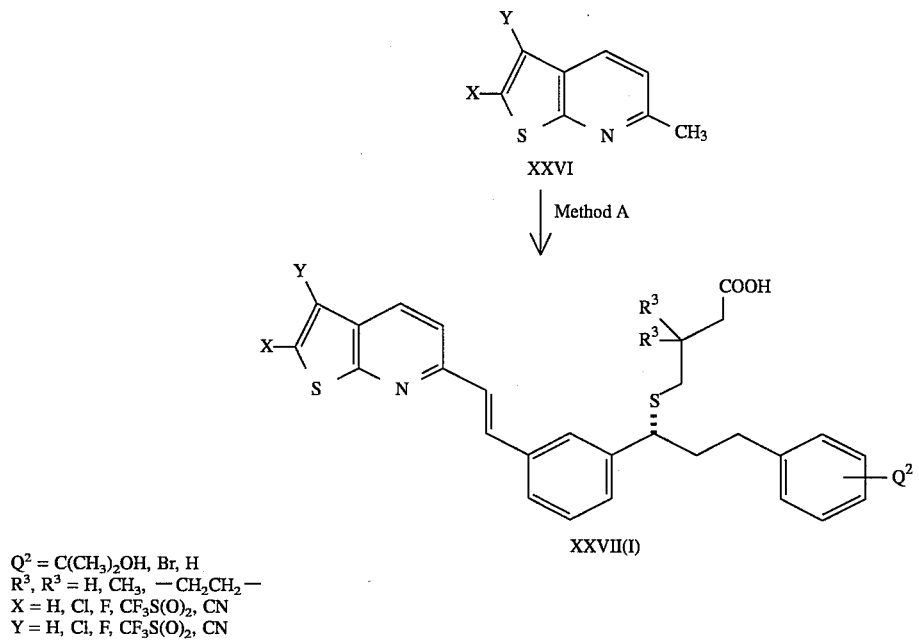
$Q^2 = C(CH_3)_2OH$, Br, H
$R^3, R^3 = H, CH_3, -CH_2CH_2-$
X = H, Cl, F, $CF_3S(O)_2$, CN
Y = H, Cl, F, $CF_3S(O)_2$, CN
METHOD J
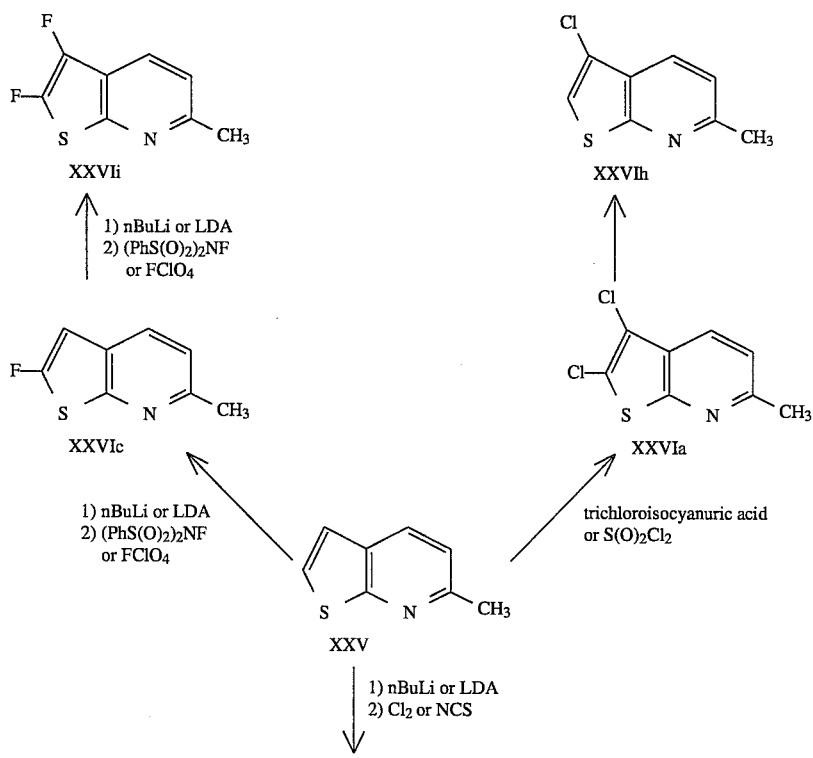

-continued
METHOD J
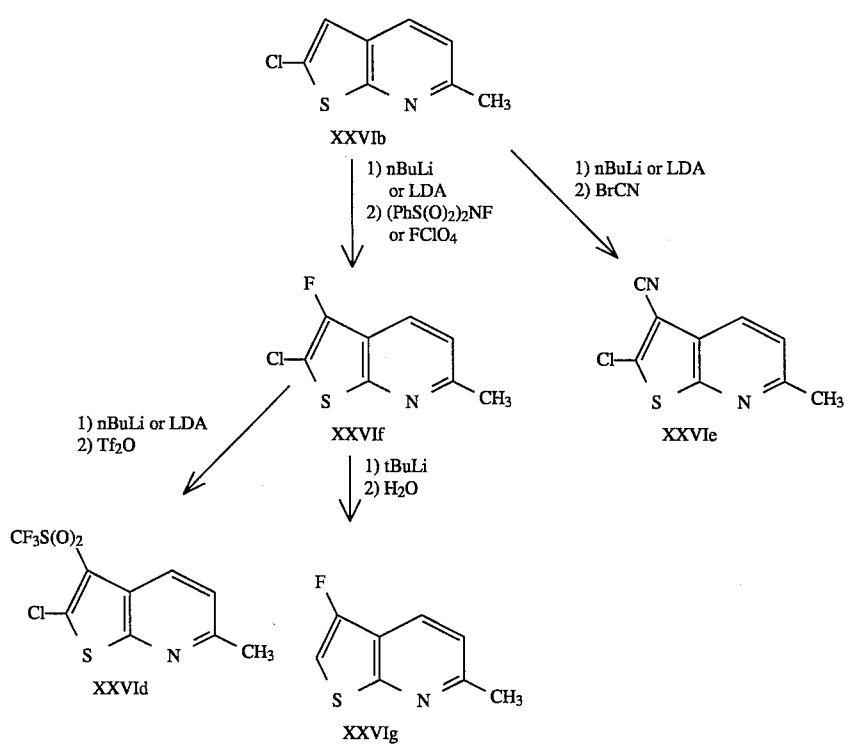
METHOD K
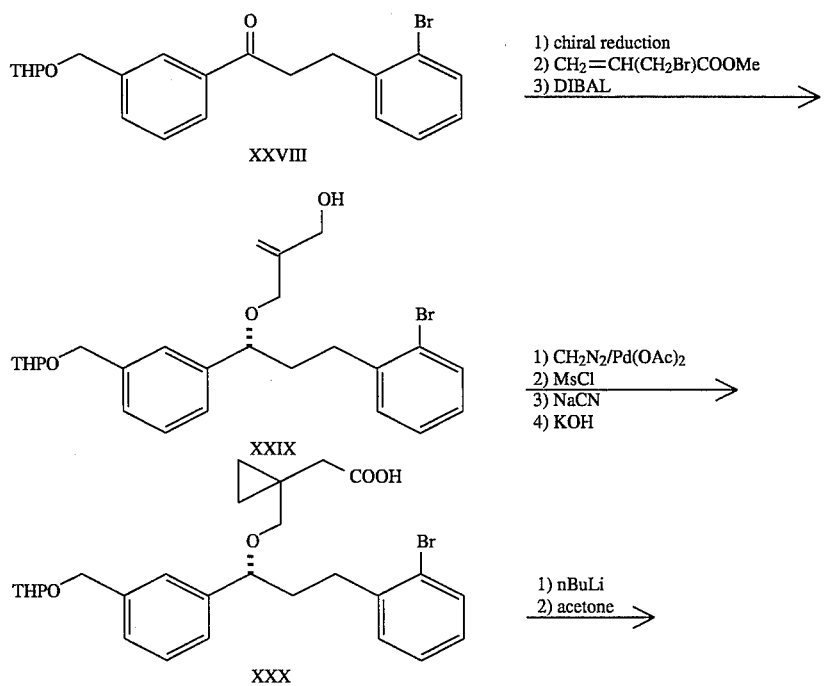

-continued
METHOD K
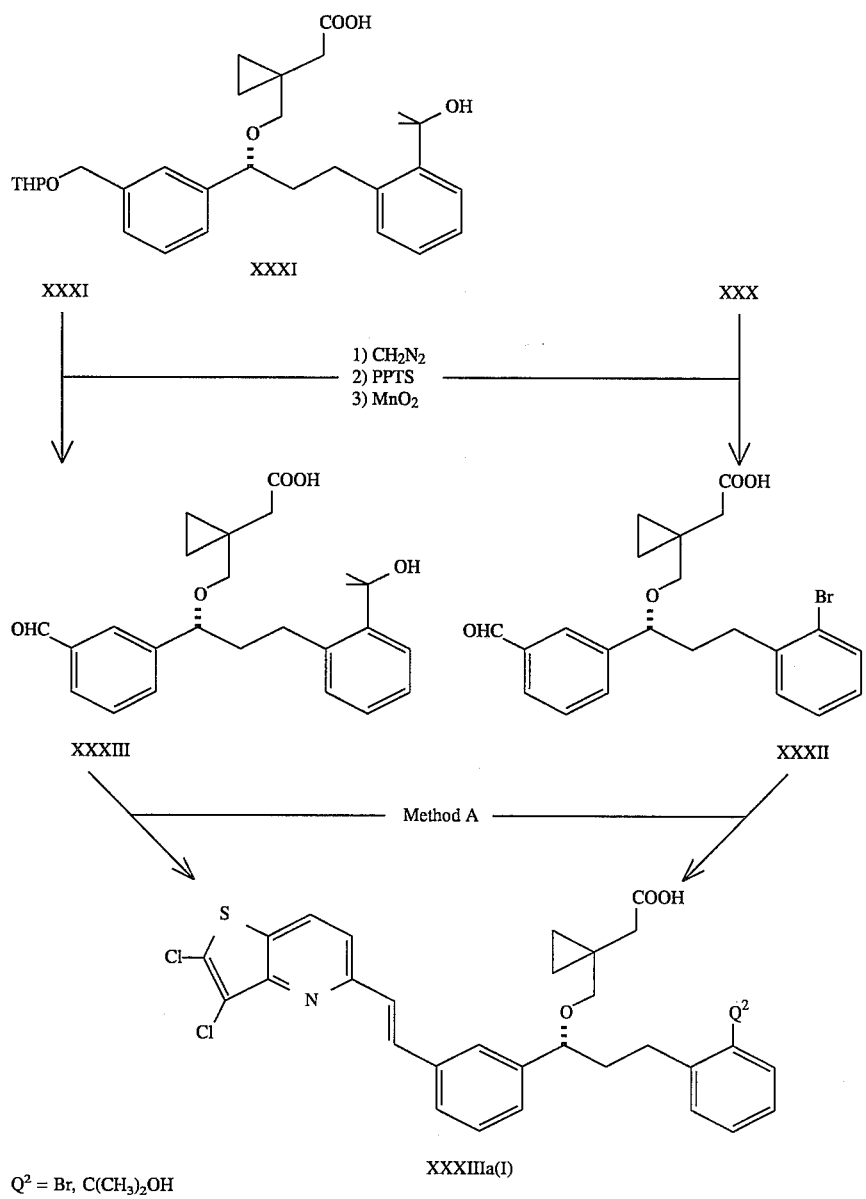
$Q^2$ = Br, $C(CH_3)_2OH$
METHOD L
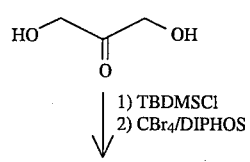
1) TBDMSCl
2) $CBr_4$/DIPHOS

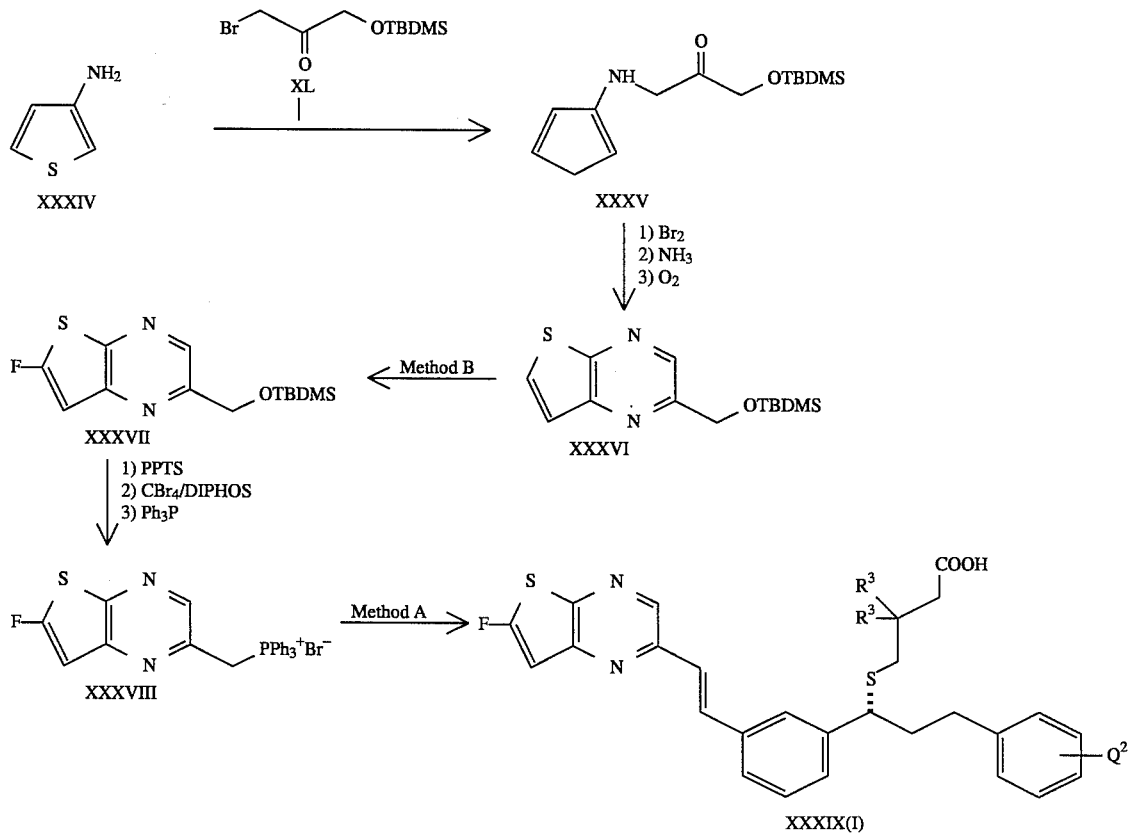
$Q^3 = C(CH_3)_2OH$, Br, H,
$R^3, R^3 = H, CH_3, -CH_2CH_2-$
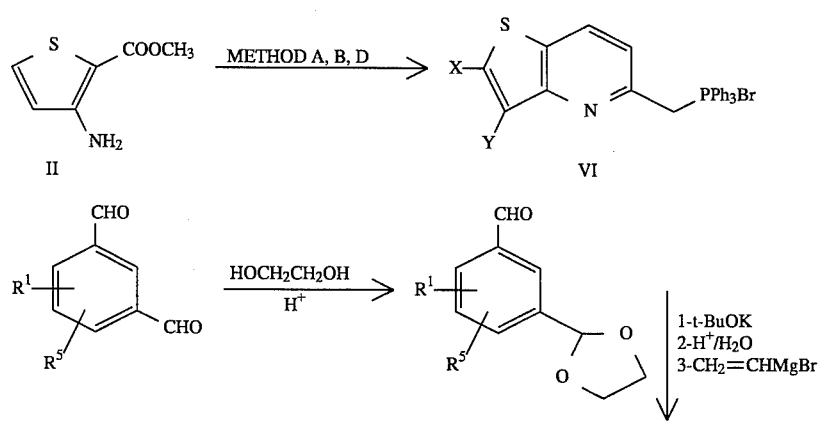

-continued
METHOD M
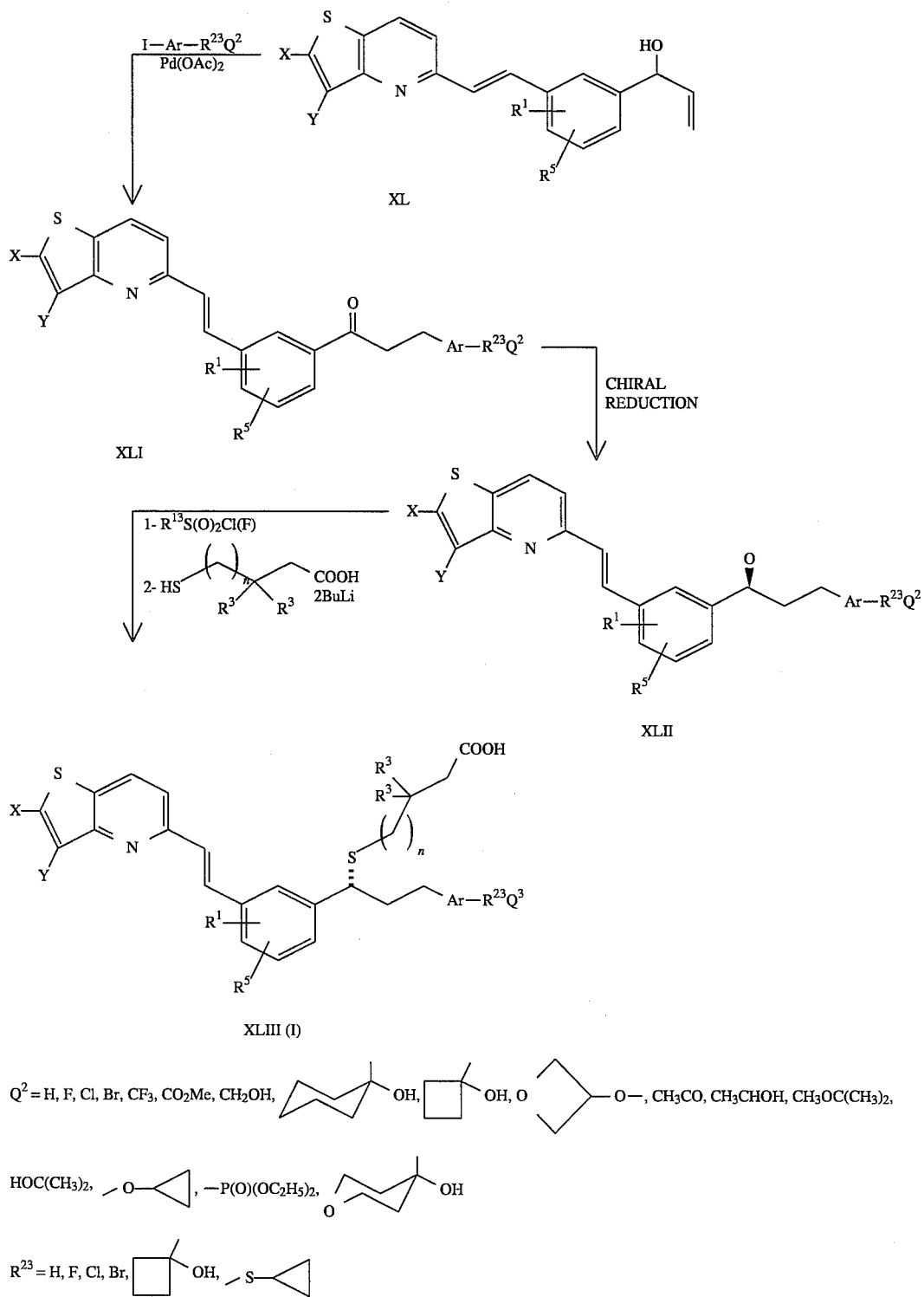
$Q^2$ = H, F, Cl, Br, $CF_3$, $CO_2Me$, $CH_2OH$, [cyclohexyl]-OH, [cyclobutyl]-OH, O-[cyclobutyl]-O—, $CH_3CO$, $CH_3CHOH$, $CH_3OC(CH_3)_2$,
$HOC(CH_3)_2$, /O-[cyclopropyl], —$P(O)(OC_2H_5)_2$, [tetrahydropyranyl]-OH
$R^{23}$ = H, F, Cl, Br, [cyclobutyl]-OH, /S-cyclopropyl
n = 0,1
Ar = trisubstituted benzene, disubstituted thiophene, monosubstituted thiadiazole
$R^3$, $R^3$ = 1, 1-c-Pr or —$C(CH_3)_2$

METHOD N
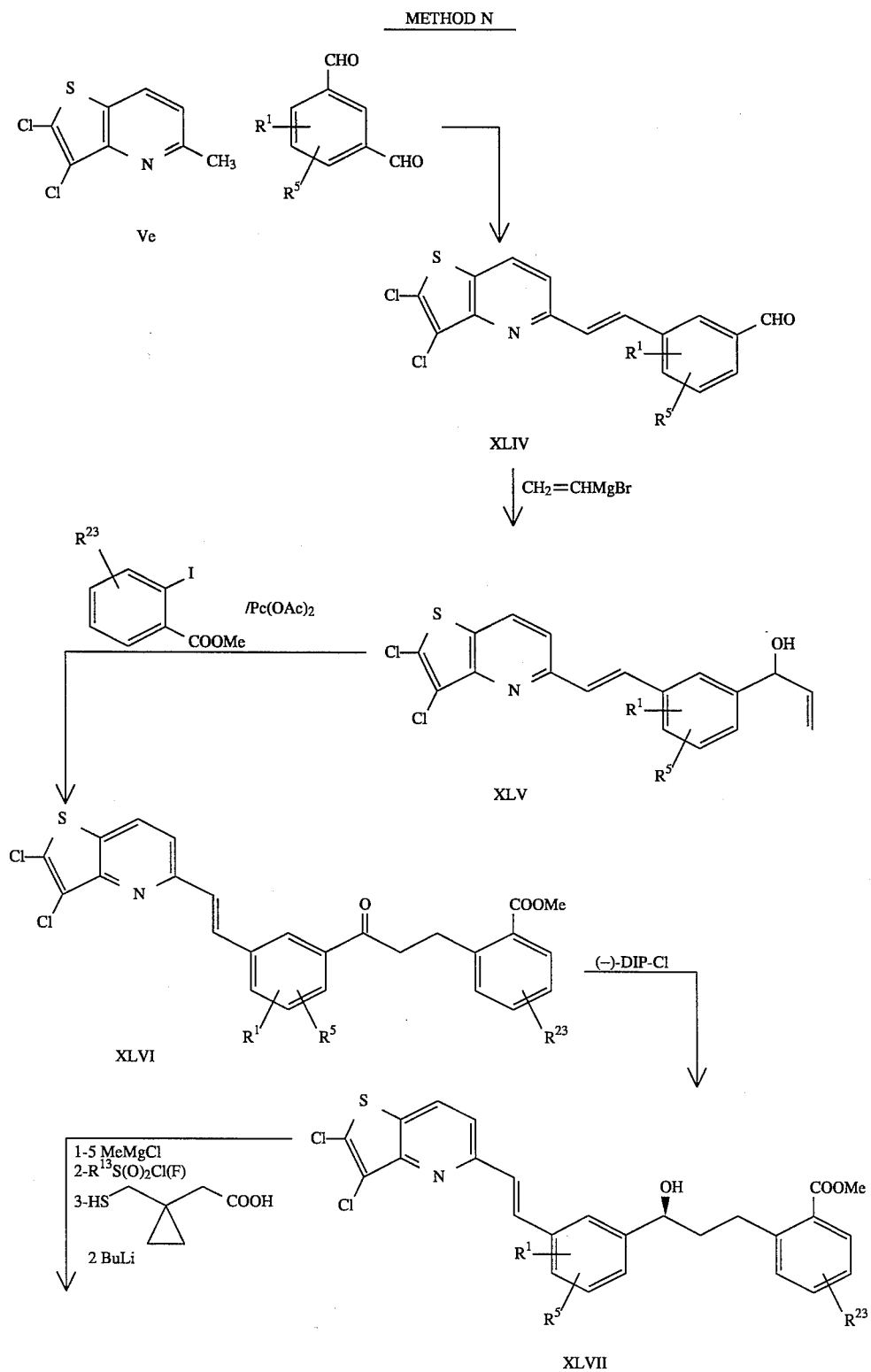

-continued
METHOD N
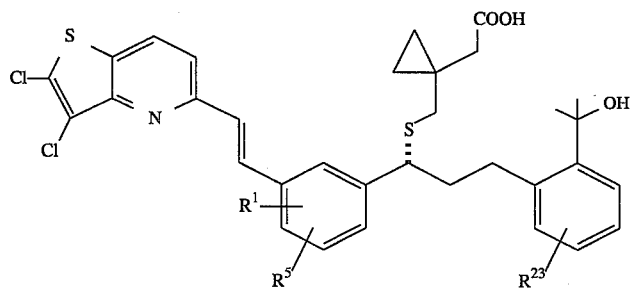
XLVIII (I)
DIP-Cl = B-chlorodiisopinocampheylborane
METHOD O
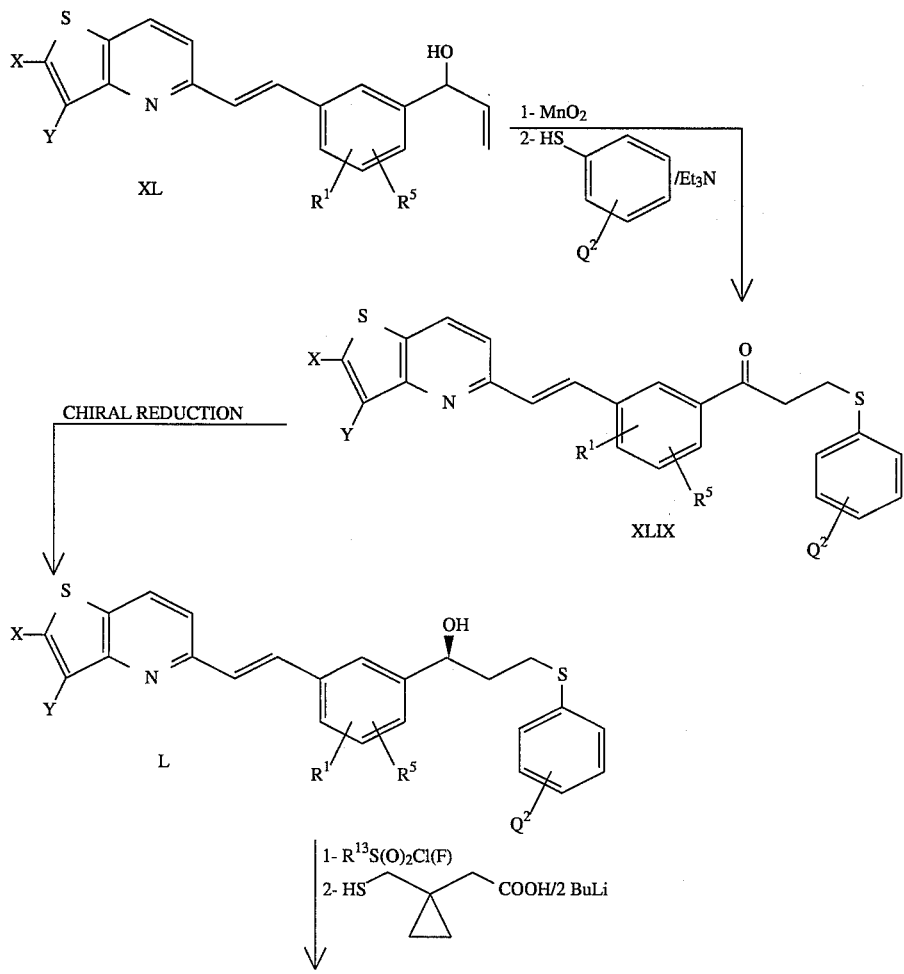

-continued
METHOD O
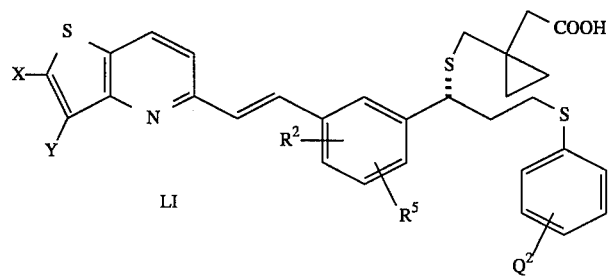
METHOD P
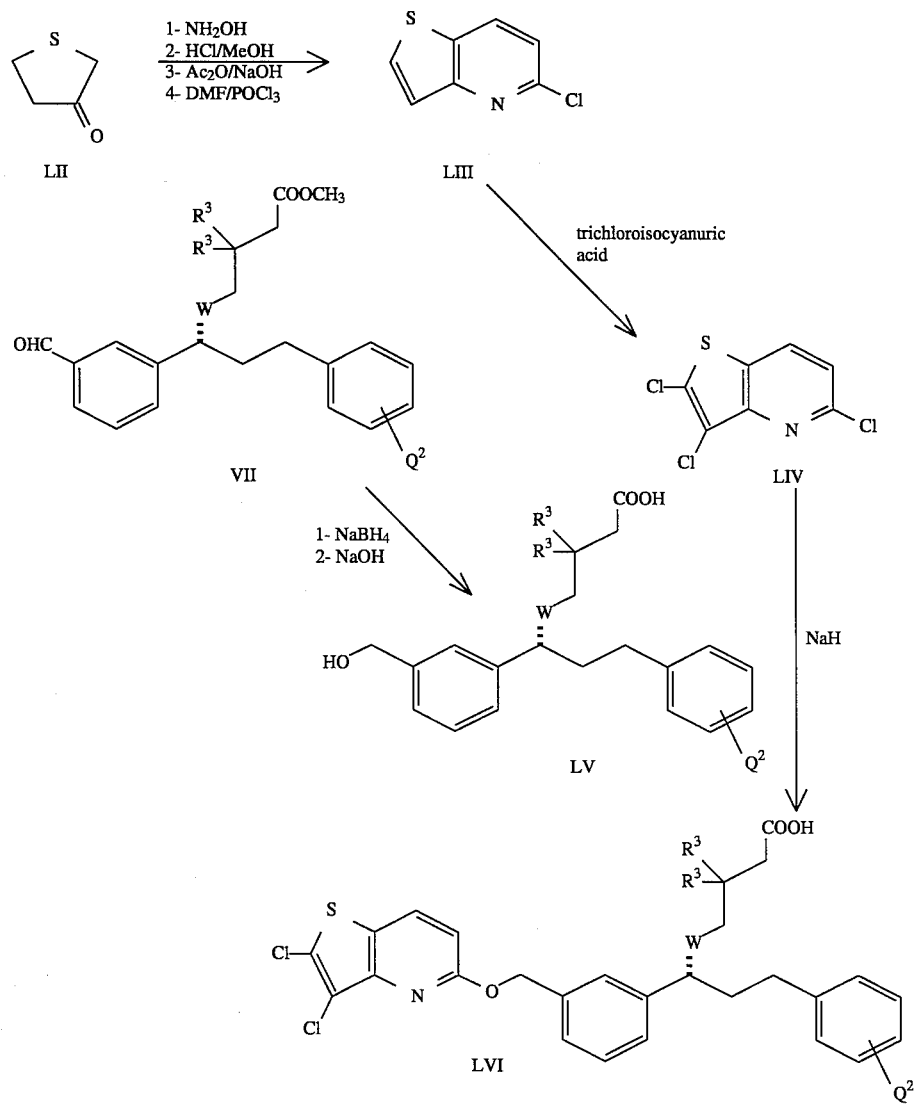

5,472,964
METHOD Q
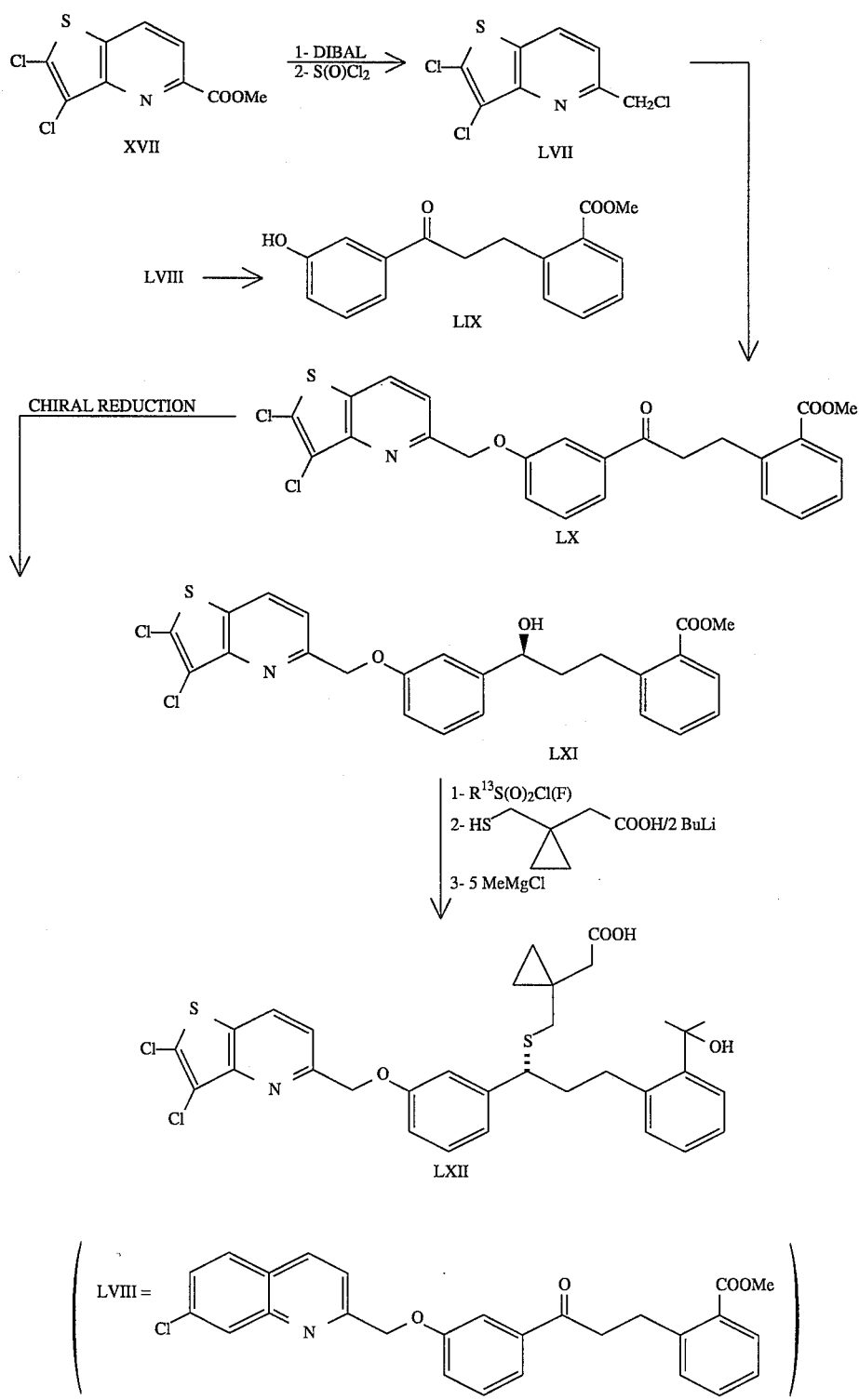

METHOD R

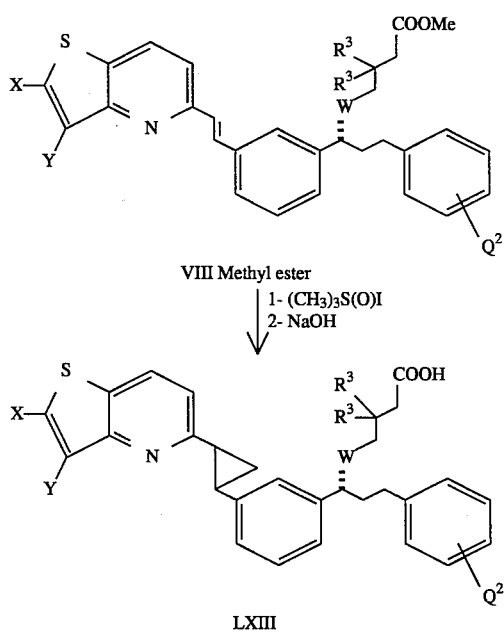

METHOD S

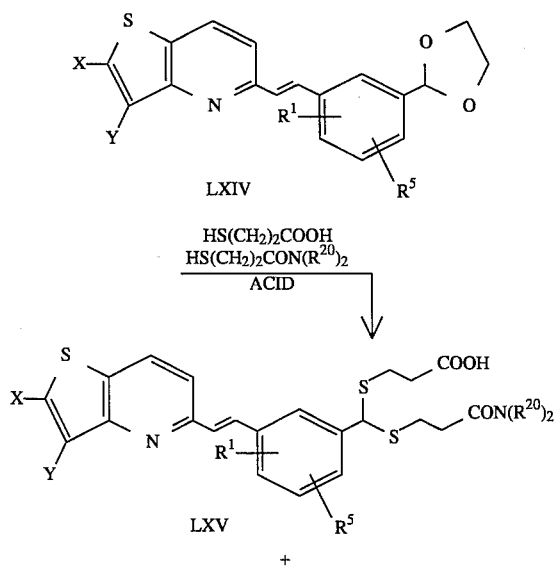

METHOD S -continued

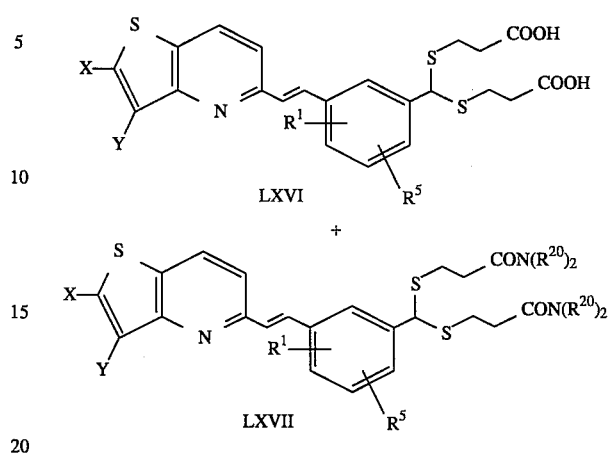

Representative Compounds

Table 1 and Table 2 illustrate compounds which are representative of the present invention. In these tables $Y^1$ stands for $-X^2(C(R^3)_2)_m Z^1(CR^3R^{22})_p Q^1$ and $W^1$ stands for $-X^3(C(R^3)_2)_{m'} Z^2(CR^3R^4)_p Q^2$ from Formula I.

The compounds of Table 1 are of the Formula Id

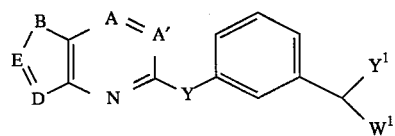

The compounds of Table 2 are of the Formula Ie

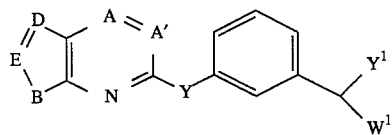

TABLE 1

| EX | A | A' | B | D | E | Y | $Y^1$ | $W^1$ |
|---|---|---|---|---|---|---|---|---|
| 1 | CH | CH | S | CCl | CH | CH=CH | $SCH_2(1,1-c-Pr)CH_2CO_2H$ | $(CH_2)_2(1,2-phe)C(CH_3)_2OH$ |
| 2 | CH | CH | S | CH | CH | CH=CH | $SCH_2(1,1-c-Pr)CH_2CO_2H$ | $(CH_2)_2(1,2-phe)C(CH_3)_2OH$ |
| 3 | CH | CH | S | CBr | CH | CH=CH | $SCH_2(1,1-c-Pr)CH_2CO_2H$ | $(CH_2)_2(1,2-phe)C(CH_3)_2OH$ |
| 4 | CH | CH | S | CCl | CCl | CH=CH | $SCH_2(1,1-c-Pr)CH_2CO_2H$ | $(CH_2)_2(1,2-phe)C(CH_3)_2OH$ |
| 5 | CH | CH | S | CCl | CH | $CH_2CH_2$ | $SCH_2(1,1-c-Pr)CH_2CO_2H$ | $(CH_2)_2(1,2-phe)C(CH_3)_2OH$ |
| 6 | CH | CH | S | CH | CCl | CH=CH | $SCH_2(1,1-c-Pr)CH_2CO_2H$ | $(CH_2)_2(1,2-phe)C(CH_3)_2OH$ |
| 7 | CH | CH | S | CH | CF | CH=CH | $SCH_2(1,1-c-Pr)CH_2CO_2H$ | $(CH_2)_2(1,2-phe)C(CH_3)_2OH$ |
| 8 | CH | CH | S | CF | CF | CH=CH | $SCH_2(1,1-c-Pr)CH_2CO_2H$ | $(CH_2)_2(1,2-phe)C(CH_3)_2OH$ |
| 9 | CH | CH | S | CF | CCl | CH=CH | $SCH_2(1,1-c-Pr)CH_2CO_2H$ | $(CH_2)_2(1,2-phe)C(CH_3)_2OH$ |
| 10 | CH | CH | S | CCl | CF | CH=CH | $SCH_2(1,1-c-Pr)CH_2CO_2H$ | $(CH_2)_2(1,2-phe)C(CH_3)_2OH$ |

5,472,964

TABLE 1-continued

| EX | A | A' | B | D | E | Y | Y¹ | W¹ |
|---|---|---|---|---|---|---|---|---|
| 11 | CH | CH | S | CH | CS(O)₂Ph | CH=CH | SCH₂(1,1-c-Pr)CH₂CO₂H | (CH₂)₂(1,2-phe)C(CH₃)₂OH |
| 12 | CH | CH | O | CCl | CCl | CH=CH | SCH₂(1,1-c-Pr)CH₂CO₂H | (CH₂)₂(1,2-phe)C(CH₃)₂OH |
| 13 | CH | CH | O | CCl | CH | CH=CH | SCH₂(1,1-c-pr)CH₂CO₂H | (CH₂)₂(1,2-phe)C(CH₃)₂OH |
| 14 | CH | CH | S | CCl | CCl | CH=CH | OCH₂(1,1-c-Pr)CH₂CO₂H | (CH₂)₂(1,2-phe)Br |
| 15 | CH | CH | S | CCl | CCl | CH=CH | OCH₂(1,1-c-Pr)CH₂CO₂H | (CH₂)₂(1,2-phe)C(CH₃)₂OH |
| 16 | CH | CH | S | CCl | CCl | CH=CH | SCH₂C(CH₃)₂CH₂COOH | (CH₂)₂(1,4-phe)c-Pr |
| 17 | CH | CH | S | CCl | CF | CH=CH | SCH₂C(CH₃)₂CH₂COOH | (CH₂)₂(1,4-phe)c-Pr |
| 18 | CH | CH | S | CCl | CCl | CH=CH | SCH₂C(CH₃)₂CH₂COOH | (CH₂)₂(1,4-phe)c-Pr |
| 19 | CH | CH | S | CF | CF | CH=CH | SCH₂C(CH₃)₂CH₂COOH | (CH₂)₂(1,4-phe)c-Pr |
| 20 | CH | CH | S | CF | CH | CH=CH | SCH₂(1,1-c-Pr)CH₂CO₂H | (CH₂)₂(1,2-phe)C(CH₃)₂OH |
| 21 | CH | CH | S | CS(O)₂CF₃ | CCl | CH=CH | SCH₂C(CH₃)₂CH₂COOH | (CH₂)₂(1,4-phe)c-Pr |
| 22 | CH | CH | S | CF | CS(O)₂CF₃ | CH=CH | SCH₂C(CH₃)₂CH₂COOH | (CH₂)₂(1,4-phe)c-Pr |
| 23 | CH | CH | S | CCl | CCN | CH=CH | SCH₂C(CH₃)₂CH₂COOH | (CH₂)₂(1,4-phe)c-Pr |
| 24 | CH | CH | S | CBr | CF | CH=CH | SCH₂C(CH₃)₂CH₂COOH | (CH₂)₂(1,4-phe)c-Pr |
| 25 | CH | CH | S | CS(O)₂CF₃ | CCl | CH=CH | SCH₂(1,1-c-Pr)CH₂CO₂H | (CH₂)₂(1,2-phe)C(CH₃)₂OH |
| 26 | CH | CH | S | CF | CS(O)₂CH₃ | CH=CH | SCH₂(1,1-c-Pr)CH₂CO₂H | (CH₂)₂(1,2-phe)C(CH₃)₂OH |
| 27 | CH | CH | S | CCl | CCN | CH=CH | SCH₂(1,1-c-Pr)CH₂CO₂H | (CH₂)₂(1,2-phe)C(CH₃)₂OH |
| 28 | CH | CH | O | CH | CCl | CH=CH | SCH₂(1,1-c-Pr)CH₂CO₂H | (CH₂)₂(1,2-phe)C(CH₃)₂OH |
| 29 | CH | CH | O | CH | CH | CH=CH | SCH₂(1,1-c-Pr)CH₂CO₂H | (CH₂)₂(1,2-phe)C(CH₃)₂OH |
| 30 | CH | CH | S | N | CCF₃ | CH=CH | SCH₂(1,1-c-Pr)CH₂CO₂H | (CH₂)₂(1,2-phe)Br |
| 31 | CH | CH | O | CH | CF | CH=CH | SCH₂(1,1-c-Pr)CH₂COOH | (CH₂)₂(1,2-phe)C(CH₃)₂OH |
| 32 | CH | CH | O | CF | CH | CH=CH | SCH₂(1,1-c-Pr)CH₂CO₂H | (CH₂)₂(1,2-phe)C(CH₃)₂OH |
| 33 | CH | CH | O | CF | CCl | CH=CH | SCH₂(1,1-c-Pr)CH₂CO₂H | (CH₂)₂(1,2-phe)C(CH₃)₂OH |
| 34 | CH | CH | O | CCl | CF | CH=CH | SCH₂(1,1-c-Pr)CH₂CO₂H | (CH₂)₂(1,2-phe)C(CH₃)₂OH |
| 35 | N | CH | S | CH | CF | CH=CH | SCH₂(1,1-c-Pr)CH₂COOH | (CH₂)₂Ph |
| 36 | CH | CH | O | CF | CF | CH=CH | SCH₂(1,1-c-Pr)CH₂CO₂H | (CH₂)₂(1,2-phe)C(CH₃)₂OH |
| 37 | CH | CH | O | CS(O)₂CF₃ | CCl | CH=CH | SCH₂(1,1-c-Pr)CH₂CO₂H | (CH₂)₂(1,2-phe)C(CH₃)₂OH |
| 38 | CH | CH | O | CF | CS(O)₂CF₃ | CH=CH | SCH₂(1,1-c-Pr)CH₂CO₂H | (CH₂)₂(1,2-phe)C(CH₃)₂OH |
| 39 | CH | CH | O | CCl | CCN | CH=CH | SCH₂(1,1-c-Pr)CH₂CO₂H | (CH₂)₂(1,2-phe)C(CH₃)₂OH |
| 40 | CH | CH | O | CBr | CF | CH=CH | SCH₂(1,1-c-Pr)CH₂CO₂H | (CH₂)₂(1,2-phe)C(CH₃)₂OH |
| 41 | CH | CH | S | CH | CH | CH=CH | SCH₂(1,1-c-Pr)CH₂CO₂H | (CH₂)₂(1,2-phe)Br |
| 42 | CH | CH | S | CH | CCl | CH=CH | SCH₂(1,1-c-Pr)CH₂CO₂H | (CH₂)₂(1,2-phe)Br |
| 43 | CH | CH | S | CCl | CH | CH=CH | SCH₂(1,1-c-Pr)CH₂CO₂H | (CH₂)₂(1,2-phe)Br |
| 44 | CH | CH | S | CH | CF | CH=CH | SCH₂(1,1-c-Pr)CH₂CO₂H | (CH₂)₂(1,2-phe)Br |
| 45 | CH | CH | S | CF | CH | CH=CH | SCH₂(1,1-c-Pr)CH₂CO₂H | (CH₂)₂(1,2-phe)Br |
| 46 | CH | CH | S | CF | CCl | CH=CH | SCH₂(1,1-c-Pr)CH₂CO₂H | (CH₂)₂(1,2-phe)Br |
| 47 | CH | CH | S | CCl | CF | CH=CH | SCH₂(1,1-c-Pr)CH₂CO₂H | (CH₂)₂(1,2-phe)Br |
| 48 | CH | CH | S | CCl | CCl | CH=CH | SCH₂(1,1-c-Pr)CH₂CO₂H | (CH₂)₂(1,4-phe)c-Pr |
| 49 | CH | CH | S | CF | CF | CH=CH | SCH₂(1,1-c-Pr)CH₂CO₂H | (CH₂)₂(1,2-phe)Br |
| 50 | CH | CH | S | CS(O)₂CF₃ | CCl | CH=CH | SCH₂(1,1-c-Pr)CH₂CO₂H | (CH₂)₂(1,2-phe)Br |
| 51 | CH | CH | S | CF | CS(O)₂CH₃ | CH=CH | SCH₂(1,1-c-Pr)CH₂CO₂H | (CH₂)₂(1,2-phe)Br |
| 52 | CH | CH | S | CCl | CCN | CH=CH | SCH₂(1,1-c-Pr)CH₂CO₂H | (CH₂)₂(1,2-phe)Br |
| 53 | CH | CH | O | CH | CCl | CH=CH | SCH₂(1,1-c-Pr)CH₂CO₂H | (CH₂)₂(1,2-phe)Br |
| 54 | CH | CH | S | CH | CH | CH=CH | SCH₂(1,1-c-Pr)CH₂CO₂H | (CH₂)₂(1,2-phe)Br |
| 55 | CH | CH | S | CCl | CH | CH=CH | SCH₂(1,1-c-Pr)CH₂CO₂H | (CH₂)₂(1,2-phe)Br |
| 56 | CH | CH | S | CH | CF | CH=CH | SCH₂(1,1-c-Pr)CH₂CO₂H | (CH₂)₂(1,2-phe)Br |
| 57 | CH | CH | S | CF | CH | CH=CH | SCH₂(1,1-c-Pr)CH₂CO₂H | (CH₂)₂(1,2-phe)Br |
| 58 | CH | CH | S | CF | CCl | CH=CH | SCH₂(1,1-c-Pr)CH₂CO₂H | (CH₂)₂(1,2-phe)Br |
| 59 | CH | CH | S | CCl | CF | CH=CH | SCH₂(1,1-c-Pr)CH₂CO₂H | (CH₂)₂(1,2-phe)Br |
| 60 | CH | CH | S | CCl | CCl | CH=CH | SCH₂(1,1-c-Pr)CH₂CO₂H | (CH₂)₂(1,2-phe)Br |
| 61 | CH | CH | S | CF | CF | CH=CH | SCH₂(1,1-c-Pr)CH₂CO₂H | (CH₂)₂(1,2-phe)Br |
| 62 | CH | CH | S | CS(O)₂CF₃ | CCl | CH=CH | SCH₂(1,1-c-Pr)CH₂CO₂H | (CH₂)₂(1,2-phe)Br |
| 63 | CH | CH | S | CF | CS(O)₂CF₃ | CH=CH | SCH₂(1,1-c-Pr)CH₂CO₂H | (CH₂)₂(1,2-phe)Br |
| 64 | CH | CH | S | CCl | CCN | CH=CH | SCH₂(1,1-c-Pr)CH₂CO₂H | (CH₂)₂(1,2-phe)Br |
| 65 | CH | CH | S | CBr | CF | CH=CH | SCH₂(1,1-c-Pr)CH₂CO₂H | (CH₂)₂(1,2-phe)Br |
| 66 | CH | CH | S | CH | CH | CH=CH | SCH₂(1,1-c-Pr)CH₂CO₂H | (CH₂)₂(1,4-phe)(1,1-c-Bu)OH |
| 67 | CH | CH | S | CH | CCl | CH=CH | SCH₂(1,1-c-Pr)CH₂CO₂H | (CH₂)₂(1,4-phe)(1,1-c-Bu)OH |
| 68 | CH | CH | S | CCl | CH | CH=CH | SCH₂(1,1-c-Pr)CH₂CO₂H | (CH₂)₂(1,4-phe)(1,1-c-Bu)OH |
| 69 | CH | CH | S | CH | CF | CH=CH | SCH₂(1,1-c-Pr)CH₂CO₂H | (CH₂)₂(1,4-phe)(1,1-c-Bu)OH |
| 70 | CH | CH | S | CF | CH | CH=CH | SCH₂(1,1-c-Pr)CH₂CO₂H | (CH₂)₂(1,4-phe)(1,1-c-Bu)OH |
| 71 | CH | CH | S | CF | CCl | CH=CH | SCH₂(1,1-c-Pr)CH₂CO₂H | (CH₂)₂(1,4-phe)(1,1-c-Bu)OH |
| 72 | CH | CH | S | CCl | CF | CH=CH | SCH₂(1,1-c-Pr)CH₂CO₂H | (CH₂)₂(1,4-phe)(1,1-c-Bu)OH |
| 73 | CH | CH | S | CCl | CCl | CH=CH | SCH₂(1,1-c-Pr)CH₂CO₂H | (CH₂)₂(1,4-phe)(1,1-c-Bu)OH |
| 74 | CH | CH | S | CF | CF | CH=CH | SCH₂(1,1-c-Pr)CH₂CO₂H | (CH₂)₂(1,4-phe)(1,1-c-Bu)OH |
| 75 | CH | CH | S | CS(O)₂CF₃ | CCl | CH=CH | SCH₂(1,1-c-Pr)CH₂CO₂H | (CH₂)₂(1,4-phe)(1,1-c-Bu)OH |
| 76 | CH | CH | S | CF | CS(O)₂CH₃ | CH=CH | SCH₂(1,1-c-Pr)CH₂CO₂H | (CH₂)₂(1,4-phe)(1,1-c-Bu)OH |
| 77 | CH | CH | S | CCl | CCN | CH=CH | SCH₂(1,1-c-Pr)CH₂CO₂H | (CH₂)₂(1,4-phe)(1,1-c-Bu)OH |
| 78 | CH | CH | O | CH | CCl | CH=CH | SCH₂(1,1-c-Pr)CH₂CO₂H | (CH₂)₂(1,4-phe)(1,1-c-Bu)OH |
| 79 | CH | CH | S | CH | CH | CH=CH | SCH₂(1,1-c-Pr)CH₂CO₂H | (CH₂)₂(1,4-phe)(1,1-c-Bu)OH |
| 80 | CH | CH | S | CCl | CH | CH=CH | SCH₂(1,1-c-Pr)CH₂CO₂H | (CH₂)₂(1,4-phe)(1,1-c-Bu)OH |
| 81 | CH | CH | S | CH | CF | CH=CH | SCH₂(1,1-c-Pr)CH₂CO₂H | (CH₂)₂(1,4-phe)(1,1-c-Bu)OH |
| 82 | CH | CH | S | CF | CH | CH=CH | SCH₂(1,1-c-Pr)CH₂CO₂H | (CH₂)₂(1,4-phe)(1,1-c-Bu)OH |
| 83 | CH | CH | S | CF | CCl | CH=CH | SCH₂(1,1-c-Pr)CH₂CO₂H | (CH₂)₂(1,4-phe)(1,1-c-Bu)OH |
| 84 | CH | CH | S | CCl | CF | CH=CH | SCH₂(1,1-c-Pr)CH₂CO₂H | (CH₂)₂(1,4-phe)(1,1-c-Bu)OH |
| 85 | CH | CH | S | CCl | CCl | CH=CH | SCH₂(1,1-c-Pr)CH₂CO₂H | (CH₂)₂(1,4-phe)(1,1-c-Bu)OH |
| 86 | CH | CH | S | CF | CF | CH=CH | SCH₂(1,1-c-Pr)CH₂CO₂H | (CH₂)₂(1,4-phe)(1,1-c-Bu)OH |
| 87 | CH | CH | S | CS(O)₂CF₃ | CCl | CH=CH | SCH₂(1,1-c-Pr)CH₂CO₂H | (CH₂)₂(1,4-phe)(1,1-c-Bu)OH |

TABLE 1-continued

| EX | A | A' | B | D | E | Y | Y¹ | W¹ |
|---|---|---|---|---|---|---|---|---|
| 88 | CH | CH | S | CF | CS(O)₂CF₃ | CH=CH | SCH₂(1,1-c-Pr)CH₂CO₂H | (CH₂)₂(1,4-phe)(1,1-c-Bu)OH |
| 89 | CH | CH | S | CCl | CCN | CH=CH | SCH₂(1,1-c-Pr)CH₂CO₂H | (CH₂)₂(1,4-phe)(1,1-c-Bu)OH |
| 90 | CH | CH | S | CBr | CF | CH=CH | SCH₂(1,1-c-Pr)CH₂CO₂H | (CH₂)₂(1,4-phe)(1,1-c-Bu)OH |
| 91 | CH | CH | S | CH | CH | CH=CH | SCH₂C(CH₃)₂CH₂COOH | (CH₂)₂(1,4-phe)c-Pr |
| 92 | CH | CH | S | CH | CCl | CH=CH | SCH₂C(CH₃)₂CH₂COOH | (CH₂)₂(1,4-phe)c-Pr |
| 93 | CH | CH | S | CCl | CH | CH=CH | SCH₂C(CH₃)₂CH₂COOH | (CH₂)₂(1,4-phe)c-Pr |
| 94 | CH | CH | S | CH | CF | CH=CH | SCH₂C(CH₃)₂CH₂COOH | (CH₂)₂(1,4-phe)c-Pr |
| 95 | CH | CH | S | CF | CH | CH=CH | SCH₂C(CH₃)₂CH₂COOH | (CH₂)₂(1,4-phe)c-Pr |
| 96 | CH | CH | S | CF | CCl | CH=CH | SCH₂C(CH₃)₂CH₂COOH | (CH₂)₂(1,4-phe)c-Pr |
| 97 | CH | CH | S | CCl | CF | CH=CH | SCH₂C(CH₃)₂CH₂COOH | (CH₂)₂(1,4-phe)c-Pr |
| 98 | CH | CH | S | CCl | CCl | CH=CH | OCH₂(1,1-c-Pr)CH₂CO₂H | (CH₂)₂(1,2-phe)Br |
| 99 | CH | CH | S | CF | CF | CH=CH | SCH₂C(CH₃)₂CH₂COOH | (CH₂)₂(1,4-phe)c-Pr |
| 100 | CH | CH | S | CS(O)₂CF₃ | CCl | CH=CH | SCH₂C(CH₃)₂CH₂COOH | (CH₂)₂(1,4-phe)c-Pr |
| 101 | CH | CH | S | CF | CS(O)₂CF₃ | CH=CH | SCH₂C(CH₃)₂CH₂COOH | (CH₂)₂(1,4-phe)c-Pr |
| 102 | CH | CH | S | CCl | CCN | CH=CH | SCH₂C(CH₃)₂CH₂COOH | (CH₂)₂(1,4-phe)c-Pr |
| 103 | CH | CH | O | CH | CCl | CH=CH | SCH₂C(CH₃)₂CH₂COOH | (CH₂)₂(1,4-phe)c-Pr |
| 104 | CH | CH | S | CH | CH | CH=CH | SCH₂C(CH₃)₂CH₂COOH | (CH₂)₂(1,4-phe)c-Pr |
| 105 | CH | CH | S | CCl | CH | CH=CH | SCH₂C(CH₃)₂CH₂COOH | (CH₂)₂(1,4-phe)c-Pr |
| 106 | CH | CH | S | CH | CF | CH=CH | SCH₂C(CH₃)₂CH₂COOH | (CH₂)₂(1,4-phe)c-Pr |
| 107 | CH | CH | S | CF | CH | CH=CH | SCH₂C(CH₃)₂CH₂COOH | (CH₂)₂(1,4-phe)c-Pr |
| 108 | CH | CH | S | CF | CCl | CH=CH | SCH₂C(CH₃)₂CH₂COOH | (CH₂)₂(1,4-phe)c-Pr |
| 124 | CH | CH | S | CCl | CCl | CH=CH | SCH₂(1,1-c-Pr)CH₂CO₂H | (CH₂)₂(1,3-phe)-O-c-Pr |
| 125 | CH | CH | S | CCl | CCl | CH=CH | SCH₂(1,1-c-Pr)CH₂CO₂H | (CH₂)₂(1,4-phe)-I |
| 126 | CH | CH | S | CCl | CCl | CH=CH | SCH₂(1,1-c-Pr)CH₂CO₂H | (CH₂)₂(1,4-phe)C((CH₂)₃OH |
| 127 | CH | CH | S | CCl | CCl | CH=CH | SCH₂(1,1-c-pr)CH₂CO₂H | (CH₂)₂(1,4-phe)Br |
| 128 | CH | CH | S | CCl | CCl | CH=CH | SCH₂(1,1-c-pr)CH₂CO₂H | (CH₂)₂(1,4-phe)Oc-pr |
| 129 | CH | CH | S | CCl | CCl | CH=CH | SCH₂C(CH₃)₂CH₂COOH | (CH₂)₂(1,4-phe)Br |
| 130 | CH | CH | S | CCl | CCl | CH=CH | SCH₂(1,1-c-Pr)CH₂CO₂H | (CH₂)₂(2,5-thi)Cl |
| 131 | CH | CH | S | CCl | CCl | CH=CH | S(1,1-c-pr)CH₂CO₂H | (CH₂)₂(1,4-phe)Br |
| 132 | CH | CH | S | CCl | CCl | CH=CH | SCH₂(1,1-c-pr)CH₂CO₂H | (CH₂)₂(1,4-phe)C(CH₂)₂OCH₃ |
| 133 | CH | CH | S | CCl | CCl | CH=CH | SCH₂(1,1-c-pr)CH₂CO₂H | (CH₂)₂(1,4-phe)F |
| 134 | CH | CH | S | CCl | CCl | CH=CH | SCH₂(1,1-c-pr)CH₂CO₂H | (CH₂)₂(1,4-phe)C(CH₃)₂OH |
| 135 | CH | CH | S | CCl | CCl | CH=CH | SCH₂(1,1-c-pr)CH₂CO₂H | (CH₂)₂(1,4-phe)Cl |
| 136 | CH | CH | O | CCl | CCl | CH=CH | SCH₂(1,1-c-pr)CH₂CO₂H | (CH₂)₂(2-th) |
| 137 | CH | CH | S | CCl | CCl | CH=CH | SCH₂(1,1-c-pr)CH₂CO₂H | (CH₂)₂(1,4-phe)CF₃ |
| 138 | CH | CH | S | CCl | CCl | CH=CH | SCH₂(1,1-c-pr)CH₂CO₂H | (CH₂)₂(1,3-phe)(1,1-c-Bu)OH |
| 139 | CH | CH | S | CCl | CCl | CH=CH | SCH₂(1,1-c-pr)CH₂CO₂H | (CH₂)₂(1,4-phe)SO₂-c-pr |
| 140 | CH | CH | S | CCl | CCl | CH=CH | SCH₂(1,1-c-pr)CH₂CO₂H | (CH₂)₂(1,2-phe)(1,1-c-Bu)OH |
| 141 | CH | CH | S | CCl | CBr | CH=CH | SCH₂(1,1-c-pr)CH₂CO₂H | (CH₂)₂(1,2-phe)C(CH₃)₂OH |
| 142 | CH | CH | S | CCl | CBr | CH=CH | SCH₂(1,1-c-pr)CH₂CO₂H | (CH₂)₂(1,4-phe)C(CH₃)₂OH |
| 143 | CH | CH | S | CCl | CCl | CH=CH | SCH₂(1,1-c-pr)CH₂CO₂H | (CH₂)₂(4-F-1,2-phe)C(CH₃)₂OH |
| 144 | CH | CH | S | CCl | CCl | CH=CH | SCH₂(1,1-c-pr)CH₂CO₂H | (CH₂)₂(4-Cl-1,2-phe)C(CH₃)₂OH |
| 145 | CH | CH | S | CCl | CCl | CH=CH | SCH₂(1,1-c-pr)CH₂CO₂H | (CH₂)₂(4-Cl-1,2-phe)(1,1-c-Bu)OH |
| 146 | CH | CH | S | CCl | CCl | CH=CH | SCH₂(1,1-c-pr)CH₂CO₂H | (CH₂)₂(1,2-phe)CH₂OH |
| 147 | CH | CH | S | CCl | CCl | CH=CH | SCH₂(1,1-c-pr)CH₂CO₂H | (CH₂)₂(1,2-phe)CO₂CH₃ |
| 148 | CH | CH | S | CCl | CCl | CH=CH | SCH₂(1,1-c-pr)CH₂CO₂H | (CH₂)₂(1,2-phe)(1,1-c-Hex)OH |
| 149 | CH | CH | S | CCl | CCl | CH=CH | SCH₂(1,1-c-pr)CH₂CO₂H | (CH₂)₂(4-Cl-1,2-phe)CH₂OH |
| 150 | CH | CH | S | CCl | CCl | CH=CH | SCH₂(1,1-c-pr)CH₂CO₂H | (CH₂)₂Ph |
| 151 | CH | CH | S | CCl | CBr | CH=CH | SCH₂(1,1-c-pr)CH₂CO₂H | (CH₂)₂(1,2-phe)C(CH₃)₂OH |
| 152 | CH | CH | S | CCl | CCl | CH=CH | SCH₂(1,1-c-pr)CH₂CO₂H | (CH₂)₂(6-Br-1,2-phe)CH₂OH |
| 153 | CH | CH | S | CCl | CCl | CH=CH | SCH₂(1,1-c-pr)CH₂CO₂H | (CH₂)₂(1,2-phe)COCH₃ |
| 154 | CH | CH | S | CCl | CCl | CH=CH | SCH₂(1,1-c-pr)CH₂CO₂H | (CH₂)₂TdzH |
| 155 | CH | CH | S | CCl | CCl | CH=CH | SCH₂(1,1-c-pr)CH₂CO₂H | (CH₂)₂(1,2-phe)CH(OH)CH₃ |
| 156 | CH | CH | S | CCl | CCl | CH=CH | SCH₂(1,1-c-pr)CH₂CO₂H | (CH₂)₂(1,2-phe)C(CH₃)₂OCH₃ |
| 157 | CH | CH | S | CCl | CCl | CH=CH | SCH₂(1,1-c-pr)CH₂CO₂H | (CH₂)₂(6-Br-1,2-phe)C(CH₃)₂OH |
| 158 | CH | CH | S | CCl | CBr | CH=CH | SCH₂(1,1-c-pr)CH₂CO₂H | (CH₂)₂(1,3-Phe)Br |
| 159 | CH | CH | S | CCl | CBr | CH=CH | S(1,1-c-pr)CH₂CO₂H | (CH₂)₂(1,2-Phe)Br |
| 160 | CH | CH | S | CCl | CCl | CH=CH | SCH₂(1,1-c-pr)CH₂CO₂H | (CH₂)₂(1,3-Phe)F |
| 161 | CH | CH | S | CCl | CBr | CH=CH | SCH₂(1,1-c-pr)CH₂CO₂H | (CH₂)₂(1,3-Phe)Cl |
| 162 | CH | CH | S | CCl | CF | CH=CH | S(1,1-c-pr)CH₂CO₂H | (CH₂)₂(1,3-Phe)Cl |
| 163 | CH | CH | S | CCl | CF | CH=CH | SCH₂(1,1-c-pr)CH₂CO₂H | (CH₂)₂(1,3-phe)C(CH₃)₂OH |
| 164 | CH | CH | S | CCl | CCl | CH=CH | SCH₂(1,1-c-pr)CH₂CO₂H | (CH₂)₂(5-((1,1-c-Bu)OH)-1,3-phe)-(1,1-c-Bu)OH |
| 165 | CH | CH | S | CCl | CCl | CH=CH | SCH₂(1,1-c-pr)CH₂CO₂H | (CH₂)₂(1,3-phe)F |
| 166 | CH | CH | S | CCl | CCl | CH=CH | SCH₂(1,1-c-pr)CH₂CO₂H | (CH₂)₂Thz |
| 167 | CH | CH | S | CCl | CCl | CH=CH | SCH₂(1,1-c-pr)CH₂CO₂H | (CH₂)₂(1,2-phe)CF₃ |
| 168 | CH | CH | S | CCl | CCl | CH=CH | SCH₂(1,1-c-pr)CH₂CO₂H | (CH₂)₂(1,2-phe)O-OX |
| 169 | CH | CH | S | CCl | CCl | CH=CH | SCH₂(1,1-c-pr)CH₂CO₂H | (CH₂)₂(1,2-phe)(4-OH-T4P) |
| 170 | CH | CH | S | CCl | CCl | CH=CH | SCH₂(1,1-c-pr)CH₂CO₂H | (CH₂)₂(1,3-phe)P(O)(OCH₂CH₃)₂ |
| 171 | CH | CH | S | CCl | CCl | CH=CH | SCH₂(1,1-c-pr)CH₂CO₂H | (CH₂)₂(1,4-phe)S-c-Pr |
| 172 | CH | CH | S | CCl | CF | CH=CH | SCH₂(1,1-c-pr)CH₂CO₂H | (CH₂)₂(1,4-phe)C(CH₃)₂OH |
| 173 | CH | CH | S | CCl | CF | CH=CH | SCH₂(1,1-c-pr)CH₂CO₂H | (CH₂)₂(1,3-phe)C(CH₃)₂OH |
| 174 | CH | CH | S | CCl | CH | O—CH₂ | SCH₂(1,1-c-pr)CH₂CO₂H | (CH₂)₂(1,2-phe)C(CH₃)₂OH |
| 175 | CH | CH | S | CH | CH | O—CH₂ | SCH₂(1,1-c-pr)CH₂CO₂H | (CH₂)₂(1,2-phe)C(CH₃)₂OH |
| 176 | CH | CH | S | CH | CCl | O—CH₂ | SCH₂(1,1-c-pr)CH₂CO₂H | (CH₂)₂(1,2-phe)C(CH₃)₂OH |
| 177 | CH | CH | S | CH | CF | O—CH₂ | SCH₂(1,1-c-pr)CH₂CO₂H | (CH₂)₂(1,2-phe)C(CH₃)₂OH |
| 178 | CH | CH | S | CCl | CCl | O—CH₂ | SCH₂(1,1-c-pr)CH₂CO₂H | (CH₂)₂(1,2-phe)C(CH₃)₂OH |

TABLE 1-continued

| EX | A | A' | B | D | E | Y | $Y^1$ | $W^1$ |
|---|---|---|---|---|---|---|---|---|
| 179 | CH | CH | S | CH | CBr | O—$CH_2$ | $SCH_2$(1,1-c-pr)$CH_2CO_2H$ | $(CH_2)_2$(1,2-phe)$C(CH_3)_2OH$ |
| 180 | CH | CH | S | CF | CH | O—$CH_2$ | $SCH_2$(1,1-c-pr)$CH_2CO_2H$ | $(CH_2)_2$(1,2-phe)$C(CH_3)_2OH$ |
| 181 | CH | CH | S | CCl | CH | $CH_2$—O | $SCH_2$(1,1-c-pr)$CH_2CO_2H$ | $(CH_2)_2$(1,2-phe)$C(CH_3)_2OH$ |
| 182 | CH | CH | S | CH | CH | $CH_2$—O | $SCH_2$(1,1-c-pr)$CH_2CO_2H$ | $(CH_2)_2$(1,2-phe)$C(CH_3)_2OH$ |
| 183 | CH | CH | S | CH | CCl | $CH_2$—O | $SCH_2$(1,1-c-pr)$CH_2CO_2H$ | $(CH_2)_2$(1,2-phe)$C(CH_3)_2OH$ |
| 184 | CH | CH | S | CH | CF | $CH_2$—O | $SCH_2$(1,1-c-pr)$CH_2CO_2H$ | $(CH_2)_2$(1,2-phe)$C(CH_3)_2OH$ |
| 185 | CH | CH | S | CCl | CCl | $CH_2$—O | $SCH_2$(1,1-c-pr)$CH_2CO_2H$ | $(CH_2)_2$(1,2-phe)$C(CH_3)_2OH$ |
| 186 | CH | CH | S | CH | CBr | $CH_2$—O | $SCH_2$(1,1-c-pr)$CH_2CO_2H$ | $(CH_2)_2$(1,2-phe)$C(CH_3)_2OH$ |
| 187 | CH | CH | S | CF | CH | $CH_2$—O | $SCH_2$(1,1-c-pr)$CH_2CO_2H$ | $(CH_2)_2$(1,2-phe)$C(CH_3)_2OH$ |
| 188 | CH | CH | S | CCl | CH | CH=CH | $S(CH_2)_2CO_2H$ | $S(CH_2)_2CON(CH_3)_2$ |
| 189 | CH | CH | S | CH | CH | CH=CH | $S(CH_2)_2CO_2H$ | $S(CH_2)_2CON(CH_3)_2$ |
| 190 | CH | CH | S | CH | CCl | CH=CH | $S(CH_2)_2CO_2H$ | $S(CH_2)_2CON(CH_3)_2$ |
| 191 | CH | CH | S | CH | CF | CH=CH | $S(CH_2)_2CO_2H$ | $S(CH_2)_2CON(CH_3)_2$ |
| 192 | CH | CH | S | CCl | CCl | CH=CH | $S(CH_2)_2CO_2H$ | $S(CH_2)_2CON(CH_3)_2$ |
| 193 | CH | CH | S | CH | CPr | CH=CH | $S(CH_2)_2CO_2H$ | $S(CH_2)_2CON(CH_3)_2$ |
| 194 | CH | CH | O | CH | CH | CH=CH | $S(CH_2)_2CO_2H$ | $S(CH_2)_2CON(CH_3)_2$ |
| 195 | CH | CH | O | CCl | CH | CH=CH | $S(CH_2)_2CO_2H$ | $S(CH_2)_2CON(CH_3)_2$ |
| 196 | CH | CH | O | CBr | CH | CH=CH | $S(CH_2)_2CO_2H$ | $S(CH_2)_2CON(CH_3)_2$ |
| 197 | CH | CH | S | CF | CF | O—$CH_2$ | $SCH_2$(1,1-c-Pr)$CH_2CO_2H$ | $(CH_2)_2$(1,2-phe)$C(CH_3)_2OH$ |
| 198 | CH | CH | S | CF | CF | $CH_2$—O | $SCH_2$(1,1-c-Pr)$CH_2CO_2H$ | $(CH_2)_2$(1,2-phe)$C(CH_3)_2OH$ |
| 199 | CH | CH | S | CF | CF | CH=CH | $S(CH_2)_2CO_2H$ | $S(CH_2)_2CON(CH_3)_2$ |
| 200 | CH | CH | S | CCl | CH | 1,2-c-Pr | $SCH_2$(1,1-c-Pr)$CH_2CO_2H$ | $(CH_2)_2$(1,2-phe)$C(CH_3)_2OH$ |
| 201 | CH | CH | S | CH | CH | 1,2-c-Pr | $SCH_2$(1,1-c-Pr)$CH_2CO_2H$ | $(CH_2)_2$(1,2-phe)$C(CH_3)_2OH$ |
| 202 | CH | CH | S | CH | CCl | 1,2-c-Pr | $SCH_2$(1,1-c-Pr)$CH_2CO_2H$ | $(CH_2)_2$(1,2-phe)$C(CH_3)_2OH$ |
| 203 | CH | CH | S | CH | CF | 1,2-c-Pr | $SCH_2$(1,1-c-Pr)$CH_2CO_2H$ | $(CH_2)_2$(1,2-phe)$C(CH_3)_2OH$ |
| 204 | CH | CH | S | CBr | CH | 1,2-c-Pr | $SCH_2$(1,1-c-Pr)$CH_2CO_2H$ | $(CH_2)_2$(1,2-phe)$C(CH_3)_2OH$ |
| 205 | CH | CH | O | CH | CH | 1,2-c-Pr | $SCH_2$(1,1-c-Pr)$CH_2CO_2H$ | $(CH_2)_2$(1,2-phe)$C(CH_3)_2OH$ |
| 206 | CH | CH | O | CCl | CH | 1,2-c-Pr | $SCH_2$(1,1-c-Pr)$CH_2CO_2H$ | $(CH_2)_2$(1,2-phe)$C(CH_3)_2OH$ |
| 207 | CH | CH | O | CBr | CH | 1,2-c-Pr | $SCH_2$(1,1-c-Pr)$CH_2CO_2H$ | $(CH_2)_2$(1,2-phe)$C(CH_3)_2OH$ |
| 208 | CH | CH | S | CH | CH | CH=CH | $SCH_2$(1,1-c-Pr)$CH_2CO_2H$ | $(CH_2)_2S$(1,4-phe)F |
| 209 | CH | CH | S | CCl | CH | CH=CH | $SCH_2$(1,1-c-Pr)$CH_2CO_2H$ | $(CH_2)_2S$(1,4-phe)F |
| 210 | CH | CH | S | CH | CCl | CH=CH | $SCH_2$(1,1-c-Pr)$CH_2CO_2H$ | $(CH_2)_2S$(1,4-phe)F |
| 211 | CH | CH | S | CH | CF | CH=CH | $SCH_2$(1,1-c-Pr)$CH_2CO_2H$ | $(CH_2)_2S$(1,4-phe)F |
| 212 | CH | CH | S | CH | CH | CH=CH | $SCH_2$(1,1-c-Pr)$CH_2CO_2H$ | $(CH_2)_2S$(1,4-phe)F |
| 213 | CH | CH | S | CCl | CH | CH=CH | $SCH_2$(1,1-c-Pr)$CH_2CO_2H$ | $(CH_2)_2S$(1,4-phe)F |
| 214 | CH | CH | S | CBr | CH | CH=CH | $SCH_2$(1,1-c-Pr)$CH_2CO_2H$ | $(CH_2)_2S$(1,4-phe)F |
| 215 | CH | CH | S | CH | CH | CH=CH | $SCH_2$(1,1-c-Pr)$CH_2CO_2H$ | $(CH_2)_2S$(1,4-phe)Cl |
| 216 | CH | CH | S | CCl | CH | CH=CH | $SCH_2$(1,1-c-Pr)$CH_2CO_2H$ | $(CH_2)_2S$(1,4-phe)Cl |
| 217 | CH | CH | S | CBr | CH | CH=CH | $SCH_2$(1,1-c-Pr)$CH_2CO_2H$ | $(CH_2)_2S$(1,4-phe)Cl |
| 218 | CH | CH | S | CCl | CCl | 1,2-c-Pr | $SCH_2$(1,1-c-Pr)$CH_2CO_2H$ | $(CH_2)_2$(1,2phe)$C(CH_3)_2OH$ |
| 219 | CH | CH | S | CCl | CCl | CH=CH | $SCH_2$(1,1-c-Pr)$CH_2CO_2H$ | $(CH_2)_2S$(1,4-phe)F |

TABLE 2

| EX | A | A' | B | D | E | Y | $Y^1$ | $W^1$ |
|---|---|---|---|---|---|---|---|---|
| 109 | CH | CH | S | N | CH | CH=CH | $SCH_2$(1,1-c-Pr)$CH_2CO_2H$ | $(CH_2)_2$(1,2-phe)$C(CH_3)_2OH$ |
| 110 | CH | CH | S | N | $CCF_3$ | CH=CH | $SCH_2$(1,1-c-Pr)$CH_2CO_2H$ | $(CH_2)_2$(1,2-phe)$C(CH_3)_2OH$ |
| 111 | CH | CH | S | N | Cc-Pr | CH=CH | $SCH_2$(1,1-c-Pr)$CH_2CO_2H$ | $(CH_2)_2$(1,2-phe)$C(CH_3)_2OH$ |
| 112 | CH | CH | S | CH | CCl | CH=CH | $SCH_2$(1,1-c-Pr)$CH_2CO_2H$ | $(CH_2)_2$(1,2-phe)$C(CH_3)_2OH$ |
| 113 | CH | CH | S | CCl | CH | CH=CH | $SCH_2$(1,1-c-Pr)$CH_2CO_2H$ | $(CH_2)_2$(1,2-phe)$C(CH_3)_2OH$ |
| 114 | CH | CH | S | CH | CF | CH=CH | $SCH_2$(1,1-c-Pr)$CH_2CO_2H$ | $(CH_2)_2$(1,2-phe)$C(CH_3)_2OH$ |
| 115 | CH | CH | S | CF | CH | CH=CH | $SCH_2$(1,1-c-Pr)$CH_2CO_2H$ | $(CH_2)_2$(1,2-phe)$C(CH_3)_2OH$ |
| 116 | CH | CH | S | CCl | CCl | CH=CH | $SCH_2$(1,1-c-Pr)$CH_2CO_2H$ | $(CH_2)_2$(1,2-phe)$C(CH_3)_2OH$ |
| 117 | CH | CH | S | CF | CF | CH=CH | $SCH_2$(1,1-c-Pr)$CH_2CO_2H$ | $(CH_2)_2$(1,2-phe)$C(CH_3)_2OH$ |
| 118 | CH | CH | S | $CS(O)_2CF_3$ | CCl | CH=CH | $SCH_2$(1,1-c-Pr)$CH_2CO_2H$ | $(CH_2)_2$(1,2-phe)$C(CH_3)_2OH$ |
| 119 | CH | CH | S | CCN | CCl | CH=CH | $SCH_2$(1,1-c-Pr)$CH_2CO_2H$ | $(CH_2)_2$(1,2-phe)$C(CH_3)_2OH$ |
| 120 | N | CH | S | N | CH | CH=CH | $SCH_2$(1,1-c-Pr)$CH_2CO_2H$ | $(CH_2)_2$(1,4-phe)-O-c-Pr |
| 121 | N | CH | S | N | $CF_3$ | CH=CH | $SCH_2$(1,1-c-Pr)$CH_2CO_2H$ | $(CH_2)_2$(1,4-phe)-O-c-Pr |
| 122 | H | N | S | N | CH | CH=CH | $SCH_2$(1,1-c-Pr)$CH_2CO_2H$ | $(CH_2)_2$(1,4-phe)c-Pr |
| 123 | CH | CH | S | N | $CCH_3$ | CH=CH | $SCH_2$(1,1-c-Pr)$CH_2CO_2H$ | $(CH_2)_2$(1,2-phe)$C(CH_3)_2OH$ |

Assays for Determining Biological Activity

The leukotriene antagonist properties of the compounds of the present invention are evaluated using the following assays:

1. [$^3$H]$LTD_4$ Receptor Binding Assay in DMSO-differentiated U937 Cells (a human monocytic cell line);
2. [$^3$H]$LTD_4$ Receptor Binding on Guinea Pig Lung Membranes;
3. [$^3$H]$LTD_4$ Receptor Binding on Human Lung Membranes;
4. In Vitro Guinea Pig Trachea; and
5. In Vivo Assays in Anesthetized Guinea Pigs.

The above assays are described by T. R. Jones et al., Can. J. Physiol. Pharmacol. 1991, 69, 1847–1854.

Asthmatic Rat Assay

Rats are obtained from an inbred line of asthmatic rats. Both female (190–250 g) and male (260–400 g) rats are used.

Egg albumin (EA), grade V, crystallized and lyophilized, is obtained from Sigma Chemical Co., St. Louis. Aluminum hydroxide is obtained from the Regis Chemical Company, Chicago. Methysergide bimaleate is supplied by Sandoz Ltd., Basel.

The challenge and subsequent respiratory recordings are carried out in a clear plastic box with internal dimensions 10×6×4 inches. The top of the box is removable; in use, it is held firmly in place by four clamps and an airtight seal is maintained by a soft rubber gasket. Through the center of each end of the chamber a DeVilbiss nebulizer (No. 40) is inserted via an airtight seal and each end of the box also has an outlet. A Fleisch No. 0000 pneumotachograph is inserted into one end of the box and coupled to a Grass volumetric pressure transducer (PT5-A) which is then connected to a Buxco Electronics preamplifier (Buxco Electronics Inc., Sharon, Conn.). The preamplifier is connected to a Beckman Type R Dynograph and to a Buxco computer consisting of waveform analyzer, Data Acquisition Logger with special software. While aerosolizing the antigen, the outlets are open and the pneumotachograph is isolated from the chamber. The outlets are closed and the pneumotachograph and the chamber are connected during the recording of the respiratory patterns. For challenge, 2 mL of a 3% solution of antigen in saline is placed into each nebulizer and the aerosol is generated with air from a small Potter diaphragm pump operating at 10 psi and a flow of 8 liters/minute.

Rats are sensitized by injecting (subcutaneously) 1 mL of a suspension containing 1 mg EA and 200 mg aluminum hydroxide in saline. They are used between days 12 and 24 post sensitization. In order to eliminate the serotonin component of the response, rats are pretreated intravenously 5 minutes prior to aerosol challenge with 3.0 μg/kg of methysergide. Rats are then exposed to an aerosol of 3% EA in saline for exactly 1 minute, then their respiratory profiles are recorded for a further 30 minutes. The duration of continuous dyspnea is measured by the Buxco computer.

Compounds are generally administered either orally 2–4 hours prior to challenge or intravenously 2 minutes prior to challenge. They are either dissolved in saline or 1% methocel or suspended in 1% methocel. The volume injected is 1 mL/kg (intravenously) or 10 mL/kg (orally). Prior to oral treatment rats are starved overnight. The activity of compounds is determined in terms of their ability to decrease the duration of antigen-induced dyspnea in comparison with a group of vehicle-treated controls. Usually, a compound is evaluated at a series of doses and an $ED_{50}$ is determined. This is defined as the dose (mg/kg) which would inhibit the duration of symptoms by 50%.

Pulmonary Mechanics in Trained Conscious Squirrel Monkeys

The test procedure involves placing trained squirrel monkeys in chairs in aerosol exposure chambers. For control purposes, pulmonary mechanics measurements of respiratory parameters are recorded for a period of about 30 minutes to establish each monkey's normal control values for that day. For oral administration, compounds are dissolved or suspended in a 1% methocel solution (methylcellulose, 65HG, 400 cps) and given in a volume of 1 mL/kg body weight. For aerosol administration of compounds, a DeVilbiss ultrasonic nebulizer is utilized. Pretreatment periods vary from 5 minutes to 4 hours before the monkeys are challenged with aerosol doses of either leukotriene $D_4$ ($LTD_4$) or *Ascaris suum* antigen; 1:25 dilution.

Following challenge, each minute of data is calculated by computer as a percent change from control values for each respiratory parameter including airway resistance ($R_L$) and dynamic compliance ($C_{dyn}$). The results for each test compound are subsequently obtained for a minimum period of 60 minutes post challenge which are then compared to previously obtained historical baseline control values for that monkey. In addition, the overall values for 60 minutes post-challenge for each monkey (historical baseline values and test values) are averaged separately and are used to calculate the overall percent inhibition of $LTD_4$ or Ascaris antigen response by the test compound. For statistical analysis, paired t-test is used. (References: McFarlane, C. S. et al., *Prostaglandins,* 28, 173–182 (1984) and McFarlane, C. S. et al., Agents Actions, 22, 63–68 (1987).)

Prevention of Induced Bronchoconstriction in Allergic Sheep

A. Rationale: Certain allergic sheep with known sensitivity to a specific antigen (*Ascaris suum*) respond to inhalation challenge with acute and late bronchial responses. The time course of both the acute and the late bronchial responses approximates the time course observed in asthmatics and the pharmacological modification of both responses is similar to that found in man. The effects of antigen in these sheep are largely observed in the large airways and are conveniently monitored as changes in lung resistance or specific lung resistance.

B. Methods: Animal Preparation: Adult sheep with a mean weight of 35 kg (range, 18 to 50 kg) are used. All animals used meet two criteria: a) they have a natural cutaneous reaction to 1:1,000 or 1:10,000 dilutions of *Ascaris suum* extract (Greer Diagnostics, Lenois, N.C.); and b) they have previously responded to inhalation challenge with *Ascaris suum* with both an acute bronchoconstriction and a late bronchial obstruction (W. M. Abraham et al., *Am. Rev. Resp. Dis.,* 128, 839–44 (1983)).

Measurement of Airway Mechanics: The unsedated sheep are restrained in a cart in the prone position with their heads immobilized. After topical anesthesia of the nasal passages with 2% lidocaine solution, a balloon catheter is advanced through one nostril into the lower esophagus. The animals are then intubated with a cuffed endotracheal tube through the other nostril using a flexible fiberoptic bronchoscope as a guide. Pleural pressure is estimated with the esophageal balloon catheter (filled with one mL of air), which is positioned such that inspiration produces a negative pressure deflection with clearly discernible cardiogenic oscillations. Lateral pressure in the trachea is measured with a sidehole catheter (inner dimension, 2.5 mm) advanced through and positioned distal to the tip of the nasotracheal tube. Transpulmonary pressure, the difference between tracheal pressure and pleural pressure, is measured with a differential pressure transducer (DP45; Validyne Corp., Northridge, Calif.). For the measurement of pulmonary resistance ($R_L$), the maximal end of the nasotrachel tube is connected to a pneumotachograph (Fleisch, Dyna Sciences, Blue Bell, Pa.). The signals of flow and transpulmonary pressure are recorded on an oscilloscope (Model DR-12; Electronics for Medicine, White Plains, N.Y.) which is linked to a PDP-11 Digital computer (Digital Equipment Corp., Maynard, Mass.) for on-line calculation of $R_L$ from transpulmonary pressure, respiratory volume obtained by integration and flow. Analysis of 10–15 breaths is used for the determination of $R_L$. Thoracic gas volume ($V_{tg}$) is measured in a body plethysmograph, to obtain specific pulmonary resistance ($SR_L = R_L \cdot V_{tg}$).

Aerosol Delivery Systems: Aerosols of *Ascaris suum* extract (1:20) are generated using a disposable medicalnebulizer (Raindrop®, Puritan Bennett), which produces an aerosol with a mass median aerodynamic diameter of 6.2 μM (geometric standard deviation, 2.1) as determined by an electric size analyzer (Model 3030; Thermal Systems, St.

Paul, Minn.). The output from the nebulizer is directed into a plastic t-piece, one end of which is attached to the nasotracheal tube, the other end of which is conected to the inspiratory part of a Harvard respirator. The aerosol is delivered at a tidal volume of 500 mL of a rate of 20 per minute. Thus, each sheep receives an equivalent dose of antigen in both placebo and drug trials.

Experimental Protocol: Prior to antigen challenge baseline measurements of $SR_L$ are obtained, infusion of the test compound is started 1 hr prior to challenge, the measurement of $SR_L$ repeated and then the sheep undergoes inhalation challenge with Ascaris suum antigen. Measurements of $SR_L$ are obtained immediately after antigen challenge and at 1, 2, 3, 4, 5, 6, 6.5, 7, 7.5, and 8 hrs after antigen challange. Placebo and drug tests are separated by at least 14 days. In a further study, sheep are given a bolus dose of the test compound followed by an infusion of the test compound for 0.5–1 hr prior to Ascaris challenge and for 8 hrs after Ascaris as described above.

Statistical Analysis: A Kruskal-Wallis one way ANOVA test is used to compare the acute immediate responses to antigen and the peak late response in the controls and the drug treated animals.

The invention will now be illustrated by the following nonlimiting examples in which, unless stated otherwise:

(i) all operations were carried out at room or ambient temperature, that is, at a temperature in the range 18°–25° C.;

(ii) evaporation of solvent was carried out using a rotary evaporator under reduced pressure (600–4000 pascals: 4.5–30 mm Hg) with a bath temperature of up to 60° C.;

(iii) the course of reactions was followed by thin layer chromatography (TLC) and reaction times are given for illustration only;

(iv) melting points are uncorrected and 'd' indicates decomposition; the melting points given are those obtained for the materials prepared as described; polymorphism may result in isolation of materials with different melting points in some preparations;

(v) the structure and purity of all final products were assured by at least one of the following techniques: TLC, mass spectrometry, nuclear magnetic resonance (NMR) spectrometry, or microanalytical data;

(vi) yields are given for illustration only;

(vii) when given, NMR data are in the form of delta ($\delta$) values for major diagnostic protons, given in parts per million (ppm) relative to tetramethylsilane (TMS) as internal standard, determined at 300 MHz or 400 MHz using the indicated solvent; conventional abbreviations used for signal shape are: s. singlet; d. doublet; t. triplet; m. multiplet; br. broad; etc.: in addition "Ar" signifies an aromatic signal;

(viii) chemical symbols have their usual meanings; the following abbreviations have also been used: v (volume), w (weight), b.p. (boiling point), m.p. (melting point), L (liter(s)), mL (milliliters), g (gram(s)), mg (milligram(s)), mol (moles), mmol (millimoles), eq. (equivalent(s)).

EXAMPLE 1

Sodium 1-(((1(R)-(3-(2-(3-chlorothieno[3,2-b]pyridin-5-yl) ethenyl)phenyl)-3-(2-(1-hydroxy-1-methylethyl)phenyl) propyl)thio)methyl)cyclopropaneacetate Step 1: 3-Amino-2-formylthiophene To a cold (0° C.) stirring solution of lithium aluminum hydride in THF (380 mL, 1M) was added methyl 3-amino-2-thiophenecarboxylate (30 g, 190 mmol) in small portions over a period of 30 min. The resulting mixture was stirred at 0° C. for 1 hr. Water (15 mL) was added dropwise very slowly followed by slow addition of aqueous NaOH (15 mL, 3.5 N). Then more water (43 mL) and THF (300 mL) was added. The mixture was stirred well for 30 min then filtered through celite. The celite was washed with more THF. The filtrate was concentrated to an oil which was redissolved in 2 L of EtOAc. The EtOAc solution was dried over anhydrous $MgSO_4$ and filtered. The resulting solution of the crude 3-amino-2-hydroxymethylthiophene was then treated with $MnO_2$ (100 g). The mixture was stirred at r.t. for 20 hr. and then filtered through celite. The filtrate was evaporated to give 23.3 g (65%) of the title compound.

$^1$H NMR ($CDCl_3$) $\delta$6.10 (2H, br s), 6.54 (1H, d, J=5 Hz), 7.48 (1H, d, J=5 Hz), 9.57 (1H, s).

Step 2: Thieno[3,2-b]pyridine-5-carboxylic acid

To a solution of 3-amino-2-formylthiophene (10 g, 78 mmol) in EtOH (50 mL) was added a mixture of aqueous NaOH (50 mL, 5%) and sodium pyruvate (17.16 g, 156 mmol). The mixture was heated to 60° C. for 2 hr. The mixture was cooled and washed with $Et_2O$: EtOAc 1:1 and then acidified with 1N HCl to pH 3 at 0° C. The mixture was filtered and the solid was air dried to give 10 g (71%) of the title compound.

$^1$H NMR ($CD_3SOCD_3$) $\delta$7.68 (1H, d, J=5.5 Hz), 8.00 (1H, d, J=8.4 Hz), 8.28 (1H, d, J=5.5 Hz), 8.65 (1H, d, J=8.4 Hz)

Step 3: 3-Chlorothieno[3.2-b]pyridine-5-carboxylic acid

To a solution of $Ag_2SO_4$ (6.96 g, 22.3 mmol) in conc. $H_2SO_4$ (60 mL) at 100° C. was added thieno[3,2-b]pyridine-5-carboxylic acid (4 g, 22.3 mmol). $Cl_2$ was bubbled through the rapid stirring mixture over a period of 2 hr. The mixture was cooled and then poured into ice (250 mL). The AgCl precipitated and was filtered. The filtrate was diluted with water (500 mL) and allowed to crystallized at 0° C. overnight. The product was filtered and air dried to give 3.04 g (64%) of the title compound.

$^1$H NMR ($CD_3SOCD_3$) $\delta$8.10 (1H, d, J=8.4 Hz), 8.39 (1H, s), 8.72 (1H, d, J=8.4 Hz).

Step 4: 3-Chloro-5-(chloromethyl)thieno[3,2-b]pyridine

The acid of Step 3 was esterified with excess diazomethane. To a solution of the corresponding ester (1.2 g, 5.6 mmol) in THF (10 mL) at −78° C. was added DIBAL (9.36 mL, 1.5M). The resulting mixture was stirred at 0° C. for 1 hr. Methanol (0.5 mL) was added followed by the addition of HCl (10 mL, 0.5M). The mixture was extracted with EtOAc. The organic extract was dried over anhyd. $MgSO_4$ and concentrated in vacuo. Chromatography of the crude product on silica gel (eluted with 40% EtOAc in hexane) gave 900 mg (100%) of the corresponding alcohol. The alcohol was then refluxed in $S(O)Cl_2$ (5 mL) for 5 min. The excess reagent was removed under vacuum. $NaHCO_3$ was then added. The mixture was extracted with EtOAc. Concentration of the dried (anhyd. $MgSO_4$) organic extract gave 1.2 g (98%) of the title compound.

Step 5: ((3-Chlorothieno[3,2-b]pyridin-5-yl)methyl)triphenylphosphonium chloride To a solution of 3-chloro-5-(chloromethyl)thieno[3,2-b]-pyridine (1.2 g, 5.5 mmol) in $CH_3CN$ (20 mL) was added $P(Ph)_3$ (2.88 g, 11 mmol). The mixture was refluxed for 20 hr. and was then evaporated to dryness. $Et_2O$ (8 mL) was added. The mixture was stirred vigorously and the crystalline salt was filtered and washed with more $Et_2O$ to give. 2.1 g (81%) of the title compound.

$^1$H NMR ($CD_3SOCD_3$) $\delta$5.75 (2H, d, J=18.75 Hz), 7.48 (1H, d, J=7.5 Hz), 7.65–8.00 (15H, m), 8.25 (1H, s), 8.55 (1H, d, J=7.5 Hz).

Step 6: 1,1-Cyclopropanedimethanol cyclic sulfite

To a solution of $BH_3$·THF complex (1M in THF, 262 mL) was added diethyl 1,1-cyclopropanedicarboxylate (25 g, 134 mmol) at 25° C. under $N_2$. The solution was heated at reflux for 6 hr., cooled to r.t., and MeOH (300 mL) was cautiously added. The solution was stirred for 1 hr. and then concentrated to an oil. The crude diol was dissolved in $CH_2Cl_2$ (234 mL) and $SOCl_2$ (15.9 g, 134 mmol) was added dropwise over a period of 15 min at 25° C. After stirring for another 15 min, the mixture was washed with aqueous $NaHCO_3$. The organic extract was dried over $Na_2SO_4$, filtered and concentrated to give quantitatively the title compound as a white solid.

Step 7: 1-(Hydroxymethyl,)cyclopropaneacetonitrile

To a solution of the cyclic sulfite product of Step 6 (14.7 g, 99 mmol) in DMF (83 mL) was added NaCN (9.74 g, 199 mmol). The mixture was heated to 90° C. for 20 hr. Upon cooling, EtOAc (400 mL) was added and the solution was washed with saturated $NaHCO_3$ solution (55 mL), $H_2O$ (4×55 mL), saturated NaCl solution, and dried over $Na_2SO_4$. The solution was concentrated to give 7.1 g (65%) of the title compound.

Step 8: 1-(Acetylthiomethyl)cyclopropaneacetonitrile

To a solution of the alcohol of Step 7 (42 g, 378 mmol) in dry $CH_2Cl_2$ (450 mL) at −30° C. was added $Et_3N$ (103.7 mL, 741 mmol) followed by $CH_3S(O)_2Cl$ (43.3 mL, 562 mmol) dropwise. The mixture was warmed to 25° C., washed with $NaHCO_3$, dried over $Na_2SO_4$, and concentrated in vacuo to give the corresponding mesylate. The mesylate was then dissolved in DMF (450 mL) and cooled to 0° C. Potassium thioacetate (55.4 g, 485 mmol) was added, and the mixture was stirred at 25° C. for 18 hr. EtOAc (1.5 L) was added, the solution was washed with $NaHCO_3$, dried over $Na_2SO_4$, and concentrated in vacuo to give 45 g (70%) of the title compound.

Step 9: Methyl 1-(mercaptomethyl)cyclopropaneacetate

To a solution of the nitrile of Step 8 (45 g, 266 mmol) in MeOH (1.36 L) was added $H_2O$(84 mL) and conc. $H_2SO_4$ (168 mL). The mixture was heated to reflux for 20 hr, cooled to 25° C., $H_2O$(1 L) was added and the product was extracted with $CH_2Cl_2$ (2×1.5 L). The organic extract was washed with $H_2O$ and dried over $Na_2SO_4$. Concentration of the organic solution gave 36 g (93%) of the title compound.

Step 10: 3-(((2-Tetrahydropyranyl)oxy)methyl) benzaldehyde

Isophthalaldehyde (150 g, 1.1 mole) was dissolved in THF (1 L) and EtOH (1 L) at 0° C. $NaBH_4$ (11.0 g, 291 mmol) was added portionwise and the mixture stirred 1 hr at 0° C. Addition of 25% aq. $NH_4OAc$ and extraction with EtOAc (2×) followed by purification by flash chromatography (20%→40% EtOAc in hexanes) yielded 60 g of 3-(hydroxymethyl)-benzaldehyde.

This alcohol (0.44 mole) was dissolved in $CH_2Cl_2$ (500 mL). DHP (50 g, 59 mole) and PTSA (1 g, 5 mmol) were added and the mixture was stirred overnight at r.t. After concentration in vacuo, the residue was purified by flash chromatography (5%→15% EtOAc in toluene) to give 85 g of the title compound.

Step 11: 1-(3-(((2-Tetrahydropyranyl)oxy)methyl)phenyl)-2-propen-1-ol

To the aldehyde of Step 10 (85 g, 386 mmol) in toluene (1 L) at 0° C. was slowly added vinyl magnesium bromide in $Et_2O$ (450 mL, 1M, 450 mmol) over a 30 minute period. After stirring for 1 hr at 0° C., the reaction mixture was quenched with 25% aq. $NH_4OAc$ and extracted with EtOAc (3×). Evaporation and purification by flash chromatography (15%→25% EtOAc in toluene) yielded 82 g (86%) of the title compound.

Step 12: Ethyl 2-(3-(3-(((2-tetrahydropyranyl)oxy)methyl)phenyl)-3-oxopropyl)benzoate The allylic alcohol of Step 11 (24.8 g, 100 mmol) and ethyl 2-bromobenzoate (25.2 g, 110 mmol) were dissolved in DMF (200 mL). LiCl (4.2 g, 100 mmol), $LiOAc·2H_2O$(25.5 g, 250 mmol) and n-$BU_4N+Cl−$(55 g, 200 mmol) were added and the resulting mixture was degassed three times. $Pd(OAc)_2$ (1 g) was then added and the mixture was degassed three more times before heating it at 100° C. with stirring for 1 hr. After cooling to r.t., the reaction mixture was poured onto $H_2O$(600 mL), 10% aq. $NaHCO_3$ (200 mL) and $Et_2O$. The crude product was extracted with $Et_2O$(2×), washed with $H_2O$ and brine, and dried over $Na_2SO_4$ before concentrating in vacuo. Purification on a short silica gel column (20% EtOAc in hexanes) gave 34 g (86%) of the title compound.

$^1$H NMR ($CD_3COCD_3$): δ8.02 (1H, bs), 7.92 (1H, d), 7.88 (1H, d), 7.65 (1H, d), 7.50 (3H, m), 7.32 (1H, bt), 4.8 (1H, d), 4.70 (1H, bs), 4.54 (1H, d), 4.3 (2H, q), 3.82 (1H, m), 3.50 (1H, m), 3.35 (2H, m), 1.9–1.45 (8H, m), 1.32 (3H, t).

Step 13: Ethyl 2-(3(S)-hydroxy-3-(3-(((2-2(-tetrahydropyranyl)oxy)-methyl)phenyl)propyl) benzoate The ketoester of Step 12 (24.8 g, 62.5 mmol) was dissolved in THF (230 mL) and cooled to −45° C. A THF (15 mL) solution of tetrahydro-1-methyl-3,3-diphenyl-1H,3H-pyrrolo[1,2-c][1,3,2]oxazoborole.borane adduct (J. Org. Chem. 56, 751 (1991), 4.55 g, 15.6 mmol) was added dropwise and the resulting mixture was stirred 20 minutes at −45° C. To this solution, 1.0M borane in THF (62.5 mL, 62.5 mmol) was added dropwise over 30 minutes. The reaction mixture was stirred 1 hr. at −45° C. followed by another 2 hrs. with slow warming to −20° C. After cooling the solution to −40° C., it was poured onto 25% aq. $NH_4OAc$ (425 mL) and 1.0M diethanolamine (40 mL) at 0° C. and stirred vigorously for 20 minutes. The title compound was extracted with EtOAc (3×), dried over $MgSO_4$ and concentrated under reduced pressure. The crude oil was purified by flash chromatography (25% to 50% EtOAc in hexanes) to yield 22.6 g (91%) of the product as an oil.

$[\alpha]_D^{25}$=−32.6° (c=3, $CHCl_3$)

Step 14: 1(S)-(3-(((2-Tetrahydropyranyl)oxy)methyl)phenyl)-3-( 2-(1-hydroxy-1-methylethyl)phenyl)propan)-1-ol Anhydrous $CeCl_3$ (17.25 g, 70 mmol) was refluxed for 2.5 hours in THF (200 mL) using a Dean-Stark trap filled with molecular sieves to remove $H_2O$. The ivory suspension was cooled to −5° C. and MeMgCl (114 mL, 3M in THF, 340 mmol) was added dropwise while keeping the internal temperature between −10° C. and 0° C. The grey suspension was stirred 2 hrs before slowly adding to it the hydroxyester of Step 13 (27.1 g, 68 mmol) as a THF solution (200 mL) via a cannula. The resulting mixture was stirred 1.5 hr. at or below 0° C., and then slowly poured onto ice cold 1M HOAc (1 L) and EtOAc (500 mL) and stirred for 30 minutes. After adjusting the pH to 6–7, the crude compound was extracted with EtOAc (2×) and the combined organic phases were washed with saturated aq. $NaHCO_3$ followed with brine. Purification on a short silica gel column (30% to 50% EtOAc in hexanes) yielded 24.5 g (95%) of the title compound.

Step 15: Methyl 1-(((1(R)-(3-(((2-tetrahydropyranyl)oxy)methyl)phenyl)-3-(2-(1-hydroxy-1-methylethyl)phenyl)propyl)thio)methyl)cyclopropaneacetate The diol of Step 14 (17.9 g, 46.6 mmol) was dissolved in $CH_3CN$ (40 mL) and DMF (10 mL) and cooled to −42° C. under nitrogen. Diisopropyl-ethylamine (8.5 mL, 48.9 mmol) was added followed by methanesulfonyl chloride (3.6 mL, 46.6 mmol) dropwise. The solution was stirred 1.5 hr with a mechanical stirring while maintaining the temperature between −42° and −35° C.; then it was cooled to −45° C. The thiol of Step 9 (7.84 g, 48.9 mmol) was added followed by dropwise addition of DMF (15 mL). Potassium tert-butoxide in THF (56 mL, 1.75M, 97.9 mmol) was added to the reaction mixture over 20 minutes using a syringe pump. Stirring was continued for 5 hr with slow warming from −35° C. to −22° C., giving a very thick translucid gel. The reaction was quenched with saturated aq. NH$_4$Cl (250 mL) and EtOAc (300 mL). The product was extracted with EtOAc, washed with H$_2$O and brine, and dried over MgSO$_4$. Purification by flash chromatography (20% to 30% EtOAc in hexanes) gave 16.8 g (68%) of the title compound.

Step 16: Methyl 1-(((1(R)-(3-(hydroxymethyl)phenyl)-3-(2-(1 -hydroxy-1-methylethyl)phenyl)propyl)thi-o)methyl)cyclopropaneacetate To the hydroxy ester from Step 15 (9.02 g, 17.1 mol) in anhydrous MeOH (60 mL) under nitrogen was added pyridine (50 μL) followed by PPTS (1.1 g, 4.3 mmol). The reaction mixture was stirred 3.5 hr at 55° C., then at r.t. overnight before concentrating in vacuo. The residue was diluted with EtOAc (500 mL) and washed with H$_2$O, saturated aq. NaHCO$_3$, NaH$_2$PO$_4$ buffer (pH=4.5) and with brine. After drying over MgSO$_4$ and evaporation of the solvents, the residue was purified by flash chromatography (40% to 60% EtOAc in hexanes) giving 6.85 g (91%) of the title compound.

$^1$H NMR (CD$_3$COCD$_3$): δ7.41 (2H, m), 7.27 (3H, m), 7.09 (3H, m), 4.63 (2H, d), 4.19 (1H, t), 3.95 (1H, t), 3.88 (1H, s), 3.57 (3H, s), 3.1 (1H, ddd), 2.8 (1H, ddd), 2.5 (2H, s), 2.4 (2H, d), 2.17 (2H, m), 1.52 (6H, s), 0.52–0.35 (4H, m).

Step 17: Methyl 1-(((1(R)-(3-formylphenyl)-3-(2-(1-hydroxy-1 -methylethyl)phenyl)propyl)thi-o)methyl)cyclopropaneacetate To the dihydroxy ester from Step 16 (6.8 g, 15.4 mmol) in EtOAc (150 mL) at 50° C. was added MnO$_2$ (6.7 g, 76.8 mmol). After stirring for 30 minutes at 50° C. more MnO$_2$ (6.7 g) was added, and 30 minutes later, a third portion of MnO$_2$ (6.7 g) was added. An hour later, the warm reaction mixture was filtered through celite and the cake was washed with additional EtOAc. Evaporation of the solvents gave the desired aldehyde 5.62 g (83%).

$^1$H NMR (CD$_3$COCD$_3$): δ10.4 (1H, s), 7.9 (1H, bs), 7.8 (2H, m), 7.58 (1H, t), 7.38 (1H, bd), 7.1 (3H, m), 4.1 (1H, t), 3.54 (3H, s), 3.13 (1H, ddd), 2.85 (1H, ddd), 2.51 (2H, s), 2.49 (2H, d), 2.2 (2H, m), 1.51 (6H, s), 0.52–0.32 (4H, m).

Step 18: Methyl 1-(((1(R)-(3-(2-(3-chlorothieno[3,2-b]pyridin-5 -yl)-ethenyl)phenyl)-3-(2-(1-hydroxy-1-methylethyl)phenyl)propyl)-thio)methyl)cyclopropaneacetate To a suspension of the phosphonium salt from Step 5 (409 mg, 0.85 mmol) in dry THF (5 mL) at −78° C. was added a solution of potassium ten-butoxide (0.716 mL, 1M solution in THF). The mixture was warmed to room temperature for 30 min, and then cooled to −78° C. before adding the aldehyde from Step 17 (300 mg, 0.7 mmol). The mixture was stirred at −78° C. for 30 min, warmed to 0° C. for 15 min. Aqueous NH$_4$OAc was added and the mixture was extracted with EtOAc. The organic extract was washed with brine, dried over MgSO$_4$, and concentrated to an oil. Chromatography of the crude oil on silica gel (eluted with 20% EtOAc in hexane) gave 420 mg (98%) of the title compound.

$^1$H NMR (CD$_3$COCD$_3$): δ0.35–0.55 (4H, m), 1.55 (6H, s), 2.1–2.3 (2H, m), 2.45 (2H, d, J=7.5 Hz), 2.55(2H, s), 2.8–2.95 (1H, m), 3.1–3.25 (1H, m), 3.55 (3H, s), 4.05 (1H, t, J=7.5 Hz), 7.05–7.15 (4H, m), 7.4 (2H, d, J=3.75 Hz), 7.5 (1H, d, J=15 Hz), 7.6 (1H, m), 7.75 (1H, d, J=7.5 Hz), 7.8 (1H, s), 7.85–7.95 (1H, d, J=15 Hz), 8.05 (1H, s), 8.45 (1H, d, J=8 Hz).

Step 19: Sodium 1-(((1(R)-(3-(2-(3-chlorothieno[3,2-b]pyridin-5 -yl)-ethenyl)phenyl)-3-(2-(1-hydroxymethylethyl)phenyl)propyl)-thio)methyl)cyclopropaneacetate To a solution of the ester of Step 18 in THF (1 mL) and MeOH (1 mL) was added aqueous NaOH (1N, 1.4 mL). The mixture was stirred at 25° C. for 20 hr. NH$_4$Cl was added and the mixture was extracted with EtOAc. The organic extract was washed with brine, dried over MgSO$_4$, and concentrated to an oil. Chromatography of the crude oil on silica gel (eluted with 20% EtOAc/5% HOAc in hexane) gave 330 mg (79%) of the corresponding acid. To this acid in 3 mL EtOH was added NaOH (1N, 1.0 equivalent). The solvent was evaporated and the product was lyopholyzed to give the title compound.

Exact mass for C$_{33}$H$_{33}$ClNO$_3$S$_2$Na (M+1): Calculated: 614.1566 Found: 614.1566

$^1$H NMR (CD$_3$COCD$_3$): δ0.2–0.43 (4H, m), 1.53 (6H, 2s), 2.26 (2H, m), 2.28 (2H, s), 2.6 (2H, s), 2.75–2.85 (1H, m), 2.95–3.3 (1H, m), 4.04 (1H, dd, J'=7.5 Hz, J=11.25 Hz), 7.01–7.08 (3H, m), 7.33–7.35 (3H, m), 7.42–7.47 (1H, d, J=16.5 Hz), 7.53 (1H, d, J=7 Hz), 7.65 (1H, s), 7.66 (1H, d, J=8.5 Hz), 7.82–7.88 (1H, d, J=17 Hz), 8.0 (1H, s), 8.34–8.37 (1H, d, J=8.5 Hz)

EXAMPLE 2

Sodium 1-(((1(R)-(3-(2-(thieno[3,2-b]pyridin-5-yl)ethenyl) phenyl)-3-(2-(1-hydroxy-1-methylethyl)phenyl) propyl)thio)methyl)cyclopropaneacetate Step 1: ((Thieno[3,2-b]pyridin-5-yl )methyl)triphenylphosphonium chloride Using the procedure described in Steps 4–5 of Example 1, thieno[3,2-b]pyridine-5-carboxylic acid was convened to the title compound.

$^1$H NMR (CDCl$_3$): δ7.2 (2H, dd), 7.5–8.0 (17H, m), 8.2 (2H, m).

Step 2: Sodium 1-(((1(R)-(3-(2-(thieno[3,2-b]pyridin-5-yl)ethenyl)phenyl)-3-(2 -(1-hydroxy-1-methylethyl)phenyl)propyl)thio)-methyl)cyclopropaneacetate Using the procedure described in Steps 18–19 of Example 1, the phosphonium salt of Step 1 was converted to the title compound.

$^1$H NMR (CDCl$_3$): δ0.5 (4H, m), 1.6 (6H, 2s), 2.1 (2H, m), 2.4 (2H, m), 2.6 (2H, m), 2.9 (1H, m), 3.2 (1H, m), 4.0 (1H, t), 7.1 (3H, m), 7.2–7.5 (6H, m), 7.6 (2H, t), 7.8 (2H, t) 8.2 (1H, d, J=8 Hz). Anal. Calcd for C$_{33}$H$_{34}$NO$_3$S$_2$Na; C, 68.37; H, 5.91; N, 2.42 Found: C, 68.54; H, 5.96; N, 2.46.

EXAMPLE 3

Sodium 1-(((1(R)-(3-(2-(3-bromothieno[3,2-b]pyridin-5-yl) ethenyl)phenyl)-3-(2-(1-methylethyl)phenyl)propyl) thio)methyl)cyclopropaneacetate Step 1: Methyl 3-bromothieno[3.2-b]pyridine-5-carboxylate To a solution of HCl (10%) in MeOH (10 mL) was added thieno[3,2-b]pyridine-5-carboxylic acid (1.0 g, 5.6 mmol, from Step 2, Example 1) and the mixture heated to reflux for 2 hr. After cooling to r.t., half the solvent was removed by evaporation and the remainder was partitioned between EtOAc and H$_2$O. Solid NaHCO$_3$ was added until the system remained basic. Separation, drying, and evaporation of the organic layer afforded 0.75 g (70%) of methyl thieno[3,2-b]pyridine-5-carboxylate.

To a solution of methyl thieno[3,2-b]pyridine-5-carboxylate (0.400 g, 2,07 mmol) in 2 mL of $CHCl_3$ at 0° C. was bubbled HCl for 2 min. The solvent was evaporated under reduced pressure and the solid was heated 12 hr. at 70° C. in a sealed tube in a mixture of bromine (2 mL) and $CHCl_3$ (2 mL). After cooling, a 10% solution of $NaHCO_3$ was added and the reaction mixture was extracted with $CH_2Cl_2$ (3×50 mL). The organic phases were washed with $NaHSO_3$ and dried over $Na_2SO_4$. The organic solvents were evaporated and the title bromide was purified by flash chromatography on silica with EtOAc:Hexane 3:7 to give 0.343 g (61%).

$^1$H NMR ($CDCl_3$) δ4.06 (3H, m), 7.89 (1H, s), 8.19 (1H, d), 8.33 (1H, d). MS, m/e 272 ($m^+$+1).

Step 2: 3-Bromothieno[3,2-b]pyridine-5-methanol

To a −78° C. solution of the methyl ester (0.388 g, 1.42 mmol) of Step 1 in 5 mL of THF was added DIBAL (3.55 mmol) over 5 min. The reaction mixture was left 30 min after which time the solution was brought to 0° C. and quenched with MeOH. Sodium potassium tartrate solution was added and the mixture extracted with EtOAc. The organic phase was dried over $Na_2SO_4$, and the solvent evaporated. The crude oil was purified by flash chromatography on silica with EtOAc:hexane 2:3 to give 0.338 g (98%) of the title alcohol.

$^1$H NMR ($CDCl_3$) δ3.97(1H, t), 4.94(2H, d), 7.29(1H, d), 7.79(1H, s), 8.16(1H, d).

Step 3: 3-Bromo-5-(chloromethyl)thieno[3,2-b]pyridine

A mixture of thionyl chloride (5 mL) and the alcohol (0.331 g, 1.35 mmol) of Step 2 was heated at 70° C. for 30 min after which time the solvent was evaporated. The residue was taken in bicarbonate and extracted with dichloromethane. The organic phases were dried over $Na_2SO_4$ and the solvent removed. The crude was purified by flash chromatography on silica with EtOAc:Hexane 5:95 to give 0.170 g (48%) of the title chloride.

$^1$H NMR ($CD_3COCD_3$) δ4.90(2H, s), 7.58(1H, d), 8.20(1H, s), 8.55(1H, d).

Step 4: ((3-Bromothieno[3,2-b]pyridin-5-yl)methyl)triphenylphosphonium chloride

A mixture of the chloride (0.165 g, 0.62 mmol) of Step 3 and triphenylphosphine (0.325 g, 1.24 mmol) in 4 mL of acetonitrile was refluxed for 12 hr. After such time the resulting suspension was cooled and the solvent removed. The crude solid was swished in acetone:ether 1:1 to yield 0.296 g (91%) of the title phosphonium salt.

$^1$H NMR ($CDCl_3$) δ6.04(2H, d), 7.58–7.71(10H, m), 7.94–7.99(6H, m), 8.08(1H, d), 8.26(1H, d).

Step 5: Methyl 1-(((1(R)-(3-(2-(3-bromothieno[3,2-b]pyridin-5 -yl)-ethenyl)phenyl)-3-(2-(1-hydroxy-1 -methylethyl)phenyl)propyl)thio)methyl)cyclopropaneacetate A 1 molar solution of potassium t-butoxide (0.57 mL, 0.57 mmol) was added to a −78° C. suspension of the phosphonium salt (0.290 g, 0.55 mmol) of Step 4, in 3 mL of THF. The temperature was brought to 0° C. for 20 min then lowered back to −78° C. followed by the addition of a 0.5 molar solution of methyl 1-(((1(R)-(3-formylphenyl)3-(2-(1-hydroxy-1-methylethyl)phenyl)propyl)thio)methyl)cyclopropaneacetate (1.47 mL, 0.44 mmol) of Step 17 of Example 1. The bath was brought to 0° C. for 1 hr and the reaction mixture was quenched with a 25% aqueous $NH_4OAc$. The organic solvents were evaporated and the title product was purified by flash chromatography on silica with EtOAc:hexane 30:70 to yield 0.270 g (94%).

$^1$H NMR ($CD_3COCD_3$) δ0.38–0.51(4H, m), 1.55(6H, s), 2.22(2H, m), 2.42(2H, AB), 2.55(2H, s), 2.89(1H, m), 3.14(1H, m), 3.57(3H, s), 3.90(1H, s), 4.05(1H, t), 7.04–7.25(3H, m), 7.40(3H, m), 7.50(1H, d), 7.5(1H, m), 7.70(1H, d), 7.76(1H, s), 7.90(1H, s), 8.13(1H, s), 8.39( 1H, d).

Step 6: Sodium 1-(((1(R)-(3-(2-(3-bromothieno[3,2-b]pyridin-5 -yl)-ethenyl)phenyl)-3-(2-(1-hydroxy-1 -methylethyl)phenyl)propyl)thio)methyl)cyclopropaneacetate A 2N solution of NaOH (0.41 mL, 0.82 mmol) was added to the methyl ester (0.279 g, 0.41 mmol) of Step 5 in a 2 mL mixture of methanol/THF (0.5 mL/1.5 mL) and stirred 12 hr. The solution was poured in 25% aqueous $NH_4OAc$ and extracted with EtOAc. The organic solvents were evaporated and the crude oil purified by flash chromatography on silica with EtOAc:hexane 40:60 with 2% of acetic acid to yield 0.224 g (86%) of the corresponding carboxylic acid. This acid was dissolved in ethanol and 1 eq of sodium hydroxide (1N) was added. The solvents were removed and the oil was lyopholized to yield 0.231 g (99%) of the title compound.

Exact mass for $C_{33}H_{33}BrNaNO_3S_2+H^+$: Calculated: 658.1060 Found: 658.1061.

EXAMPLE 4A

Sodium 1-(((1(R)-(3-(2-(2,3-dichlorothieno[3,2-b]pyridin-5-yl)-(E)-ethenyl)-phenyl)-3 -(2-(1-hydroxy-1-methylethyl)phenyl)propyl)thio) methyl)cyclopropaneacetate Step 1: Methyl 2,3-dichlorothieno[3,2-b]pyridine-5-carboxylate A mixture of methyl thieno[3,2-b]pyridine-5-carboxylate (from Ex. 3, Step 1) (0.20 g, 1.03 mmol) and trichloroisocyanuric acid (0.962 g, 4.14 mmol) was refluxed in $CH_3CN$ for 16 hr. The solvent was removed and the crude solid was chromatographed on silica gel with 5% EtOAc in toluene as eluant to afford 0.189 g (70%) of the title compound.

$^1$H NMR ($C_6D_6$) δ3.55 (3H, s), 6.75 (1H, d, J=6.5 Hz), 7.75 (1H, d, J=6.5 Hz).

Step 2: 2.3-dichloro-5-(chloromethyl)thieno[3.2-b]pyridine

Using the procedure described in Steps 2 and 3 of Example 3, methyl 2,3-dichlorothieno[3,2-b]pyridine-5-carboxylate (0.100 g, 0.38 mmol) was converted in 99% yield to the title compound.

$^1$H NMR ($CDCl_3$) δ4.75 (2H, s), 7.50 (1H, d), 8.00 (1H, d).

Step 3: ((2,3-Dichlorothieno[3,2-b ]pyridin-5-yl)methyl) triphenylphosphonium chloride Using the procedure described in Step 4 of Example 3, 2,3 -dichloro-5-(chloromethyl)thieno[3,2-b]pyridine (0.078 g, 0.30 mmol) was convened in 81% yield to the title compound.

$^1$H NMR ($CDCl_3$) δ6.05 (1H, d), 7.50–8.00 (16H, m), 8.42 (1H, d).

Step 4: Methyl 1-(((1(R)-(3-(2-(2,3-dichlorothieno[3,2-b] pyridin-5 -yl)-(E)-ethenyl)phenyl)-3-(2-(1-hydroxy-1 -methylethyl)phenyl)-propyl)thio)methyl)cyclopropaneacetate Using the procedure described in Step 18 of Example 1, ((2,3-dichlorothieno[3,2-b]pyridin-5-yl)methyl)triphenylphosphonium chloride (0.280 g, 0.54 mmol) was converted in 77% yield to the title compound.

$^1$H NMR ($CD_3COCD_3$) δ0.45(4H, m), 1.56(6H, s), 2.20(2H, m), 2.42(2H, AB), 2.56(2H, s), 2.88(1H, m), 3.15(1H, m), 3.58(3H, s), 4.06(1H, t), 7.13(3H, m), 7.40–7.50(4H, m), 7.59(1H, d), 7.71(1H, d), 7.76(1H, s), 7.92(1H, d), 8.31(1H, d).

Step 5: Sodium 1-(((1(R)-(3-(2-(2,3-dichlorothieno[ 3,2-b]

pyridin-5-yl)-(E)-ethenyl)phenyl)-3-(2-(1-hydroxy-1-methylethyl)phenyl)propyl)thio)methyl)cyclopropaneacetate Using the procedure described in Step 19 of Example 1, the previous methyl ester (0.176 g, 0.27 mmol) was converted in 86% yield to the title compound.

Anal. Calcd. for $C_{33}H_{32}Cl_2NNaO_3S_2 \cdot 1.5H_2O$: C, 58.66; H, 5.22; N, 2.07; $C_{l, 10.49}$ Found: C, 58.78; H, 5.15; N, 2.27; Cl, 11.06.

EXAMPLE 4B 1-(((1(R)-(3-(2-(2,3-dichlorothieno[3,2-b]pyridin-5-yl)-(E)-ethenyl)phenyl)-3-(2-(1-hydroxy-1-methylethyl) phenyl)propyl)thio)methyl)cyclopropaneacetic acid Step 1: 3-Amino-2-hydroxymethylthiophene In to a 10 L, 3-neck round bottom flask equipped with a calibrated thermometer, a mechanical stirrer and a septum inlet were canulated 3.2 L of a 1M solution of $LiAlH_4$ in THF. An ethanol Dry Ice bath was used to cool the reaction mixture to +7° C., at which temperature a solution of 440 g of methyl 3-amino-2-thiophenecarboxylate in 550 mL of THF was pumped in at a rate of 20 mL/min. After ca. 5 min, the internal temperature started to rise rapidly. The cooling bath temperature was then lowered to −15° C. and the addition was stopped. The addition was resumed when the inside temperature was at +2.5° C., at a rate such that it remained +2.5° C.±2° C. The complete addition took 100 minutes. In the last pan of the addition, the internal temperature was proportional to the rate of addition. At the end of the addition, the bath was adjusted to −2° C., and the reaction was stirred until the internal and external temperature were within 0.5° C., which took~1 h. At this time, the starting material and the impurity (3-amino-2-methylthiophene) spots were equal by u.v. on thin layer chromatography (3:1 EtOAc-hexane on $SiO_2$). The bath was then cooled to −55° C. When the inside temperature reached −15° C., 3.2 L of THF were added at such a rate to keep the internal temperature constant. After the THF addition was complete, the reaction mixture temperature fell to −20° C. under vigorous stirring. Water (120 mL) was then cautiously added dropwise, at a rate such that the internal temperature remained constant at −20° C.±4° C. This quench took ca. 20 min. After the water addition, 240 mL of aqueous 10N NaOH were added dropwise over 20 min. while the cooling bath was removed. The mixture was heated in a steam bath to 40° C., and was filtered. The solid was washed by stirring 10 min with 3 L of boiling THF, and filtering, a total of 5 times. The filtrates were concentrated on a rotary evaporator and co-evaporated with 1 L of EtOAc. To the crystalline residue was added 500 mL of EtOAc at −78° C. and the mixture swirled for 2 minutes. The mixture was filtered, and the crystals were washed with 300 mL of EtOAc at −78° C. The solid was air dried for 10 min, and fluffed in a crystallizing dish until the weight was constant. Yield: 298.0 g, of the title compound mp: 86.5°–89.5° C.

$^1$H NMR ($CDCl_3$) δ7.05 (d, 1H), 6.58 (d, 1H), 4.65 (s, 2H), 3.75 (brs, 2H), 2.24 (s, 1H).

Step 2: 5-Methylthieno[3,2-b]pyridine (IV)

A 5 L three neck flask was charged with 562 g (4.35 mol) of 3-amino-2-hydroxymethylthiophene (Step 1). It was suspended in 3 L of EtOAc and cooled to 0° C. (ice bath). 2.0 Kg of $MnO_2$ (23.0 mol.; 5.3 eq) was added portionwise (250 g) over 45 min. with mechanical stirring. Upon addition of the $MnO_2$ the reaction temperature rose to 20° C. The reaction mixture was stirred at 20° C. for 1 h until total consumption of starting material by TLC (Hex/EtOAc 1:1). The solids were removed by filtration over 2 L of celite and washed 3 times with 2 L of EtOAc/THF (1:1). The combined filtrates were evaporated to dryness to give a black residue. The residue was dissolved in 1.28 L of acetone (17.4 mol, 4.0 eq) and transferred to a 10 L three neck flask charged with 3 L of 2.5% NaOH. The mixture was then stirred at 70° C. for 1 h. The two phase mixture was cooled to 20° C., 2 L of ether was added and stirred for 15 min. The phases were separated and the aqueous phase was backwashed with 2×1 L of ether. The organic fractions were combined, washed with 2 L of brine and evaporated to dryness to give a black oil. The latter was distilled under vacuum (@70° C., 0.3 mm Hg) to give the title compound: 492 g; 76%.

$^1$H NMR ($CDCl_3$) δ8.02 (1H, d), 7.65 (1H, d) 7.45 (1H, d), 7.08 (1H, d), 2.63 (3H, s).

Step 3: 2,3-Dichloro-5-methylthieno[3,2]pyridine (Ve)

A 10 L three neck flask was charged with 762g (5.11 mol) of thienopyridine (Step 2) dissolved in 1.5 L of $CH_3CN$ and then cooled to 0° C. (ice bath); 205 mL (2.54 mol; 0.5 equiv.) of pyridine diluted in 205 mL of $CH_3CN$ was then added rapidly followed by 205 mL (2.54 mol; 0.5 equiv.) of $SO_2Cl_2$ dissolved in 205 mL of $CH_3CN$. The $SO_2Cl_2$ was added dropwise so that the reaction temperature remained between 15° and 20° C. Care must be taken because the addition of $SO_2Cl_2$ is very exothermic. The addition of 205 mL of pyridine and 205 mL of $SO_2Cl_2$ was repeated 4 times in a similar fashion. The time of addition was 2.5 h. A total of 1025 mL of pyridine (12.8 mol; 2.5 equiv.) and 1025 mL of $SO_2Cl_2$ (12.8 mol; 2.5 equiv.) were added. At the end of both additions the reaction mixture was stirred a extra 30 min. at 18° C.

The reaction mixture was evaporated to dryness to give an orange paste to which was added 900 mL of pyridine in 1.7 L of $CH_3CN$. The mixture was stirred until an homogeneous dark brown solution was obtained (20 min.). The resulting solution was then evaporated to dryness. To the residue was added 5 L of water and 5 L of EtOAc and the mixture stirred 15 min. The water layer was removed and backwashed with 2.5 L of EtOAc. The organic phases were combined, washed 2 times with 2.5 L water, dried with 2 L of brine, evaporated to dryness and finally, 2 L of toluene was added then evaporated to dryness. The resulting brown solid was dissolved by stirring it at 40° C. for 15 min in 4 L toluene/ hexane 1:1. The solution was split in two, and each fraction was poured onto a 6 L silica gel wet pad (toluene/hexane 1:1). The mixture/silica gel ratio was 1 g/10 g $SiO_2$. Each pad was eluted with;

| Fraction 1–4: | 4 × 3 L tol/hex 1:1 | |
|---|---|---|
| | | tol = toluene |
| Fraction 5: | 1 × 3 L tol | |
| | | hex = hexane |
| Fraction 6: | 1 × 3 L tol/EA 1% | |
| | | EA = EtOAc |
| Fraction 7: | 1 × 3 L tol/EA 2% | |
| Fraction 8: | 1 × 3 L tol/EA 3% | |
| Fraction 9: | 1 × 3 L tol/EA 4% | |
| Fraction 10–12: | 3 × 3 L tol/EA 5% | |

The desired material was found in fractions 5–12. They were combined and evaporated to dryness, 2.5 L of hexane was added and stirred at 80° C. until the beige solid was all dissolved. The solution was filtered while hot (flask was rinsed with 500 mL hot hexane), and allowed to cool slowly to 0° C. The solution was seeded at 60° C. and crystallisation started immediately. The crystals were filtered at 0° C. and washed with 500 mL of −78° C. hexane, to give 646 g (59%)

of 99.0% pure title compound. The supernatant after evaporation gave 142 g of a 1:1 mixture of mono-and dichlorothienopyridine. Fractions 3 and 4, composed of tetra-, tri-, and dichlorothienopyridine were combined and evaporated to give 242 g of tetra/tri/di (3:1:1) chlorinated derivatives of 5-methylthienol[3,2-b]pyridine.

$^1$H NMR of the title compound (CDCL$_3$) δ7.88 (1H, s), 7.17 (1H, d), 2.70 (3H, s).

Step 4: 3-(2-(2,3-Dichlorothieno[3,2-b]pyridin-5-yl)-(E)-ethenyl)benzaldehyde (XLIV)

A mixture of 2,3-dichloro-5-methylthieno[3,2-b]pyridine (Step 3) (440 g, 2.01 mol), isophthalaldehyde (808 g, 6.02 mol) and ±camphorsulfonic acid (513 g, 2.21 mol) in 1.2 L of mesitylene was heated in a 190° C. oil bath for 15 h. The mixture was cooled to 100° C. and 4.3 L of EtOAc was added followed by 70 mL of H$_2$SO$_4$(conc.) in 250 mL of cold ethyl ether. It was then refluxed and filtered while hot. The solid obtained was taken up in 1.8 L of EtOAc, refluxed and filtered hot. This was repeated with 1.8 L of EtOAc. The solid collected was poured in to a solution of 610 mL of NaOH (10N) in 6.5 L of water and 5 L of EtOAc. The organic phase was separated and the aqueous phase was washed with EtOAc (2×2.6 L). The organic phases were combined and washed with brine (4 L) and the solvent removed under vacuum. Toward the end of the evaporation, 500 mL of toluene was added and the evaporation was continued. The residue was refluxed in 4.3 L of EtOAc for 4 h, at the end of which the mixture was cooled to RT and filtered. The solid obtained (71 g) contained 18% of the title product. After evaporation of the solvent, 421 g of the title product was isolated (61%).

$^1$H NMR (CDCl$_3$): δ10.0 (1H, s), 8.1 (1H, s), 8.0 (2H, d), 7.8 (1H, t), 7.7 (1H, d), 7.6 (1H, t), 7.5 (1H,d), 7.4 (1H, d).

Step 5: 1-(3-(2-(2,3-Dichlorothieno[3,2b]pyridin-5-yl)-(E)-ethyl)phenyl)-2-propen-1-ol(XLV)

To the aldehyde (XLIV) from Step 4 (30 g, 89.8 mmol) dissolved and degassed in toluene (450 mL) at 0° C. was added dropwise a freshly prepared solution of vinyl magnesium bromide (107 mL, 1M solution in THF) over a period of 30 minutes. The mixture was stirred 20 minutes at 0° C. Aqueous HOAc (3N, 250 mL) was added and the mixture was stirred at r.t. for 10 minutes. Ethyl acetate (250 mL) was added, the organic layer was separated and washed once with 10% Na$_2$CO$_3$ (250 mL) and once with brine, dried over MgSO$_4$ and concentrated under reduced pressure. The crude oil was purified with a pad of SiO$_2$ (1:5 weight by weight) using toluene to 10% EtOAc in toluene to yield 24.71 g (76%) of the title compound.

$^1$H NMR (CDCl$_3$) δ2.0 (1H, d), 5.2 (2H, m), 5.4 (1H, d), 6.05 (1H, m), 7.3–7.4 (3H, m), 7.5 (2H, m), 7.6–7.75 (2H, m), 7.95 (1H, d).

Step 6: 1-(3-(2-(2,3-Dichlorothieno[3,2b]pyridin-5-yl)-(E)-(ethenylphenyl)-3-( 2-carbomethoxyphenyl-1-propanone (XLVI)

The allylic alcohol (Step 5) (414.16 g, 1.14 mol) methyl 2-iodobenzoate (356.39 g, 1.36 mol), Pd(OAc)$_2$ (7.68 g, 03 mol), LiOAc (290.75 g, 2.8 mol), LiCl (241.62 g, 5.70 mol) and tetrabutylammonium chloride (316.80 g, 1.14 mol) were degassed in a flask. Then DMF (4.2 L) was added, the solution degassed 2 times and heated 4 h at 85° C. To the hot solution was added water (1 L) to initiate the precipitation. Water (10 L) was added slowly. The reaction mixture was left overnight at 25° C. and the solid residue filtered and washed with 2 L of water. The solid was suspended in 4 L of hot water, stirred 30 min and filterd hot. This was repeated one more time. Then it was swished in 800 mL of acetonitrile at 25° C. for 30 min, filtered and rinced with cold acetonitrile. The product was crystallized from 1 L of hot toluene and 100 mL of hexane, cooling to –20° C. This gave 403.70 g (71%) of the title product.

$^1$H NMR (CDCL$_3$): δ8.2 (1H, s), 8.0 (1H, d), 7.9 (2H, t), 7.7 (2H, m), 7.4–7.5 (5H, m), 7.3 (1H, t), 3.9 (3H, s), 3.4 (4H, s).

Step 7: 1-(3-(2-(2,3-Dichlorothieno[3,2b]pyridin-5 -yl)-(E)-ethenyl)phenyl)-3-(2-carbomethoxy)-1-(S)-propanol (XLVII)

A reducing agent was prepared via a solution of (R)-(+)-apinine (15 ml) in hexane (11.5 mL), cooled to 0° C. To this solution BH$_2$Cl dimethyl sulfide complex (4.2 ml, 40.32 mmol) was added slowly over 30 minutes, keeping the temperature below 3° C., stirred 30 minutes at 0° C. and another 30 minutes at 40° C. The ketone of step 6 (10 g, 20.16 mmol) in THF (100 ml) was cooled to 0° C. and diisopropylethylamine (1.38 ml, 7.8 mmol) was added to the slurry. The borane solution which had been warmed to 40° C. was added over 30 minutes to the ketone slurry via cannula. During the addition the temperature was kept below 3° C. The reaction mixture was stirred overnight at 0° C. Excess reducing agent was quenched by addition of acetone (5 ml). This was followed by the addition of 10% Na$_2$CO$_3$ (50 ml) followed by H$_2$O (50 ml). The biphasic mixture was stirred for 1.5 hours at 20° C. and the layers were separated. The organic layer was washed with brine (50 ml), dried over MgSO$_4$ and concentrated under reduced pressure. The crude oil was dissolved in EtOAc (100 mL), cooled to 0° C. and HCl (conc) (2 ml) was added and the resulting yellow solid filtered. The yellow solid was suspended in EtOAc (50 mL) and stirred with 50 mL of 10% aqueous diethanolamine until a biphasic solution was obtained. The organic phase was separated, dried over MgSO$_4$ and evaporated. The crude product was purified by flash chromatography over silica with EtOAc: hexane 30:70 to give 7.6 g or 76% of the title compound.

$^1$H NMR (CDCl$_3$) δ2.10(2H, m), 2.96(1H, d), 3,10(2H, m), 3.9(3H, s), 4.75 (1H, m), 7.2–7.50(84, m), 7.60–7.70(2H, m), 7.90(1H,d), 7.95 (1H, d).

Step 8: 1-(3-(2-(2,3-Dichlorothieno[3,2b]pyridin-5-yl)-(E)-ethenyl)phenyl)-3 -(2-(1-hydroxyl-methylethyl)phenyl)-1-(S)-propanol Cerium chloride (anhydrous, 1.07 g, 4.2 mmol) was refluxed overnight with molecular sieves in 14 mL of THF. It was then cooled to 0° C. and methyl magnesium chloride 3M (6,67 mL, 20 mmol in THF) was added slowly and left 90 min at 0° C. The hydroxy ester from Step 7 (2.00 g, 4.0 mmol) in 16 mL of toluene was added slowly to keep the temperature around 5° C., and left 1 hour. The reaction was then poured in to 50 mL of 25% NH$_4$OAc, left 30 min and extracted twice with EtOAc (50 mL). After being dried with Na$_2$SO$_4$ the solvent was removed and the residue taken up in 1/1 hexane-EtOAc and filtered over a silica pad. The eluent was evaporated to give 1.92 g (96%) of the title product.

$^1$H NMR (CDCL$_3$): δ8.0 (1H, d), 7.7 (1H, d), 7.6 (1H, s), 7.5 (2H, d), 7.35–7.15 (6H, m), 7.1 (1H, t), 4.7 (1H, m), 3.2 (1H, m), 3.1 (1H, m), 2.9–2.6 (1H, bs), 2.1 (1H, m), 1.7 (3H, s), 1.65 (3H, t).

Step 9: 1,1-Cyclopropanedimethanol Cyclic Sulfite

Method A. To a 1 L round bottom flask equipped with a stirrer, a thermocouple, a nitrogen inlet and a syringe pump were added CH$_2$Cl$_2$ (645 mL) and 1,1-cyclopropanedimethanol (10.64 g; 97.93 mmol Example 1 Step 6). The mixture was stirred for 10 minutes to ensure complete dissolution. N,N-Diisopropylethylamine (34.21 mL; 195.86 mmol) was added, and the solution was cooled to 0°–5° C.

$SOCl_2$ (7.01 mL; 96.04 mmol) was added subsurface through a teflon needle via a syringe pump over 60 minutes. The reaction solution was transferred to a separatory funnel containing cold (0°–5° C.) phosphate buffer (pH=7.2, 650 mL). After equilibration, the layers were separated. The organic phase was washed with 2 wt % NaCl solution (650 mL), and was then azeotropically dried and concentrated at 35°–40° C. under atmospheric pressure to 50 mL. Assayed yield=13.07 g (90%) of the title product.

Method B. A 25 mL graduated cylinder equipped with a ground glass joint was charged with 7.14 mL (97.9 mmol) of $SOCl_2$ and then diluted with toluene to a volume of 21 mL.

To a 1 L round bottom flask equipped with an overhead stirrer, a thermocouple, a nitrogen inlet and a syringe pump were added toluene (636 mL), 1,1-cyclopropanedimethanol (10.00 g; 97.9 mmol Example 1 Step 6) and N,N-diisopropylethylamine (32.41 mL; 186.1 mmol). The two phase mixture was vigorously stirred at 22° C. The $SOCl_2$:toluene solution (21 mL; 97.9 mmol) was added subsurface through a teflon needle via a syringe pump over 90 minutes maintaining the reaction temperature at or below 40° C. The reaction mixture was transferred to a separatory funnel containing cold (0°–5° C.) phosphate buffer (pH=7.2, 650 mL). After equilibration, the layers were separated and the product solution in toluene was washed with 2 wt % NaCl solution (650 mL). The product solution was then azeotropically dried and concentrated at 40°–45° C./70 Torr to 70 mL. Assayed yield=12.33 g (85%) of the title compound.

Step 10: 1-(Hydroxymethyl)cyclopropaneacetonitrile

Method A. A 250 mL round bottom flask equipped with an overhead stirrer, a thermocouple, distillation head and receiving flask was charged with the solution of the cyclic sulfite of Step 9 in $CH_2Cl_2$ (61 mL; 158.9 mg/mL; 9.69 g). The solution was concentrated to approx. 20 mL by distillation under atmospheric pressure. Isopropyl acetate (IPAc) (2×30 mL) was added to the batch and the distillation was continued to a final volume of 13 mL. Dimethylformamide (27 mL) was added to the solution at >55° C. and the solution was cooled to RT.

A 250 mL round bottom flask equipped with an overhead stirrer, a thermocouple, a reflux condenser and a nitrogen inlet was charged with the above solution of cyclic sulfite in DMF: IPAc (4:1). Sodium cyanide (4.61 g; 94 mmol) and NaI (3.75 g; 25.0 mmol) were added at RT. The reaction mixture was heated to 70°±3° C. and aged at that temperature until the reaction was complete. The reaction mixture was allowed to cool to room temperature and diluted with cold (0°–5° C.) IPAc (187 mL). The dark yellow slurry was transferred to a separatory funnel containing cold (0°–5° C.) 1.0M NaOH (107 mL). After equilibration, the layers were separated. The organic layer was washed with brine (53 mL). The aqueous layer was back-extracted with cold (0°–5° C.) IPAc (107 mL), and the organic layer washed with brine (27 mL). The two organic layers were combined to provide 17.5 mg/ml of the title compound in solution. Assayed yield=5.03 g; 72.2%

Method B. A 12 L 3 neck round bottom flask equipped with an overhead stirrer, a thermocouple, a distillation head and 3 L receiving flask was charged with the solution of the cyclic sulfite of step 9 in $CH_2Cl_2$ (2.0 L; 174.0 g/L; 343.6 g). The solution was concentrated and a second portion of the cyclic sulfite in $CH_2Cl_2$ (2.0 L; 155.9 g/L; 311.8 g) was added and further concentrated to approx. 2.3 L by distillation under atmospheric pressure. Toluene (1.7 L) was added to the batch and the distillation was continued to a final volume of approx. 1.7 L. Dimethylformamide (1.81 L) was added to the solution and concentration was continued under vacuum (approx. 105 Torr) to 2.2 L.

A 12 L 3 neck flask equipped with an overhead stirrer, a thermocouple, a distillation head and a nitrogen inlet which contained the above solution of cyclic sulfite (4.40 mol) in DMF: toluene (97:3/v:v) at room temperature was charged with NaCN (218.9 g; 4.40 mol) and NaI (131.9 g; 0.88 mol). The reaction mixture was heated to 70°±3° C. over a 1 h period and aged at that temperature until the reaction was complete.

The reaction mixture was slowly diluted with 6.6 L of toluene maintaining the temperature of the batch at approx. 70° C. The hazy amber solution was charged with 80 mL of water over a 30 min period. The reaction mixture was cooled to 27° C. and the reaction flask was equipped with a 2 L dropping funnel which contained 2 L of toluene. The reaction mixture was concentrated under vacuum while the toluene was added from the dropping funnel. The reaction mixture was cooled overnight and then filtered through a medium porous sintered glass funnel (3 L). This filtration required 6.5 h. The cake was flushed with an additional 2.2 L of toluene which required 1.5 h. The yield of the title compound was 87.5%.

Step 11: 1-(Acetylthiomethyl)cyclopropaneacetonitrile

Method A. A 500 mL round bottom flask equipped with an overhead stirrer, a thermocouple, distillation head and receiving flask was charged with the solution of the hydroxy-nitrile of Step 10 Method A (118-mL; 91 mg/mL; 10.74 g). The solution was concentrated to approx. 50 mL by distillation under atmospheric pressure. IPAc (200 mL) was added to the batch and the distillation was continued to a final volume of 154 mL.

The distillation set up was replaced with an addition funnel. The solution was cooled to −3°±2° C. and triethylamine (17.4 mL) was added over 1 minute. Mesyl chloride (8.93 mL) was added slowly from the addition funnel keeping the temperature of the batch below 0° C. The addition took 30 minutes. The reaction mixture (approx. 180 mL) was transferred to a separatory funnel containing cold (0°–5° C.) water (76 mL). After equilibration, the layers were separated and the organic layer was washed with brine (76 mL).

The solution of 1-methanesulfonyloxymethylcyclopropaneacetonitrile was transferred to a 500 mL round bottom flask equipped with an overhead stirrer, a thermocouple and a nitrogen inlet. Solid potassium thioacetate (14.28 g) was added to the solution at 0° C. The heterogeneous mixture was warmed to 20°±2° C. and aged for 16 to 18 hours. Water (76 mL) was added to the reaction mixture and the contents of the reaction flask were transferred to a separatory funnel. The layers were separated and the organic layer was washed with brine (76 mL). The solution of the title compound in IPAc was concentrated under vacuum (75 Torr, 50° C.) to a volume of approx. 50 mL. Toluene (3×75 mL) was added and the concentration was continued under vacuum (60 Torr, 50° C.) until GC assay indicated <1% of IPAc. Assayed yield=13.12 g (81%) of the title compound.

Method B. A solution of 1-(hydroxymethyl)cyclopropaneacetonitrile (34.2 g, 0.308 mol) in toluene:DMF (1.9:1, 210 mL) and triethylamine (49.4 mL, 0.354 tool) were combined in a 3-neck, 1 L round bottom flask equipped with mechanical stirring and a thermocouple, flushed with nitrogen and cooled to −15° C. Mesyl chloride (26 mL) was added dropwise over 0.5 hr., keeping the temperature below 5° C. Ethanol (77 mL), triethylamine (86 mL, 0.616 mol) and thiolacetic acid (26.4 mL) were added sequentially as quickly as possible. The mixture was removed from the cooling bath and heated to 35° C. This temperature was maintained until <1% mesylate remains, about 7 hrs. Water (250 mL) was added and the mixture was shaken. The phases were separated, the aqueous phase was back-extracted with toluene (200 mL), and the organic phases were combined to provide the o title compound (48.3 g at 103 mg/mL, 93% yield, purity: 91%).

Step 12: 1-(Mercaptomethyl)cyclopropaneacetic acid

Method A. A 1 liter round bottom flask equipped with an overhead stirrer, a thermocouple, distillation head and receiving flask was charged with a solution of 1-(acetylthiomethyl)cyclopropaneacetonitrile (Step 11) in IPAc (248.2 mL; 16.93 g; 100.0 mmol). The solution was concentrated under vacuum (75 Torr, 50° C.) to a volume of approx. 100 mL. Toluene (3×250 mL) was added and the concentration was continued under vacuum (60 Torr, 50° C.) until GC assay indicated <1% of IPAc. The distillation set up was removed, the solution was cooled under nitrogen to 20°–25° C., and aqueous NaOH(100 mL; 5N) was added. The biphasic mixture was vigorously agitated at 20°–25° C. for 16–18 hours.

The aqueous layer was transferred to a 250 mL flask equipped with an overhead stirrer, a thermocouple, a nitrogen inlet and a reflux condenser. The solution was refluxed for approx. 2 hours, cooled to 0°–5° C. and 8.0N hydrochloric acid (62.5 mL; 500 mmol) was added to adjust the pH of the aqueous medium to 2.0. Toluene (190 mL) was added to the aqueous slurry with good stirring. The biphasic mixture was transferred to a separatory funnel and the layers were separated. Toluene (100 mL) was added to the aqueous layer and the layers were separated. The two organic layers were combined and concentrated under vacuum (60 Torr, 50° C.) to 82 mL, and the concentrated solution was filtered. Assayed yield=11.99 g (82%). The solution of the title compound in toluene was stored under nitrogen.

A 250 mL round bottom flask equipped with an overhead stirrer, a thermocouple, distillation head and receiving flask was charged with the solution of the title compound in toluene (100 mL; 11.50 g; 78.66 mmol). The solution was concentrated under vacuum (45 Torr, ≦40° C.) to a volume of approx. 23 mL. Hexane (92 mL) was added to the solution at 20°±2° C., and the solution was seeded with 10 mg of the title compound. The mixture was aged at 20°±2° C. for approx. 2 hrs to obtain a good seed bed. A sample of the slurry was examined by cross-polarized microscopy to confirm crystallinity of the solid.

The slurry was cooled to 0° to −5° C. and aged for about 2 hours, then allowed to warm to 20°±2° C. and aged overnight to digest the fine crystals. The slurry was cooled to −20°±5° C. over 3 hours and aged for one hour. A sample of the slurry was examined by cross-polarized microscopy to confirm crystallinity of the solid. The slurry was filtered and the cake was washed with cold (−20°±5° C.) hexanes (25 mL), then dried under suction under nitrogen at 20°±2° C. to yield 10.93 g (95%) of the title compound.

Method B. To a solution of methyl 1-(mercaptomethyl)cyclopropaneacetate (Example 1, Step 9) (10 g, 62.1 mmol) in 100 mL of 1:1MeOH:THF was added 100 mL of 1N aqueous NaOH. After 16 h at r.t., the reaction was diluted with EtOAc, cooled to 0° C. and acidified with 1N HCl to pH 2. The organic phase was separated and dried. After removal of the solvent, the residue was purified by flash chromatography with hexane/EtOAc (1:1) to give 9.4 g of the title compound.

Step 13: 1-(((1(R)-(3-(2-(2,3-dichlorothieno[3,2-b]pyridin-5-yl)-(E)-ethenyl)phenyl)- 3-(2-(1-hydroxy-1-methylethyl)phenyl)propyl)thio)methyl)cyclopropaneacetic acid The diol (1 g, 2.0 mmol) from Step 8 is dissolved in CH$_2$Cl$_2$ (20 ml) and cooled to −35° C. Et$_3$N (0.42 mL, 3 mmol) and methane sulfonyl chloride (0.2 mL, 2.6 mmol) are added. The temperature of the mixture is raised to 0° C. for 30 minutes. The reaction is quenched with a solution of NaHCO$_3$ (5%) and extracted with EtOAc (40 mL). The organic layer is separated, dried over MgSO$_4$ and concentrated under reduced pressure. In degassed THF (10 mL), the thiol from Step 12 (0.3 g 2.05 mmol) is cooled to −20° C. Butyllithium (1.6M, 2.56 mL, 4.11 mmol in hexane) is added dropwise over a period of 15 minutes. The temperature is raised to 0° C. for 15 minutes and then cooled to −25° C.

The mesylate is dissolved in THF (10 mL), and added dropwise to the thiolate suspension and stirred for 30 minutes. Then the temperature is raised to 0° C. for 2 hours. The reaction is quenched with a solution of NH$_4$OAc (25%, 25 mL) and extracted twice with EtOAc. The organic layer is separated, dried over MgSO$_4$ and concentrated under reduced pressure. The crude product is purified by flash chromatography over silica gel with EtOAc: hexane: HOAc 20:80:1 to yield the title compound.

EXAMPLE 5

Sodium 1-(((1(R)-(3-(2-(3-chlorothieno[3,2-b]pyridin-5-yl)ethyl)phenyl)-3-(2-(1-hydroxy-1-methylethyl)phenyl)propyl)thio)methyl)cyclopropaneacetate Step 1: Methyl 1-(((1(R)-(3-(2-(3-chlorothieno[3,2-b]pyridin-5-yl)-ethyl)phenyl)-3-(2-(1-hydroxy-1-methylethyl)phenyl)propyl)thio)methyl)cyclopropaneacetate To a solution of the olefin of Step 18 of Example 1 (270 mg, 0.456 mmol) in THF at 0° C. was added BH$_3$ in THF (1M) (1.36 mL, 1.37 mmol). The mixture was stirred for 5 hr. at room temperature. Addition of 25% aq. NH$_4$OAc and extraction with EtOAc followed by purification by flash chromatography (15% EtOAc in toluene) afforded 110 mg (41%)of the saturated compound.

Step 2: Sodium 1-(((1(R)-(3-(2-(3-chlorothieno[3,2-b]pyridin-5-yl)-ethyl)phenyl)-3-(2-(1-hydroxy-1-methylethyl)phenyl)propyl)thio)methyl)cyclopropaneacetate Following the procedure described in Step 19 of Example 1, the ester of Step 1 was hydrolyzed to the acid in 90% yield.

$^1$H NMR (300 MHz, CD$_3$COCD$_3$) δ0.30–0.55(4H, m), 1.50(6H, 2s), 2.10–2.20(2H, m), 2.40(2H, m), 2.50(2H, s), 2.80(1H, m), 3.10(1H, m), 3.15(2H, m), 3.30(2H, m), 3.45(1H, m), 7.15–7.45(8H, m), 8.00(1H, s), 8.30(1H, d).

The title compound sodium salt was then prepared. Anal. Calc'd. for C$_{33}$H$_{35}$ClNS$_2$O$_3$Na.3H$_2$O: C, 59.19; H, 6.18; N, 2.09 Found: C, 59.16; H, 5.92; N, 2.08.

EXAMPLE 6

Sodium 1-(((1(R)-(3-(2-(2-chlorothieno[3,2-b]pyridin-5-yl)ethenyl)phenyl)-3-(2-(1-hydroxy-1-methylethyl)phenyl)propyl)thio)methyl)cyclopropaneacetate Step 1: 2-Chloro-5-methylthieno[3,2-b]pyridine To a solution 5-methylthieno[3,2-b]pyridine (3.60 g, 24 mmol) and N,N-diisopropylamine (100 uL) in THF (80 mL) at −78° C. was added dropwise 16 mL of n-BuLi (1.6M, 25.6 mmol). The mixture was stirred at −78° C. for 20 min and then transfered via a cannula to a solution of N-chlorosuccinimide (4.5 g, 34 mmol) in THF (300 mL) at −10° C. The mixture was stirred at −10° C. for 30 min. Saturated NH$_4$Cl solution was then added and the product was extracted with EtOAc, dried over MgSO₄, and concentrated to an oil. Chromatography of the crude oil on silica gel (eluted with 15% EtOAc in hexane) yielded 3.60 g (81%) of the title compound.

¹H NMR (CDCl₃) δ2.65 (3H, s), 7.12 (1H, d, J=7.5 Hz), 7.34 (1H, s), 7.90 (1H, d, J=7.5 Hz).

Step 2: 5-(Bromomethyl)-2-chlorothieno[3,2-b]pyridine

A mixture of the product of Step 1 (0.371 g, 2.0 mmol), N-bromosuccinimide (0.396 g, 2.2 mmol), and benzoyl peroxide in 10 mL of carbon tetrachloride was refluxed under a sun lamp for 1 hr. After cooling to room temperature, the solvent was removed and the title bromide was purified by flash chromatography on silica (eluted with 5% EtOAc in hexane) to yield 0.284 g (46%).

¹H NMR (CDCl₃) δ4.63 (2H, s), 7.38((1H, s), 7.40 (1H, d), 8.04 (1H, d).

Step 3: ((2-Chlorothieno[3,2-b]pyridin-5-yl)methyl)triphenylphosphonium bromide

A solution of bromide (0.304 g, 1.16 mmol) of Step 2 and triphenylphosphine (0.455 g, 1.73 mmol) in 6 mL of acetonetrile was stirred at r.t. for 20 hr. Ether was added and the solid was washed with ether to yield 0.550 g (91%) of the title phosphonium salt.

¹H NMR (CD₃COCD₃—CD₃SOCD₃) 5.68 (2H, d), 7.37 (1H, s), 7.42 (1H, d), 7.75 (6H, m), 7.80–7.95 (9H, m), 8.38 (1H, d).

Step 4: Sodium 1-(((1(R)-(3-(2-(2-chlorothieno[3,2-b]pyridin- 5-yl)-ethenyl)phenyl)-3-(2-(1-hydroxy-1 -methylethyl)phenyl)propyl)thio)methyl)cyclopropaneacetate Using the procedure described in Steps 18 and 19 of Example 1, the phosphonium bromide (0.484 g, 0.91 mmol) of Step 3 was converted in 86% yield to the title compound.

¹H NMR (CDCl₃) of the acid δ0.38–0.61 (4H, m), 1.61 (3H,s), 1.64 (3H, s), 2.20 (2H, m), 2.31–2.45 (2H, m), 2.50 (1H, d, J=14 Hz), 2.62 (1H, d, J=13 Hz), 2.90 (1H, m), 3.19 (1H, m), 4.00 (1H, t), 7.08–7.19 (2H, m), 7.21–7.48 (8H, m), 7.57 (1H, d, J=16 Hz), 7.69 (1H, s), 7.96 (1H, d, J=8.2 Hz).

EXAMPLE 7

Sodium 1-(((1(R)-(3-(2-(2-fluorothieno[3,2-b]pyridin-5 -yl)ethenyl)phenyl)-3-(2-(1-hydroxy-1-methylethyl) phenyl)propyl)thio)methyl)cyclopropaneacetate Step 1: 2-Fluoro-5-methylthieno[3,2-b]pyridine To a solution of 2.23 g (15 mmol) of 5-methylthieno[3,2-b]pyridine in 35 ml of THF was added 80 µl (0.6 mmol) of diisopropylamine, followed by addition of 10.3 ml of n-butyl lithium (1.4M in hexane) at −78° C. After stirring at −78° C. for 15 min, a solution of 6.9 g (22 mmol) of N-fluoro bis(benzenesulfonyl)amide in 30 mL of THF was added. Reaction was stirred at −78° C. for 1 hr, warmed up to 0° C., and stirred at 0° for 2 hr. Aqueous workup with ammonium chloride and ethyl acetate, followed by chromatographic purification with toluene/ethyl acetate=6:1 gave 1.18 g (47%) of the title compound.

¹H NMR (CDCl₃) δ7.87(1H, d, J=8 Hz), 7.11(1H, d, J=8 Hz), 6.88(1H, d, J=2.5 Hz), 2.64(3H, s).

Another product, identified as 2-(phenylsulfonyl)-5-methylthieno[3,2-b]pyridine, was also isolated.

¹H NMR (CDCl₃) δ2.69 (3H, s), 7.25 (1H, d), 7.27 (1H, s), 7.50–7.65 (3H, m), 8.05 (3H, m).

Step 2: Sodium 1-(((1(R)-(3-(2-(2-fluorothieno[3,2-b]pyridin-5 -yl)-ethenyl)phenyl)-3-(2-(1-hydroxy-1 -methylethyl)phenyl)propyl)thio)methyl)cyclopropaneacetate Using the procedure described in Steps 2–4 of Example 6, the title compound was prepared.

¹H NMR δ0.24–0.45(4H, m), 1.5–1.53(6H, 2s), 1.13–2.35(2H, m), 2.35(2H, s), 2.6(2H, d, J=5 Hz), 2.77–2.85(1H, m), 3.1–3.25(1H, m), 4.03(1H, t, J=7.5 Hz), 7.0–7.07(4H, m), 7.3–7.37(4H, m), 7.46(1H, s) 7.49(1H, d, J=8 Hz), 7.68–771(1H, d, J=9 Hz), 7.76(1H, s), 8.17(1H, d, J=8 Hz).

EXAMPLE 8

Sodium 1-(((1(R)-(3-(2-(2,3-difluorothieno[3,2-b]pyridin-5 -yl)ethenyl)phenyl)-3-(2-(1-hydroxy-1-methylethyl) phenyl)propyl)thio)methyl)cyclopropaneacetate Step 1: 2,3-Difluoro-5-methylthieno[3,2-b]pyridine To a −78° C. solution of 2-fluoro-5-methylthieno[3,2-b]pyridine (Example 7, Step 1) (1.00 g, 6,00 mmol) in 30 mL of THF was added n-butyllithium (6.6 mmol). After 5 min the temperature was raised to −20° C. and perchloryl fluoride was bubbled through for 0.5 min. The reaction mixture was brought to 0° C., poured in a 10% solution of NaHCO₃ and extracted with EtOAc. The solvents were evaporated and the title compound was purified by flash chromatography on silica with EtOAc:Hexane 1:3 to yield 0.376 g (34%).

¹H NMR (CDCl₃) δ2.67 (3H, s), 7.81 (1H, d), 7.84 (1H, d).

Step 2: 5-Bromomethyl-2,3-difluorothieno[3,2-b]pyridine

The product of Step 1 (0.518 g, 2.8 mmol), N-bromosuccinimide (0.548 g, 3.08 mmol), and benzoyl peroxide (0.034 g, 0.14 mmol) in 12 mL of carbon tetrachloride were refluxed under a sun lamp for 2 hr. After cooling to room temperature, the solvent was removed and the title bromide was purified by flash chromatography on silica with toluene to yield 0.341 (46%).

¹H NMR (CDCl₃) δ4.67 (2H, s), 7.49 (1H, d), 7.98 (1H, dd).

Step 3: ((2,3-Difluorothieno[3,2-b]pyridin-5-yl)methyl)triphenylphosphonium bromide A solution of bromide (0.335 g, 1.27 mmol) of Step 2 and triphenylphosphine (0.366 g, 1.40 mmol) in 4 mL of acetonitrile was stirred at r.t. for 20 hr. The solvent was removed and the crude solid was swished in acetone:ether 1:1 to yield 0.493 g (74%) of the title phosphonium salt.

¹H NMR (CDCl₃) δ5.96 (2H, d), 7.63–8.04 (16H, m), 8.21 (1H, d).

Step 4: Methyl 1-(((1(R)-(3-(2-(2,3-difluorothieno[3,2-b] pyridin-5-yl)ethenyl)phenyl)-3-(2-(1-hydroxy-1 -methylethyl)phenyl)propyl)thio)methyl)cyclopropaneacetate Using the procedure described in Step 18 of Example 1, the phosphonium bromide (0.484 g, 0.91 mmol) of Step 3 was convened in 66% yield to the title compound.

¹H NMR (CD₃COCD₃) δ0.45(4H, m), 1.55(6H, s), 2.20(2H, m), 2.40(2H, AB system), 2.55(2H, s), 2.89(1H, m), 3.18(1H, dr), 3.57(3H, s), 3.90(1H, s), 4.05(1H, t), 7.10–7.25(3H, m), 7.35–7.45(4H, m), 7.56(1H, m), 7.62(1H, d), 7.75(1H, s), 7.85(1H, d), 8.23(1H, d).

Step 5: Sodium 1-(((1(R)-(3-(2-(2,3-difluorothieno[3,2-b] pyridin5-yl)ethenyl)phenyl)-3-(2-(1-hydroxy-1 -methylethyl)phenyl)propyl)thio)methyl)cyclopropaneacetate To a solution of the methyl ester (0.200 g, 0.33 mmol) of Step 4 in a 1:1 mixture of THF:H20 (1.6 mL) was added LiOH (0.016 g, 0.66 mmol) solid. After 2 days of stirring the solution was poured in a 10% solution of NH₄OAc and extracted with EtOAc. The organic solvents were evaporated and the crude oil purified by flash chromatography on silica with EtOAc:Hexane 4:6 with 2% of acetic acid to yield 0.183 g (94%) of the corresponding carboxylic acid. This acid was dissolved in ethanol and 1 equivalent of sodium hydroxide was added. The solvents were removed and the resulting oil taken in water and lyophilized to yield 0.183 g (96%) of the title compound.

Anal. Calcd. for $C_{33}H_{32}F_2NNaO_3S_2.2H_2O$: C, 60.80; H, 5.58; N, 2.5 Found: C, 60.85; H, 5.11; N, 2.14.

EXAMPLE 9

Sodium 1-(((1(R)-(3-(2-(2-chloro-3-fluorothieno[3,2-b]pyridin-5-yl)ethenyl)-phenyl)-3-(2-(1-hydroxy-1-methylethyl)phenyl)propyl)thio)methyl)cyclopropaneacetate Step 1: 2-Chloro-3-fluoro-5-methylthieno[3,2-b]pyridine To a solution of 550 mg (3 mmol) of 2-chloro-5-methylthieno-[3,2-b]pyridine (Example 6, Step 1) and 14 µL (0.1 mmol) of diisopropylamine in 12 mL of THF was added 2.3 mL of n-butyl lithium (1.4M in hexane) at −78° C. After stirring for 10 min at −78° C., $FClO_4$ gas was bubbled into the reaction for 15 sec. The deep red color turned immediately to yellow. The reaction was stirred at −78° C. for 15 min, warmed up to 0° C., and stirred for 15 min. Aqueous ammonium chloride was added and the product was extracted with ethyl acetate. Chromatographic purification on silica gel with toluene/ethyl acetate=10:1 gave 340 mg (57%) of title product.

$^1$H NMR ($CDCl_3$) δ7.88 (1H, dd, J=8 Hz, J'=0.5 Hz), 7.20 (1H, d, J=8 Hz), 2.70 (3H, s).

Step 2: 5-(Bromomethyl)-2-chloro-3-fluorothieno[3,2-b]pyridine

Using the procedure described in Step 2 of Example 8, the title compound was prepared.

$^1$H NMR ($CDCl_3$) δ8.0 (1H, dd, J=8 Hz, J'=0.5 Hz), 7.52 (1H, d, J=8 Hz), 4.69 (2H, s).

Step 3: ((2-chloro-3-fluorothieno[3.2-b]pyridine-5-yl)methyl)triphenylphosphonium bromide Using the procedure described in Step 3 of Example 8, the title compound was prepared.

$^1$H NMR (DMSO-$d_6$) δ8.46 (1H, d, J=8 Hz), 7.88–7.68 (15H, m), 7.42 (1H, d, J=8 Hz), 5.67 (2H, d, J=14 Hz).

Step 4: Methyl 1-(((1(R)-(3-(2-(2-chloro-3-fluorothieno[3,2-b] pyridin-5-yl)ethenyl)phenyl)-3-(2-(1-hydroxy-1 -methylethyl)phenyl)propyl)thio)methyl)cyclopropaneacetate Using the procedure described in Step 18 of Example 1, the title compound was prepared from the phosphonium salt of Step 3.

$^1$H NMR ($CDCl_3$) δ7.95(d, J=8Hz, 1H), 7.70(d, J=14 Hz, 1H), 7.60(s, 1H), 7.49(m, 2H), 7.38–7.08(m, 7H), 3.92(t, J=7 Hz, 1H), 3.60(s, 3H), 3.12(m, 1H), 2.85(m, 1H), 2.49(s, 2H), 2.38(s, 2H), 2.20(m, 2H), 1.60(s, 3H), 1.58(s, 3H), 0.50(m, 4H).

Step 5: Sodium 1-(((1(R)-(3-(2-(2-chloro-3-fluorothieno[3,2-b] pyridin-5-yl)ethenyl)phenyl)-3-(2-(1-hydroxy-1 -methylethyl)phenyl)propyl)thio)methyl)cyclopropaneacetate Using the procedure described in Step 19 of Example 1, the methyl ester of Step 4 was convened to the title compound.

$^1$H NMR ($CDCl_3$) δ7.90(d, J=8 Hz, 1H), 7.66(d, J=5, 1H), 7.62(d, J=9 Hz, 1H), 7.50(d, J=9 Hz, 1H), 7.42(m, 1H), 7.35–7.05(m, 7H), 3.97(t, J=7 Hz, 1H), 3.16(m, 1H), 2.88(m, 1H), 2.58–2.34(m, 4H), 2.18(m, 2H), 1.60(s, 3H), 1.59(s, 3H), 0.47(m, 4H).

EXAMPLE 10

Sodium 1-(((1(R)-(3-(2-(3-chloro-2-fluorothieno[3,2-b]pyridin-5-yl)ethenyl)phenyl)-3-(2-(1-hydroxy-1-methylethyl)phenyl)propyl)thio)methyl)cyclopropaneacetate Step 1: 3-Chloro-2-fluoro-5-methylthieno[3,2-b]pyridine To a solution of 461 mg (2.74 mmol) of 2-fluoro-5-methylthieno [3.2-b]pyridine (Example 7, Step 1) and 14 µl (0.1 mmol) of diisopropylamine in 12 mL of THF was added 2.15 mL of n-butyl lithium (1.4M in hexane) at −78° C. After stirring at −78° C. for 10 min, a solution of 585 mg (4.4 mmol) of N-chlorosuccinimide in 10 mL of THF was added at −78° C. The mixture was stirred at −78° C. for 20 min, warmed up to 0° C., stirred at 0° C. for 30 min, and then partitioned between aqueous ammonium chloride and ethyl acetate. Chromatographic purification on silica gel with hexane/ethyl acetate=8:1 gave 350 mg (63%) of the title product.

$^1$H NMR ($CDCl_3$) δ7.88(d, J=8, 1H), 7.18(d, J=8, 1H), 2.70(s, 3H).

Step 2: Sodium 1-(((1(R)-(3-(2-(3-chloro-2-fluorothieno[3,2-b] pyridin-5-yl)ethenyl)phenyl)-3-(2-(1-hydroxy-1 -methylethyl)phenyl)propyl)thio)methyl)cyclopropaneacetate Following the procedure of Steps 2–5 of Example 8, the title compound was prepared from the product of Step 1.

$^1$H NMR ($CD_3COCD_3$) δ0.2–0.55 (4H, m), 1.5 (3H, s), 1.55 (3H, s), 2.1 (2H, m), 2.25 (2H, s), 2.65 (2H, s), 2.70–2.85 (1H, m), 3.15–3.25 (1H, m), 4.05 (1H, t, J=7.5 Hz), 6.95–7.1 (3H, m), 7.3–7.4 (4H, m), 7.5 (1H, d, J=7.5 Hz), 7.65 (1H, d, J=7.5 Hz), 7.7 (1H, s), 7.85 (1H, d, J=15 Hz), 8.28 (1H, d, J=7.5 Hz).

EXAMPLE 11

Sodium 1-(((1(R)-(3-(2-(2-(phenylsulfonyl)thieno[3,2-b]pyridin-5-yl)ethenyl)phenyl)-3-(2-(1-hydroxy-1-methylethyl)phenyl)propyl)thio)methyl)cyclopropaneacetate Following the procedure of Steps 2–4 of Example 6, the title compound was prepared from 2-(phenylsulfonyl)-5-methylthieno[3,2-b]pyridine isolated in Step 1 of Example 7.

$^1$H NMR of the acid ($CDCl_3$) δ0.36–0.53 (3H, m), 0.58 (1H, m), 1.61 (3H, s), 1.63 (3H, s), 2.05 (1H, s), 2.19 (2H, m), 2.34–2.52 (3H, m), 2.60 (1H, d), 2.90 (1H, m), 3.19 (1H, m), 4.0 (1H, t), 7.07–7.20 (3H, m), 7.23–7.38 (4H,m), 7.43 (1H, m), 7.50–7.70 (6H, m), 8.03–8.13 (4H, m). Anal. Calc'd. for $C_{39}H_{38}NNaO_5S_3.3.6H_2O$: C, 59.69; H, 5.81; N, 1.78 Found: C, 59.68; H, 5.70; N, 1.52.

EXAMPLE 12

Sodium 1-(((1(R)-(3-(2-(2,3-dichlorofuro[3,2-b]pyridin-5-yl)ethenyl)phenyl)-3-(2-(1-hydroxy-1-methylethyl)phenyl)propyl)thio)methyl)cyclopropaneacetate Step 1: 2-(Trimethylsilyl)-6-methylfuro[3,2-b]pyridine A mixture of 2-iodo-6-methylpyridine-3-ol (20 g, 85 mmol), CuI (2.1 g, 11 mmol), trimethylsilyl acetylene (23.4 g, 238 mmol), and bis(triphenylphosphine)palladium(II)chloride (5.37 g, 7.65 mmol) in Et$_3$N (380 mL) was heated to reflux for 20 hr. The mixture was cooled and diluted with ether and filtered through celite. The filtrate was concentrated in vacuo and the residue was chromatographed on silica gel (eluted with 10% EtOAc in hexane) to give 15 g (86%) of the title compound.

$^1$H NMR (CD$_3$COCD$_3$) δ0.40 (9H, s), 2.54 (3H, s), 7.12 (1H, d, J=8 Hz), 7.14 (1H, s), 7.75 (1H, d, J=8 Hz).

Step 2: 2,3-Dichloro-5-methylfuro[3,2-b]pyridine

To a solution of 2-trimethylsilyl-5-methylfurano[3,2-b]pyridine (1.05 g, 5.15 mmol) in CH$_2$Cl$_2$ (16 mL) at 0° C. was added trichloroisocyanuric acid (1.2 g, 5.15 mmol). The mixture was stirred at 0° C. for 30 rain and then at r.t. for 20 hr. A solution of 30% EtOAc in hexane was added. The resulting mixture was filtered through a short bed of silica gel and eluted with more 30% EtOAc in hexane. Evaporation of the filtrate gave 1.0 g (96%) of the title compound.

$^1$H NMR (CD$_3$COCD$_3$) δ2.61 (3H, s), 7.33 (1H, d, J=8 Hz), 7.84 (1H, d,J=8 Hz).

Step 3: ((2,3-Dichlorofuro[3,2-b]pyridin-5-yl)methyl)triphenylphosphonium bromide To a solution of 2,3-dichloro-5-methylfurano[3,2-b]pyridine (0.5 g, 2.47 mmol) in CCl$_4$ (15 mL) was added N-bromosuccinimide (0.44 g, 2.47 mmol) and benzoyl peroxide (2 mg). The mixture was stirred and photolyzed using a sun lamp for 1 hr. The resulting mixture was cooled and filtered through celite. Evaporation of the filtrate gave an oil which was then dissolved in CH$_3$CN (10 mL). Triphenylphosphine (1.29 g, 4.94 mmol) was added and the mixture was stirred at r.t. for 20 hr. The solvent was removed and the residue was triturated with ether to afford 1 g (77%) of the title compound after filtration.

$^1$H NMR (CDCl$_3$) δ5.9 (2H, d, J=15 Hz), 7.55–8.0 (16H, m), 8.2 (1H, d,J=9 Hz).

Step 4: Methyl 1-(((1(R)-(3-(2-(2,3-dichlorofuro[3,2-b]pyridin-5 -yl)-ethenyl)phenyl)-3-(2-(1-hydroxy-1 -methylethyl)phenyl)propyl)thio)methyl)cyclopropaneacetate Using the procedure described in Step 18 of Example 1. The phosphonium salt of Step 3 was converted to the title compound in 92% yield.

$^1$H NMR (CD$_3$COCD$_3$) a 0.40–0.50(4H, m), 1.53(6H, s), 2.20(2H, m), 2.40(2H, AB system), 2.57(2H, s), 2.90(1H, m), 3.15(1H, s), 3.59(3H, s), 3.9(1H, s), 4.05(1H, t), 7.10(3H, m), 7.40(4H, m), 7.55(1H, m), 7.62(1H, d), 7.74–7.80(2H, m), 7.91(1H, d).

Step 5: Sodium 1-(((1(R)-(3-(2-(2,3-dichlorofuro[3,2-b]pyridin-5 -yl)ethenyl)phenyl)-3-(2-(1-hydroxy-1 -methylethyl)phenyl)propyl)thio)methyl)cyclopropaneacetate Using the procedure described in Step 19 of Example 1, the methyl ester of Step 4 (0.176 g, 0.27 mmol) was convened in 86% yield to the title compound.

Anal. Calcd. for C$_{33}$H$_{32}$C$_2$NNaO$_4$S.1.5H$_2$O: C, 60.08; H, 5.36; N, 2.12; Cl, 10.75 Found: C, 60.04; H, 5.01; N, 2.06; C$_{1, 11.07}$.

EXAMPLE 13

Sodium 1-(((1(R)-(3-(2-(3-chlorofuro[3,2-b]pyridin-5 -yl)ethenyl)phenyl)-3-(2-(1-hydroxy-1-methylethyl) phenyl)propyl)thio)methyl)cyclopropaneacetate Step 1: 3-Chloro-5-methylfuro[3,2-b]pyridine To a solution of 2,3-dichloro-5-methylfuro[3,2-b]pyridine (0.661 g, 3.27 mmol) (Example 12, Step 2) in 16 mL of THF was added a 1.7M solution of t-butyllithium (4.04 mL, 6.87 mmol). After 30 min the solution was quenched at −78° C. with methanol and a solution of NH$_4$C$_1$. The reaction was brought to room temperature and extracted with EtOAc. The organic solvents were evaporated and the title compound was purified by flash chromatography on silica with EtOAc:hexane 1:4 to yield 0.444 g (81%).

$^1$H NMR (CDCl$_3$) δ2.71 (3H, s), 7.16 (1H d), 7.65 (1H, d), 7.84 (1H, s).

Step 2: 5-Bromomethyl-3-chlorofuro[3,2-b]pyridine

Using the procedure described in Step 2 of Example 8, 3-chloro-5-methylfuro[3,2-b]pyridine (0.245 g, 1.46 mmol) was convened in 46% yield to the title compound.

$^1$H NMR(CDCl$_3$) δ4.70 (2H, s), 7.50 (1H, d), 7.78 (1H, d), 7.90 (1H, s).

Step 3: ((3-Chlorofuro[3,2-b]pyridin-5-yl)methyl)triphenylphosphonium bromide

Using the procedure described in Step 3 of Example 8, 5-bromomethyl-3-chlorofurano[3,2-b]pyridine (0.162 g, 0.65 mmol) was convened in 86% yield to the title compound.

$^1$H NMR (CDCl$_3$) δ5.90 (2H, m), 7.55–8.00 (17H, m), 8.25 (1H, d).

Step 4: Methyl 1-(((1(R)-(3-(2-(3-chlorofuro[3,2-b]pyridin-5 -yl)ethenyl)phenyl)-3-(2-(1-hydroxy-1 -methylethyl)phenyl)propyl)thio)methyl)cyclopropaneacetate Using the procedure described in Step 18 of Example 1, ((3-chlorofuro[3,2-b ]pyridin-5-yl )methyl)triphenylphosphonium bromide (0.273 g, 0.53 mmol) was convened in 75% yield to the title compound.

$^1$H NMR (CD$_3$COCD$_3$) δ0.40–0.55(4H, m), 1.55(6H, s), 2.23(2H, m), 2.40(2H, AB system), 2.58(2H, s), 2.90(1H, m), 3.20(1H, m), 3.60(3H, s), 3.90(1H, s), 4.05(1H, t), 7.13(2H, m), 7.40–7.60(6H, m), 7.65(1H, d), 7.70–7.85(2H, m), 7.95(1H, d), 8.30(1H, s).

Step 5: Sodium 1-(((1(R)-(3-(2-(3-chlorofuro[3,2-b]pyridin-5 -yl)ethenyl)phenyl)-3propyl)thio)methyl)cyclopropaneacetate Using the procedure described in Step 5 of Example 8, the methyl ester (0.160 g, 0.28 mmol) of Step 4 was convened in 83% yield to the title compound.

Anal. Calcd. for C$_{33}$H$_{33}$ClNNaOS$_4$.2H$_2$O: C, 62.49; H, 5.89; N, 2.21; C$_{1, 5.59}$ Found: C, 62.23; H, 5.33; N, 2.20; Cl, 5.34.

EXAMPLE 14

Sodium (R) 1-((3-(2-bromophenyl)-1-(3-(2-(2,3-dichlorothieno [3,2-b] pyridin-5-yl)ethenyl)phenyl)propoxy)methyl) cyclopropaneacetate Step 1: 3-(2-bromophenyl)-1-(3-(((2 -tetrahydropyranyl)oxy)methyl)phenyl)-1-propanone A mixture of the allylic alcohol of Example 1, Step 11, (30.14 g, 121 mmol), 1,2-dibromobenzene (16 mL), Pd(OAc)$_2$ (830 mg), LiCl (5.38 g), LiOAc.2H$_2$O (31.6 g), and Bu$_4$NCl (67.96 g) in 240 mL of DMF was degassed and heated to 85° C. under N$_2$ for 30 min and at 90° C. for 45 min. It was then added to ice and 25% aq. NH$_4$OAc (2 L). The title ketone was extracted in EtOAc, dried over Na$_2$SO$_4$ and purified by flash chromatography on silica with EtOAc:hexane 10:90; yield: 29.53 g (60%).

$^1$H NMR (CDCl$_3$) δ7.97(1H, s), 7.90(1H, d), 7.57(2H, t), 7.45(1H, dd), 7.32(1H, dd), 7.24(1H, dd), 7.09(1H, m), 4.83(1H, d), 4.74(1H, t), 4.55(1H, d), 3.92(1H, m), 3.58(1H, m), 3.32(2H, m), 3.20(2H, m), 1.95–1.45(6H, m).

Step 2: 3-(2-bromophenyl-1(R)-(3-(((2 -tetrahydropyranyl)oxy)methyl)phenyl)-1-propanol To a solution of the ketone of Step 1 (29.00 g, 72 mmol) in 260 mL of anhyd. THF at −55° C. (temperature of the reaction mixture) was added dropwise a solution of (S)-tetrahydro-1-methyl-3,3-diphenyl1H, 3H-pyrrolo[1,2-c][1, 3,2]oxazaborole (4.07 g, 0.2 equiv.; J. Org. Chem., 56, 751 (1991)) in 70 mL of THF, followed by 1.0M borane in THF (75 mL). The mixture was then allowed to warm to −20° C. over 3 hr. It was then cooled to −45° C., quenched with 10% aq. diethanolamine, and warmed to room temperature. 25% Aq. NH$_4$OAc was then added and the chiral alcohol was extracted in EtOAc, dried over Na$_2$SO$_4$, and filtered through silica with EtOAc:toluene 5:95 to 10:90; yield: 27.52 g, 94%.

$^1$H NMR (CDCl$_3$) δ7.53(1H, d), 7.40–7.16(6H, m), 7.05(1H, m), 4.80(1H, d), 4.72(2H, m), 4.50(1H, d), 3.93(1H, m), 3.55(1H, m), 2.90(1H, m), 2.80(1H, m), 2.08(2H, m), 1.95(1H, d, OH), 1.90– 1.48(6H, m).

Step 3: Methyl 2-((3-(2-bromophenyl)-1(R)-(3-(((2 -tetrahydropyranyl)oxy)methyl)phenyl)propoxy)methyl)propenoate At 0° C., 95% NaH (2.4 g, 100 mmol) was added portionwise to a stirred solution of the alcohol of Step 2 (29.5 g, 73 mmol) in 400 mL of DMF and the mixture was stirred at 0° C. for 1 hr. Methyl 2-(bromomethyl)acrylate (10 mL, 88 mmol) was then added and the mixture was stirred at 0° C. for 8 hr. and at room temperature overnight. It was quenched with saturated aq. NH$_4$Cl and the product was extracted in ether, washed with brine, dried over Na$_2$SO$_4$, and purified by flash chromatography with EtOAc:hexane 1:5; yield: 20.0 g (82%).

$^1$H NMR (CDCl$_3$) δ7.50(1H, d, J=7.5 Hz), 7.37–7.17(6H, m), 7.04(1H, m), 6.33(1H, br, s), 5.97(1H, br, s), 4.79(1H, d, J=11 Hz), 4.70(1H, m), 4.50(1H, d, J=11 Hz), 4.35(1H, dd), 4.12(1H, d), 4.02(1H, d), 3.92(1H, m), 3.73(3H, s), 3.55(1H, m), 2.90(1H, m), 2.78(1H, m), 2.12(1H, m), 2.00(1H, m), 1.90–1.50(6H, m).

Step 4: 2-((3-(2-bromophenyl)-1(R)-(3-(((2 -tetrahydropyranyl)oxy)methyl)phenyl)propoxy)methyl)-2-propen-1-ol To a solution of the ester of Step 3 (29.69 g, 59 mmol) in 300 mL of CH$_2$Cl$_2$ at −78° C. was added slowly a solution of diisobutylaluminum hydride 1.5M in toluene (99 mL, 149 mmol) and the mixture was stirred at −78° C. for 30 min. 2M Tartaric acid was then added and the solution was neutralized with 10 N NaOH. The product was extracted in EtOAc, dried over Na$_2$SO$_4$, and concentrated to give 26.90 g, 96%, of the title alcohol.

$^1$H NMR (CDCl$_3$) δ7.52(1H, d), 7.38–7.13(6H, m), 7.03(1H, m), 5.14(2H, AB system), 4.80(1H, d), 4.74(1H, t), 4.53(1H, d), 4.33(1H, dd), 4.30(2H, AB system), 3.97(1H, d), 3.92(1H, m), 3.88(1H, d), 3.55(1H, m), 2.90(1H, m), 2.75(1H, m), 2.19–1.50(9H, m).

Step 5: 1-((3-(2-bromophenyl)-1(R)-(3-(((2 -tetrahydropyranyl)oxy)methyl)phenyl)propoxy)methyl)cyclopropanemethanol At 0° C., Pd(OAc)$_2$ (500 mg) and ~0.4M CH$_2$N$_2$ in ether (1.84) were added portionwise and simultaneously to a solution of the allylic alcohol of Step 4 (20.45 g, 43.0 mmol) in 80 mL of THF. When the reaction was complete, the mixture was filtered through a small pad of silica and concentrated. The residue was purified by flash chromatography on silica with EtOAc:toluene 15:85 to give 12.40 g (59%) of the title product.

$^1$H NMR (CDCl$_3$) δ7.51(1H, d), 7.38–7.14(6H, m), 7.05(1H, m), 4.79(1H, 2d), 4.72(1H, br s), 4.50(1H, 2d), 4.25(1H, dd), 3.92(1H, 3.65(1H, m), 3.54(2H, m), 3.28(2H, AB system), 2.90(1H, m), 2.78(1H m), 2.65(1H, m), 2.18–1.50(8H, m), 0.55(2H, m), 0.43(2H, m).

Step 6: 1-((3-(2-bromophenyl)-1(R)-(3-(((2 -tetrahydropyranyl)oxy)methyl)phenyl)propoxy)methyl)cyclopropaneacetonitrile Methanesulfonyl chloride (2.90 mL, 37.5 mmol) and triethylamine (6.50 mL, 46.6 mmol) were added to a solution of the alcohol of Step 5 (15.30 g, 31.3 mmol) in 200 mL of CH$_2$Cl$_2$ at −40° C. and the solution was stirred at −40° C. for 30 min and at 0° C. for 1 hr. Aq. saturated NaHCO$_3$ was then added and the mesylate was extracted in CH$_2$C$_{12}$, dried over Na$_2$SO$_4$, concentrated, and stripped twice with toluene. To a solution of this mesylate in 240 mL of anhydrous dimethylsulfoxide was added NaCN (7.69, 157 mmol) and the mixture was stirred at room temperature overnight. Water (1 L) was then added, followed by 250 mL of saturated NaHCO$_3$ and the product was extracted in ether, washed with brine, dried over Na$_2$SO$_4$, and purified by flash chromatography on silica with EtOAc:toluene 5:95; yield: 13.43 g (86%).

$^1$H NMR (CDCl$_3$) δ7.54(1H, d), 7.38–7.15(6H, m), 7.06(1H, m), 4.80(1H, d), 4.72(1H, m), 4.50(1H, d), 4.26(1H, rid), 3.94(1H, m), 3.57(1H, m), 3.32(1H, d), 3.09(1H, d), 2.93(1H, m), 2.81(1H, m), 2.75(1H, d), 2.45(1H, d), 2.18–1.50(8H, m), 0.68–0.49(4H, m).

Step 7: 1-((3-(2-bromophenyl)-1(R)-(3-(((2 -tetrahydropyranyl)oxy)methyl)phenyl)propoxy)methyl)cyclopropaneacetic acid A mixture of the nitrile of Step 6 (13.22 g, 26.5 mmol), 8N KOH (330 mL), and EtOH (130 mL) was heated to reflux for 17 hr. 25% Aq. NH$_4$OAc (500 mL) and AcOH (190 mL) were than added at room temperature (to give pH~6) and the product was extracted in EtOAc and dried over Na$_2$SO$_4$. Hash chromatography of the residue with EtOAc:toluene:A-cOH 10:90:1 afforded 10.34 g (75% yield) of the title acid.

$^1$H NMR (CDCl$_3$) δ7.52(1H, d), 7.35–7.10(6H, m), 7.06(1H, m), 4.79(1H, d), 4.74(1H, m), 4.54(1H, d), 4.38(1H, m), 3.94(1H, m), 3.60(1H, m), 3.39(1/2H, d), 3.28(1/2H, d), 3.20(1/2H, d), 3.03(1/2H, d), 2.89(1H, m), 2.78(1H, m), 2.78(1/2H, d), 2.63(1/2H, d), 2.45(1/2H, d), 2.28(1/2H, d), 2.18(1H, m), 2.05(1H, m), 1.95–1.50(6H, m), 0.62– 0.43(4H, m).

Step 8: Methyl 1-((3-(2-bromophenyl)-1(R)-(3 -(hydroxymethyl)phenyl)propoxy)methyl)cyclopropaneacetate The acid of Step 7 (1.816 g, 3.51 mmol) was esterified with CH$_2$N$_2$ at 0° C. in ether:THF. The excess CH$_2$N$_2$ was quenched with AcOH and the product was concentrated and stripped with toluene twice. This ester was dissolved in 20 mL MeOH and then pyridine (7 μL) and pyridinium p-toluenesulfonate (220 mg, 0.88 mmol) were added. After 6 days of stirring, the solvent was evaporated. 25% aq. NH$_4$OAc was then added and the product was extracted in EtOAc, dried over Na$_2$SO$_4$, and purified by flash chromatography on silica with EtOAc:hexane 30:70; yield: 1.53 g, (97%).

$^1$H NMR (CDCl$_3$) δ7.50(1H, d), 7.35–7.18(6H, m), 7.04(1H, m), 4.70(2H, d), 4.21(1H, dd),3.63(3H, s), 3.18(2H, AB system), 2.93(1H, m), 2.78(1H, m), 2.45(2H, s), 2.08(1H, m), 1.98(1H, m), 1.95(1H, t. OH), 0.58–0.40(4H, m).

Step 9: Sodium (R) 1-((3-(2-bromophenyl)-1-(3-(2-(2,3 -dichlorothieno[3,2-b ]pyridin-5-yl)ethenyl)phenyl)propoxy)methyl)cyclopropaneacetate Using the procedure of Example 1, Steps 17–19, but using ((2,3-dichlorothieno[3,2-b]pyridine-5-yl )methyl)triphenylphosphonium bromide (Example 4, Step 3) in Step 18, the title product was prepared from the ester of Step 8.

$^1$H NMR (free acid, CDCl$_3$) δ8.02(1H, d), 7.68(1H, d), 7.60–7.48(4H, m), 7.43–7.34(2H, m), 7.28–7.19(3H, m), 7.07(1H, m), 4.34(1H, dd), 3.38(1H, d), 3.19(1H, d), 2.93(1H, m), 2.80(1H, m), 2.70(1H, d), 2.49(1H, d), 2.18(1H, m), 2.08(1H, m), 0.64–0.47(4H, m).

EXAMPLE 15

Sodium 1-((1(R)-(3-(2-(2,3-dichlorothieno[3,2-b]pyridin-5-yl)ethenyl)phenyl)-3-(2-(1-hydroxy-1-methylethyl) phenyl)propoxy)methyl)cyclopropaneacetate Step 1: Methyl 1-((3-(2-(1-hydroxy-1-methylethyl)phenyl)-1 (R)-(3-(((2-tetrahydropyranyl)oxy)methyl)phenyl)propoxy)methyl)cyclopropaneacetate To a frozen solution of the acid of Example 14, Step 7 (2.216 g, 4.28 mmol) in 30 mL of THF at −100° C. was added 1.6M BuLi in hexanes (5.9 mL) and the mixture was stirred at −78° C. for 30 min. Acetone (630 μL, 8.6 mmol) was then added and the mixture was stirred at −78° C. for 1 hr. and was then allowed to warm to −20° C. Saturated aq. NH$_4$Cl was then added and the products were extracted in EtOAc. At 0° C., diazomethane ~0.5M was added. When the esterification was completed, the excess of CH$_2$N$_2$ was quenched with AcOH. The solution was dried over Na$_2$SO$_4$, concentrated and stripped with toluene. Hash chromatography of the residue with EtOAc:hexane 15:85 to 35:65 afforded first, the reduced starting material (desbromo), second, the product of addition of acetone α to the ester and third, the title product.

$^1$H NMR (CDCl$_3$) δ7.40(1H, d), 7.34–7.08(7H, m), 4.80(1H, d), 4.72(1H, m), 4.50(1H, d), 4.33(1H, dd), 3.93(1H, m), 3.64(3H, s), 3.57(1H, m), 3.30(1H, d), 3.20(1H, m), 3.14(1H, d), 2.96(1H, m), 2.58(1H, d), 2.33(1H, d), 2.17–1.48(8H, m), 1.65(6H, 2s), 1.27(1H, s, OH), 0.51 (4H, m).

Step 2: Sodium 1-((1(R)-(3-(2-(2,3-dichlorothieno[3,2-b] pyridin-5-yl)ethenyl)-phenyl)-3-(2-(1-hydroxy-1 -methylethyl)phenyl)propoxy)methyl)cyclopropaneacetate Using the procedure of Example 1, Steps 16–19, but using ((2,3-dichlorothieno[3,2-b ]pyridin-5-yl)methyl)triphenylphosphonium bromide (Example 4, Step 3) in Step 18, the title sodium salt was prepared from the ester of Step 1.

$^1$H NMR (free acid, CDCl$_3$) δ8.00(1H, d), 7.70(1H, d), 7.60–7.50(3H, m), 7.42–7.30(3H, m), 7.26(2H, m), 7.20–7.08(2H, m), 4.45(1H, dd), 3.30(1H, m), 3.31(1H, d), 3.20(1H, d), 2.95(1H, m), 2.58(1H, d), 2.38(1H, d), 2.18(1H, m), 2.07(1H, m), 1.70(6H, 2s), 0.64–0.47(4H,

EXAMPLE 16

Sodium 1-(((3-(4-cyclopropylphenyl)-1(R)-(3-(2-(2,3-dichlorothieno[3,2-b ]pyridin-5-yl)ethenyl)phenyl)propyl)thio)methyl) cyclopropaneacetate Step 1: 3-(1-Hydroxy-2-propen-1-yl)benzonitrile To 3-cyanobenzaldehyde (25 g, 0.190 mmol) in THF (576 mL) was added dropwise at −10° C. vinyl magnesium bromide in THF (202 mL, 0.201 mmol). After 15 min, the reaction mixture was poured on cold 25% aqueous ammonium acetate solution and extracted with EtOAc. The resulting mixture was purified by flash chromatography to provide 17.5 g (60%) of the title product.

Step 2: 3-(1-hydroxy-2-propen-1-yl)benzaldehyde

To the nitrile (Step 1) (17.0 g, 0.107 mmol) in THF (465 mL) at −78° C. was added dropwise a DIBAL solution (157 mL, 0.235 mmol). The resulting mixture was brought slowly to 0° C. After completion, the reaction mixture was poured over 10% aqueous tartaric acid solution (1 L). After stirring for a period of 1 hr., the title product was extracted with EtOAc and purified by flash chromatography (40% to 50% EtOAc in hexane) to afford 15 g (88%) of the aldehyde.

Step 3: 1-(3-(2-(2,3-dichlorothieno[3,2-b]pyridin-5 -yl)ethenyl)phenyl)-2-propen-1-ol To a suspension of the phosphonium salt of Example 4, Step 3, (10 g, 19.4 mmol) in THF (110 mL) at −78° C. was added 1M potassium tert-butoxide in THF (17.8 mL, 17.8 mmol). After 10 min at 0° C., the yellow mixture was brought to room temperature for a period of 15 min and then cooled to −78° C. The aldehyde of Step 2 (2.63 g, 16.23 mmol) in THF (40 mL) was then added and the reaction mixture was stirred 1 hr. at 0° C. and 1 hr. at room temperature. The reaction mixture was neutralized by the addition of 25% aqueous ammonium acetate solution, extracted with EtOAc and purification by flash chromatography afforded 4.0 g (70%) of the olefinic product.

Step 4: 3-(4-cyclopropylphenyl)-1-(3-(2-(2,3 -dichlorothieno[3,2-b ]-pyridin-5-yl)ethenyl)phenyl)propan-1-one Through a mixture of the allylic alcohol of Step 3 (1.0 g, 2.77 mmol), 4-(iodophenyl)cyclopropane (1.35 g, 5.50 mmol), lithium chloride (135 mg), lithium acetate (749 mg), and palladium acetate (50 mg) in DMF (6.98 mL) was bubbled nitrogen. The mixture was heated under nitrogen at 70° C. for a period of 10 min. After work up with 25% aqueous ammonium acetate solution and EtOAc, the organic phase was evaporated to dryness. The resulting solid was worked with acetone to provide 650 mg of the ketone as a white solid. The filtrate was purified on silica gel to give an extra 200 mg of ketone.

Step 5: 3-(4-Cyclopropylphenyl)-1(S)(3-(2-(2,3 -dichlorothieno[3,2-b]-pyridin-5-yl)ethenyl)phenyl)propan-1-ol To a CH$_2$Cl$_2$ solution (4.0 mL) of (1)-B-chlorodiisopinocamphylborane (904 mg, 2.82 mmol) at −30° C. was added a solution of the ketone of Step 4 (45 mg, 0.934 mmol) in CH$_2$Cl$_2$ (4.6 mL). The temperature was brought up slowly to 0° C. over 3 hr. A saturated solution of NH$_4$Cl was then added and the mixture was stirred overnight at room temperature. After neutralization with 25% aqueous NH$_4$OAc solution, the product was extracted with EtOAc. After evaporation, ether was then added to the residue followed by 1N HCl solution. The hydrochloride salt was filtered and washed three times with ether. To a suspension of the salt in water and EtOAc was added 1N NaOH solution and diethanolamine (10%). After evaporation, 270 mg (60%) of the desired chiral alcohol was obtained.

Step 6: 5-(2-(3-(3-(4-cyclopropylphenyl))-1 (S)-(methanesulfonyloxy)propyl)phenyl)ethenyl)-2,3-dichlorothieno[3,2-b]pyridine To a solution of the alcohol (Step 5) (230 mg, 0.47 mmol) in CHCl$_2$ (2.5 mL) was added at −40° C. Et$_3$N (100 μL, 0.717 mmol) and MsCl (45.0 μL, 0.574 mmo.). The resulting mixture was then warmed to 0° C. After a period of 10 min, a saturated solution of NaHCO$_3$ was added. The mesylate was extracted with CH$_2$C$_{12}$, dried over Na$_2$SO$_4$, evaporated and co-distilled two times with toluene and used as such for the next step.

Step 7: Sodium 1-(((3-(4-cyclopropylphenyl)-1(R)-(3-(2-(2,3 -dichlorothieno[3,2-b]pyridin-5-yl)ethenyl)phenyl)propyl)thio)methyl)cyclopropaneacetate To a solution of the thiol acid obtained by hydrolysis of the ester of Step 9, Example 1(63.0 mg, 0.431 mmol) in THF (1.7 mL) was bubbled N$_2$. n-Butyl lithium was then added dropwise over 15 min at −15° C. After a period of 15 min at −15° C., the temperature was brought slowly to −5° C. To the resulting slurry at −20° C. was added a solution of the mesylate (Step 6) (230 mg, 0.411 mmol) in THF (1.7 mL). The temperature was increased slowly to −5° C. then to 0° C. and room temperature. After 2 hours, the clear solution was then quenched by the addition of 25% aqueous $NH_4OAc$ solution, extracted with EtOAc and dried over $Na_2SO_4$. The title product was purified by flash chromatography with 50% EtOAc in hexane followed by 50% EtOAc in hexane with 1% HOAc to provide 160 mg (75%) of material.

$^1$H NMR (300M Hz, $CD_3COCD_3$) δ0.30–0.50(4H, m), 0.60–0.85(4H, m), 1.85(1H, m), 2.15(2H, m), 2.48(2H, s), 2.55(2H, AB system), 2.60(2H, m), 3.95(1H, t), 7.00(4H, AA BB system), 7.30–7.45(3H, m), 7.60(1H, m), 7.68(1H, s), 7.75(1H, d), 7.89(1H, d), 8.49(1H, d).

EXAMPLE 123

Sodium (R) 1-(((3-(2-(1-hydroxy-1-methylethyl)phenyl)-1-(3-(2-(2-methyl-thiazolo[5,4-b]pyridine-5-yl)ethenyl)phenyl)propyl)thio)methyl)cyclopropaneacetate Step 1: N-acetyl 2-chloro-3-pyridinamine To a solution of 2-chloro-3-pyridinamine (14.9 g, 116 mmol) in 300 mL of THF was added $K_2CO_3$ (32 g, 232 mmol) and acetyl chloride (12 mL, 169 mmol) and the mixture was stirred at room temperature overnight. Saturated $NH_4Cl$ was added and the product was extracted in EtOAc, dried over $Na_2SO_4$, and filtered through silica to yield 20.81 g of the title amide.

$^1$H NMR ($CDCl_3$) δ8.73 (1H,d), 8.13 (1H,d), 7.65 (1H,br s, NH), 7.28 (1H,dd), 2.27(3H,s).

Step 2: 2-methylthiazolo[5,4-b]pyridine

Phosphorus pentasulfide (56.5 g) and $Na_2CO_3$ (13.7 g) were mixed together in 400 mL of THF for ~30 min. To this solution, a solution of the product of Step 1 (17.32 g) in 100 mL of THF was added and the mixture was stirred at room temperature overnight. 2M NaOH (500 mL) was added and the mixture was stirred at room temperature for 2 hr. The product was extracted in EtOAc, washed with brine, dried over $Na_2SO_4$, and purified by flash chromatography on silica with EtOAc: toluene 20:80; yield: 12.07 g, (83%).

$^1$H NMR ($CDCl_3$) δ8.54 (1H,d), 8.18 (1H,d), 7.40 (1H, dd), 2.88 (3H,s).

Step 3: 2-methylthiazolo[5,4-b]pyridine N-oxide

To a solution of the product of Step 2 (8.00 g) in 400 mL of $CH_2Cl_2$ was added m-chloroperbenzoic acid (26.0 g) and the mixture was stirred at room temperature overnight. NaOH 0.5M was added and the product was extracted in $CH_2Cl_2$ (6×), dried over $Na_2SO_4$, and purified by flash chromatography on silica with acetone: toluene 70:30 and acetone: toluene: methanol 40:40:20.

$^1$H NMR ($CDCl_3$) 3 8.29 (1H,d), 7.86 (1H,d), 7.38 (1H,dd), 2.88 (3H,s).

Step 4: 5-cyano-2-methylthiazolo[5,4-b]pyridine

To a solution of the product of Step 3 (4.706 g, 28.3 mmol) in 60 mL of $CH_2Cl_2$ was added trimethylsilyl cyanide (7.6 mL, 57 mmol) and the mixture was stirred at room temperature for 30 min. Dimethylcarbamyl chloride (5.2 mL, 56 mmol) was then added and the mixture was heated to reflux overnight. At 0° C., 2N NaOH (60 mL) was added and the mixture was stirred at this temperature one hour. The product was extracted in EtOAc, dried over $Na_2SO_4$, and purified by flash chromatography on silica with EtOAc: toluene 10:90; yield: 4.50 g, (91%).

$^1$H NMR ($CDCl_3$) 3 8.26(1H,d), 7.80(1H,d), 2.93(3H,s).

Step 5: 5-formyl-2-methylthiazolo[5,4-b]pyridine

To a suspension of the product of Step 4 (4.42 g, 25 mmol) in 100 mL of anhyd. THF at −78° C. was added dropwise 1.5M diisobutylaluminum hydride in toluene (40 mL) and the mixture was stirred at −78° C. for 2 hr. A solution of tartaric acid 10% was then added and the mixture was stirred at room temperature for 2 hr, neutralized with 10N NaOH and extracted with EtOAc. The title product was dried over $Na_2SO_4$ and purified by flash chromatography on silica with EtOAc:hexane 20:80 to yield 3.733 g (83%) as a white solid.

$^1$H NMR ($CDCl_3$) δ10.13 (1H,s), 8.33 (1H,d), 8.12 (1H, d), 2.95 (3H,s).

Step 6: 5-(hydroxymethyl)-2-methylthiazolo[5,4-b]pyridine

To a suspension of the product of Step 5 (3.733 g, 21 mmol) in 200 mL of EtOH at 0° C. was added $NaBH_4$ (800 mg, 21 mmol) and the mixture was stirred at 0° C. for 5 min. Saturated aq. $NH_4Cl$ was then added slowly and the product was extracted in EtOAc:THF 1:1, dried over $Na_2SO_4$, and purified by flash chromatography on silica with acetone: toluene 30:70; yield: 3.49 g, (92%).

$^1$H NMR ($CDCl_3$) δ8.15 (1H,d), 7.37 (1H,d), 4.89 (2H,d), 3.45 (1H,t,OH), 2.87 (3H,s).

Step 7: 5-(((methanesulfonyl)oxy)methyl )-2-methylthiazolo[5,4-b]pyridine

To a solution of the alcohol of Step 6 (303 mg, 1.68 mmol) in 17 mL of $CH_2Cl_2$ at −40° C., triethylamine (350 μl, 2.5 mmol) and methane-sulfonyl chloride (170 μl, 2.2 mmol) were added and the solution was stirred at −40° C. for 30 min and at 0° C. for 2 hr. Saturated aq. $NaHCO_3$ was added and the product was extracted in $CH_2C_{12}$, dried over $Na_2SO_4$, concentrated, and the remaining water was stripped with toluene twice.

$^1$H NMR ($CDCl_3$) δ8.23 (1H,d), 7.48 (1H,d), 5.43 (2H,s), 3.10 (3H,s), 2.88 (3H,s).

Step 8: ((2-methylthiazolo[5,4-b]pyridine-5-yl)methyl)triphenylphosphonium methanesulfonate A solution of the mesylate of Step 7 (1.68 mmol) and triphenylphosphine (660 mg, 2.52 mmol) in 8 mL of anhyd. $CH_3CN$ was heated at reflux for 2 hr. The solvent was evaporated and the oil was swished in ether and the ether decanted twice. It was swished again in 25 mL ether over the weekend. The solvent was decanted to afford a very hygroscopic solid, which was dried under vacuum; yield: 732 mg, (84%).

$^1$H NMR (DMSO) δ8.20 (1H,d), 7.65–7.90 (15H,m), 7.41 (1H,d), 5.58 (2H,d), 2.77 (3H,s), 2.29 (3H,s).

Step 9: Sodium (R) 1-(((3-(2-(1-hydroxy-1-methylethyl)phenyl)-1 -(3-(2-(2-methylthiazolo[5,4-b ]pyridine-5-yl)ethenyl)phenyl)propyl)thio)methyly)cyclopropaneacetate Following the procedure described in Steps 18–19 of Example 1, the title compound was prepared from the phosphonium salt of Step 8.

Anal. calcd. for $C_{33}H_{35}N_2O_3S_2Na.3.6H_2O$: C, 60.09; H, 6.45; N, 4.25 Found: C, 60.04; H, 6.41; N, 4.28.

EXAMPLE 178

Sodium 1-(((1(R)-(3-(2-(2,3-dichlorothieno[3,2-b]pyridin-5-yl)oxymethyl)phenyl)-3-(2-(1-hydroxy-1-methylethyl)phenyl)propyl)thio)methyl)cyclopropaneacetate Step 1: Tetrahydrothiophen-3-one oxime To commercially available (from Aldrich) tetrahydrothiophen-3-one (12 g, 117 mmol) and hydroxylamine hydrochloride (12 g, 173 mmol) in 300 mL of EtOH was added BaCO$_3$ (24 g, 121 mmol) and the reaction mixture was refluxed overnight. After being filtered through celite the solvent was removed and the residue dissolved in 1.5 L of H$_2$O and extracted with EtOAc (2×300 mL). The organic phases are combined, dried over Na$_2$SO$_4$ and the solvent removed under reduced pressure. Purification by flash chromatography (40%→50% hexane in EtOAc) yielded 12.0 g (87%) of the title compound.

Step 2: 3-Aminothiophene

The hydroxylamine (12 g, 102 mmol) of Step 1 in 400 mL of a 6.5N MeOH in HCl was stirred at room temperature for 2 days at the end of which water (2 L) was added. The solution was neutralized with solid NaHCO$_3$ and extracted with ether (2×200 mL). The organic phases were combined, dried with Na$_2$SO$_4$ and the solvent removed to give 10.0 g (97%) of the aminothiophene.

$^1$H NMR (400 MHz, CD$_3$COCD$_3$) δ7.45 (1H, dd), 7.7 (1H, dd), 8.15 (1H, dd), 8.7 (2H, bs).

Step 3: 3-Acetamidothiophene

To the 3-aminothiophene of Step 2 (1.0 g, 10.1 mmol) in 10 mL of water was added NaOH (3M, 3.37 mL, 10.1 mmol) followed by Ac$_2$O (0.95 mL, 10.1 mmol) and the reaction mixture was heated to 60° C. for 4 h. The reaction mixture was quenched at 25° C. with 1N HCl (10 mL) and extracted with EtOAc (2×20 mL). The organic phases were combined, dried with Na$_2$SO$_4$ and the solvent removed to yield 1.0 g (70%) of the title acetamide.

$^1$H NMR (400 MHz, CD$_3$COCD$_3$) δ2.2 (3H, s), 8.0 (2H, AB), 9.85 (1H, s), 10.35 (1H bs).

Step 4: 5-chlorothieno[3,2-b]pydidine

Phosphorus oxychloride (54.5 mL, 584 mmol) was added to neat DMF (15.1 mL) at 0° C. followed by 120 mL of dichloroethane. The acetamide from Step 3 (27.5 g, 195 mmol) in 360 mL of dichloroethane was added and the reaction mixture stirred 15 min at 0° C. and refluxed 4 h. It was cooled to 25° C., poured onto ice and the organic phase separated, dried over Na$_2$SO$_4$ and the solvent removed. Purification by flash chromatography (20% EtOAc in hexane) yielded 17.85 g (54%) of the title compound.

$^1$H NMR (400 MHz, CD$_3$COCD$_3$) δ7.4 (1H, d), 7.5 (1H, d), 8.1 (1H, d), 8.5 (1H, d).

Step 5: 2,3,5-trichlorothieno[3,2-b]pyridine

A mixture of chlorothienopyridine (17.85 g, 105,2 mmol) of Step 4 and trichloroisocyanuric acid (48.8 g, 210 mmol) in 420 mL of CH$_3$CN was refluxed 2 h. The mixture was cooled and the solvent removed to give a residue that was purified by flash chromatography (toluene) to yield 14.74 g (59%) of the title compound.

$^1$H NMR (400 MHz, CDCL$_3$) δ7.4 (1H, d), 8.0 (1H, d).

Step 6: Methyl 1-(((1(R)-(3-hydroxymethyl)phenyl)-3-(2-(1-hydroxy-1-methyl-1-methylethyl)phenyl)propyl)thio)methyl)cyclopropaneacetate The aldehyde from Step 17 Example 1(0.77 g, 1.74 mmol) was dissolved in 2 mL of MeOH at 0° C. and solid NaBH$_4$ (33 mg, 0.87 mmol) was added portionwise. After 30 min of contact the solution was quenched with a 25% solution of NH$_4$OAc and the alcohol extracted with EtOAc (3×10mL). The organic phases were combined, dried over Na$_2$SO$_4$ and the solvent removed to give 0.70 g (91%) of the title compound identical with the product obtained in Step 16 of Example 1.

Step 7: 1-(((1(R)-(3-hydroxymethyl)phenyl)-3-(2-(1-hydroxy-1 -methyl-1-methylethyl)phenyl)propyl)thio)methyl)cyclopropane acetic acid To the alcohol (0.55 g, 1.2 mmol) of Step 6 in 3mL of THF and 1mL of MeOH was added 1N NaOH (0.5 mL) and the reaction left stirring 4 h. The solution was quenched with a 25% solution of NH$_4$OAc, extracted with EtOAc (3×10 mL) and the combined organic phases dried over Na$_2$SO$_4$. The solvent was removed to give 0.43 g (85%) of the title compound.

$^1$H NMR (400 MHz, CD$_3$COCD$_3$) δ0.35–0.55 (4H, m), 1.5 (3H, s), 2.1–2.3 (2H, m), 2.4 (2H, AB), 2.5 (2H, s), 2.85 (2H, dt), 3.1 (2H, dt), 4.0 (1H, t), 4.65 (2H, s), 7.05–7.15 (3H, m), 7.2–7.3 (3H, m), 7.45(2H, m).

Step 8: Sodium 1-(((1(R)-(3-(2-(2,3-dichlorothieno[3,2-b]-pyridin-5-yl)oxymethyl)-phenyl)-3-(2-(1-hydroxy-1-methylethyl)phenyl)propyl)thio)methyl)cyclopropaneacetate To the alcohol (0.282 g, 1.18 mmol) of Step 7 in DMF (4 mL) at 5° C. was added NaH (0.113 g, 3.7 mmol) and after stirring 30 min the thienopyridine (0.298 g, 1.25 mmol) of Step 5 was added and the temperature was raised to 25° C. and left 30 min. The solution was quenched with a 25% solution of NH$_4$OAc and extracted with EtOAc (3× 15 mL). The organic fractions were combined, dried over Na$_2$SO$_4$ and the solvent removed. Purification by flash chromatogrphy (40% EtOAc in Hexane, 2% HOAc) yielded 0.254 g (34%) of the title acid.

$^1$H NMR (400 MHz, CD$_3$COCD$_3$) δ0.3–0.5 (4H, m), 1.47 (3H, s), 1.53 (3H, s), 2.1–2.3 (2H, m), 2.4 (2H, s), 2.5 (2H, AB), 2.75 (2H, m), 3.12, (1H, dt), 4.05 (1H, t), 5.5 (2H, s), 7.10–7.25 (3H, m), 7.32 (1H, d), 7.4–7.5 (4H, m), 7.52 (1H, s), 8.25 (1H, d).

To this acid in 3 mL of EtOH was added NaOH (1N, 1.0 equivalent). The solvent was evaporated and the product was lyophilized to give the title compound.

Anal. Cal'd.for C$_{32}$H$_{32}$Cl$_2$NNaO$_4$S$_2$.H$_2$O: C, 57.31; H, 5.11; N, 2.09 Found: C, 57.62; H, 5.22; N, 2.13.

EXAMPLE 185

Sodium 1-(((1(R)-(3-(2-(2,3-dichlorothieno[3,2-b]pyridin-5-yl)methoxy)phenyl)-3-(2-(1-hydroxy-1-methylethyl) phenyl)propyl)thio)methyl))cyclopropaneacetate Step 1: Methyl 2-[3-(3-hydroxyphenyl)-3-oxopropyl]benzoate To a suspension of 3-(7-chloroquinolin-2-yl)methoxy-)benzaldehyde (10.08 g, 33.9 mmol; U.S. Pat. No. 4,851,409 example 16 step 1) in toluene at 0° C. was added dropwise 1M vinylmagnesium bromide in THF (37 mL). After 30 min. the solution was quenched with NH$_4$OAc, extracted with H$_2$O, brine and dried over Na$_2$SO$_4$. The solvent was removed to afford 11.07 g of the allylic alcohol. This alcohol (11.00 g, 32.4 mmol), methyl o-bromobenzoate (7.31 g, 34 mmol), Pd(OAc)$_2$ (218 mg), LiCl (1.37 g) and LiOAc.H$_2$O (9.04 g) in 65 mL of DMF were heated to 100° C. for 3 h. The solution was cooled, poured in H$_2$O (300 mL) and extracted with EtOAc (3×200 mL). The organic fractions were combined, washed with H$_2$O, brine and dried over Na$_2$SO$_4$. Purification by chromatography (5% EtOAc in toluene) yield 12.44 g of LVIII. $^1$H NMR (300 MHz, CD$_3$COCD$_3$) δ3.30 (4H, m), 3.75 (3H, s), 5.45 (2H, s), 7.30–8.00 (12H, m) and 8.40 (1H, d).

To LVIII (1 g, 217 mmol) in DMF (10 mL) at 100° C. was added dropwise a solution of CuCl$_2$ (0.554 g, 4.12 mmol) in 2 mL H$_2$O. The reaction mixture was heated at 100° C. for 2 h, diluted with H$_2$O (100 mL) at 25° C. and extracted with CH$_2$Cl$_2$ (3×50 mL). The organic fractions were combined, dried over Na$_2$SO$_4$ and the solvent removed. Purification by flash chromatography (25% EtOAc in hexane) yielded 0.56 g (93%) of LIX. $^1$H NMR (300 MHz, CDCl$_3$) δ3.30 (4H, m), 3.90 (3H, s), 6.60 (1H, s), 7.05 (1H, dd), 7.20–7.35 (3H, m), 7.42 (1H, t), 7.5 (1H, d), 7.25 (1H, s), 7.9 (1H, d).

Step 2: Methyl ((3-(2-(2,3-dichlorothieno[3,2-b]pyridin-5-yl)methoxy)phenyl)-3-oxopropyl) benzoate To compound LIX (0.161 g, 0.56 mmole) and LVII (0.141 g, 0.56 mmole) in DMF (2.0 mL) was added Cs$_2$CO$_3$(0.19 g, 0.58 mmole). The reaction mixture was heated and stirred at 50° C. overnight. The solution was quenched with NH$_4$Cl (10 mL) and extracted with EtOAc (3×10 mL). The organic fractions were combined, dried over Na$_2$SO$_4$ and the solvent removed. Purification by flash chromatography (20% EtOAc in hexane) yielded 0.11 g (39%) of LX. $^1$H NMR (300 MHz, CDCl$_3$) δ: 3.35 (4H, m) 3.9 (3H, s), 5.42 (2H, s), 7.20 (1H, dd), 7.26 (1H, dd), 7.30–7.40 (2H, m), 7.46 (1H, t), 7.65 (2H, 2d), 7.70 (1H, s), 7.95 (1H, d), 8.08 (1H, d).

Step 3: Methyl ((3-(2-(2,3-dichlorothieno[3,2-b]pyridin-5-yl)methoxy)phenyl)-3-(S)-hydroxypropyl) benzoate To LX (1.75, 3.5 mmole) in THF (7 mL) at −20° C. was added the catalyst of Example 1 step 13 (0.189 g, 0.7 mmole) and BH$_3$ (1M in THF, 8.75 mL, 2.5 eq). The mixture was stirred 2 h at −20° C. The solution was quenched with NH$_4$OAc (20 mL) and extracted with EtOAc (3×20 mL). The organic fractions were combined, dried over Na$_2$SO$_4$ and the solvent removed. Purification by flash chromatography (20% EtOAc in hexane) yielded 1.40 g (80%) of LXI. $^1$H NMR (300 MHz, CDCl$_3$) δ: 2.05 (2H, m), 2.95 (1H, d), 3.05 (2H, m), 3.9 (3H, s), 4.68 (1H, m), 5.4 (2H, 1s), 6.90 (1H, dd), 6.95 (1H, d), 7.05 (1H, s), 7.25 (3H, m), 7.42 (1H, t), 7.62 (1H, d), 7.90 (1H, d), 8.05 (1H, d)

Step 4: Sodium 1-(((1(R)-(3-(2-(2,3-dichlorothieno[3,2-b]pyridin-5-yl)methoxy)phenyl)-3-(2-(1-hydroxy-1 -methylethyl)phenyl)propyl)thio)methyl)cyclopropaneacetate To LXI (1.4 g, 2.78 mmole) in CH$_2$Cl$_2$ (20 mL) at −35° C. was added Et$_3$N (0.58 mL, 4.18 mmoles 1.5 eg) followed by MsCl (0.28 mL, 3.62 mmoles). Then the temperature was raised to 0° C. for 35 min. The reaction was quenched with NaHCO$_3$ solution (20 mL) and extracted with EtOAc (3×30 mL). The organic fractions were combined, dried over Na$_2$SO$_4$ and the solvent removed to give 1.5 g (95%) of crude mesylate. $^1$H NMR (300 MHz, CDCl$_3$) δ: 2.10–2.40 (2H, m), 2.90–3.15 (2H, m), 3.85 (3H, s), 5.40 (2H, s), 5.55 (1H, dd), 7.05 (3H, m), 7.1 (1H, s), 7.20–7.35 (3H, m), 7.45 (1H, t), 7.62 (1H, d) 7.90 (1H, d), 8.08 (1H, d).

To a degassed solution of the thiolacid from Example 4 step 12 (0.426 g, 2.9 mmole) in THF (10 mL) at −20° C. was added dropwise BuLi (2.45 mL of 2.5M). After stirring 15 minutes the temperature was raised to 0° C. for 15 minutes and cooled back to −25° C. The crude mesylate was added to the suspension and left 30 minutes. The temperature was allowed to rise to −5° C. over 2 h. The reaction was quenched with NH$_4$OAc (20 mL) and extracted with EtOAc (3×30 mL). The organic fractions were combined, dried over Na$_2$SO$_4$ and the solvent removed. Purification by flash chromatography (20% EtOAc in hexane, +1% HOAc) yielded 1.22 g (70%) of the acid. $^1$H NMR (300 MHz, CDCl$_3$) δ: 0.45 (4H, m), 2.10 (2H, m), 2.25–2.55 (4H, m), 2.80–3.10 (2H, m), 3.85 (4H, m), 5.40 (2H, m), 6.88 (1H, dd), 6.95 (1H, d), 7.05 (1H, s), 7.12–7.30 (3H, m), 7.38 (1H, t), 7.65 (1H, d), 7.85 (1H, d), 8.1 (1H, d).

To the above acid (0.69 g or 1.09 mmole) in THF (14 mL) at 5° C. was added dropwise MeMgCl (previously treated with CeCl$_3$) in THF (5.84 mL, 8.72 mmoles) and the mixture was stirred 1 h. The reaction was quenched with NH$_4$Cl and ice and extracted with EtOAc (3× 25 mL). The organic fractions were combined, washed with brine and dried over Na$_2$SO$_4$. Purification by flash chromatography (20% EtOAc in hexane, +1% HOAc) yielded 0.50 g (72%) of LXII. $^1$H NMR (300 MHz, CD$_3$COCD$_3$) δ: 0.45 (4H, m), 1.52 (6H, s), 2.15 (2H, m), 2.32 (2H, s), 2.42 (2H, s), 2.8 (1H, m), 3.09 (1H, m), 3.97 (1H, t), 5.38 (2H, s), 6.95 (1H, dd), 7.00–7.30 (6H, m), 7.40 (1H, dd), 7.72 (1H, d), 8.45 (1H, d).

To this acid in 1.5 mL of EtOH was added NaOH (1N, 1.0 equivalent). The solvent was evaporated and the product was lyophilized to give the title compound.

Anal. Cal'd.for C$_{32}$H$_{33}$Cl$_2$NNaO$_4$S$_2$.1.5H$_2$O: C, 58.44; H, 5.51; N, 2.12. Found: C, 58.15; H, 5.1–9; N, 2.30.

EXAMPLE 192

Sodium 3-(((3-(2-(2,3-dichlorothieno[3,2-b]pyridin-5 -yl)ethenyl)phenyl)-1-((3-(dimethylamino)- 3-oxopropyl)thio)methyl)thio)propanoate 3-(((3-(2-(2,3-Dichlorothieno[3,2-b]pyridin-5-yl)ethenyl)phenyl)-1-(( 3-(dimethylamino)-3-oxopropyl)thio)methyl)thio)propanoic acid The title compound was prepared according to the general procedure described in Method S. $^1$H NMR (400 MHz, CD3COCD$_3$) δ 2.65 (4H, t), 2.75–2.97 (8H, m), 3.0 (3H, s), 5.35 (1H, s), 7.40–7.55 (3H, m), 7.65 (1H, d), 7.75 (1H, d), 7.85 (1H, s), 7.9 (1H, d), 8.45 (1H, d).

EXAMPLE 218

Sodium 1-(((1(R)-(3-(2-(2,3-dichlorothieno[3,2-b]pyridin-5 -yl)cyclopropyl)phenyl)-3-(2-(1-hydroxymethyl-1 -methylethyl)phenyl)propyl)thio) methylcyclopropaneacetate Step 1: Methyl 1-(((1(R)-(3-(2-(2,3-dichlorothieno[3,2-b] pyridin-5-yl)cyclopropyl)phenyl)-3-(2-(1-hydroxymethyl-1 -methylethyl)phenyl)-propyl)thio)methylcyclopropaneacetate To trimethylsulfoxonium iodide (0.137 g, 0.62 mol) in 1.3 mL of DMSO was added NaH (5 mg, 0.21 mmol) at 25° C. followed by the ester (0.1 g, 0.15 mmol) of Step 4 from Example 4A and stirred overnight. The reaction mixture was quenched with 10 mL of H$_2$O, extracted with EtOAc (2×10 mL) and the organic phases combined and dried over Na$_2$SO$_4$. Purification by flash chromatography (15% EtOAc in hexane) yield 80mg (80%) of the title compound.

$^1$H NMR (300 MHz, CD$_3$COCD$_3$) δ0.4–0.5 (4H, m), 1.55 (6H, s), 1.6 (1H, m), 1.85 (1H, m), 2.15 (2H, m), 2.4 (2H, AB), 2.5 (2H, s), 2.65 (2H, m), 2.85 (1H, m), 3.1 (1H, m), 3.55 (3H, s), 3.9 (1H, d), 4.0 (1H, t), 7.1 (4H, m), 7.25 (3H, m), 7.4 (1H, d), 7.5 (1H, d), 8.25 (1H, d).

Step 2: Sodium 1-(((1(R)-(3-(2-(2,3-dichlorothieno[3,2-b] pyridin-5-yl)-cyclopropyl)phenyl)-3-(2-(1-hydroxymethyl-1 -methylethyl)phenyl)propyl)thio)methyl) cyclopropaneacetate To the ester (80mg, 0.12 mmol) of Step 1 in 0.5 mL of THF and 0.5mL of MeOH was added 2 equivalent of 1N NaOH and left 4 h at 25° C. The reaction mixture was quenched with NH$_4$OAc, extracted with EtOAc (2×5 mL) and the organic phases combined and dried over Na$_2$SO$_4$. Purification by flash chromatography (30% EtOAc in Hexane, 2% HOAc ) yielded 50 mg (63%) of the title compound. The proton NMR is complex; some characteristic signals are; $^1$H NMR (400 MHz, CD$_3$COCD$_3$) δ1.47 (3H, s), 1.55 (3H, s), 1.85 (1H, m), 2.25 (3H, m), 3.97 (1H, t), 7.0 (4H, m), 7.25 (3H, m), 7.3 (1H,d), 7.37 (1H, d), 8.15 (1H, d).

Anal. Cal'd.for $C_{34}H_{34}Cl_2NNaO_3S_2 \cdot 1/2H_2O$: C, 60.79; H, 5.25; N, 2.08; S, 9.41; Cl, 10.42 Found: C, 60.59; H, 5.10; N, 2.30; S, 9.61; Cl, 10.48.

EXAMPLE 219

Sodium 1-(((1(R)-(3-(2-(2,3-dichlorothieno[3,2-b]pyridin-5-yl)ethenyl)phenyl)-3-(4-fluorophenylthio)propyl)thio)methyl) cyclopropaneacetate The title compound was prepared according to the general procedure described in Method O.

Anal. Cal'd.for $C_{30}H_{25}Cl_2FNNaO_2S_3 \cdot H_2O$: C, 54.71; H, 4.13; N, 2.13. Found: C, 54.98; H, 3.98; N, 2.07.

The following compounds were prepared according to the general procedures described in Examples 1–6. Elemental analysis data for each are provided in Table 3.

TABLE 3

| | | ELEMENTAL ANALYSIS | | | | | |
|---|---|---|---|---|---|---|---|
| | | CALCULATED | | | FOUND | | |
| EXAMPLE | FORMULA | C | H | N | C | H | N |
| 58 | $C_{34}H_{32}Cl_2NNaO_3S_2 \cdot H_2O$ | 60.17 | 5.05 | 2.06 | 59.65 | 4.73 | 1.87 |
| 127 | $C_{30}H_{25}Cl_2BrN_2O_2S_2Na$ | 53.25 | 3.84 | 2.07 | 53.11 | 4.04 | 2.03 |
| 128 | $C_{33}H_{30}Cl_2S_2NO_3Na \cdot 5H_2O$ | 60.45 | 4.76 | 2.13 | 60.61 | 4.86 | 2.09 |
| 129 | $C_{30}H_{27}Cl_2BrNO_2S_2Na \cdot 0.5H_2O$ | 53.09 | 4.13 | 2.06 | 52.95 | 4.50 | 1.91 |
| 132 | $C_{34}H_{34}Cl_2NO_3S_2Na \cdot H_2O$ | 60.08 | 5.30 | 2.06 | 59.70 | 5.21 | 2.17 |
| 133 | $C_{30}H_{25}Cl_2FNNaO_2S_2 \cdot H_2O$ | 57.51 | 4.34 | 2.24 | 57.90 | 4.16 | 2.11 |
| 134 | $C_{33}H_{32}Cl_2NO_3S_2Na \cdot H_2O$ | 59.54 | 5.11 | 2.10 | 59.30 | 5.14 | 2.25 |
| 135 | $C_{30}H_{25}Cl_3NO_2S_2Na \cdot 0.5H_2O$ | 56.96 | 4.11 | 2.21 | 56.77 | 3.96 | 2.24 |
| 136 | $C_{28}H_{24}Cl_2NO_2S_3Na \cdot 0.6H_2O$ | 55.37 | 4.18 | 2.31 | 55.36 | 4.27 | 2.32 |
| 137 | $C_{31}H_{25}Cl_2F_3NO_2S_2Na \cdot H_2O$ | 55.03 | 4.02 | 2.07 | 55.02 | 4.18 | 2.14 |
| 138 | $C_{34}H_{32}Cl_2NNaO_3S_2 \cdot H_2O$ | 60.17 | 5.06 | 2.06 | 59.78 | 4.80 | 2.05 |
| 139 | $C_{33}H_{30}Cl_2NO_4S_3Na \cdot 3.4H_2O$ | 52.43 | 4.91 | 1.85 | 52.44 | 4.71 | 1.69 |
| 140 | $C_{34}H_{32}Cl_2NO_3S_2Na \cdot 1.5H_2O$ | 59.46 | 5.10 | 2.04 | 59.46 | 5.30 | 1.94 |
| 143 | $C_{33}H_{31}Cl_2FNO_3S_2Na \cdot 1H_2O$ | 57.89 | 4.86 | 2.05 | 57.84 | 4.77 | 2.02 |
| 144 | $C_{33}H_{21}Cl_3NNaO_3S_2 \cdot H_2O$ | 56.53 | 4.74 | 2.09 | 56.17 | 4.51 | 1.95 |
| 145 | $C_{34}H_{31}Cl_3NNaO_3S_2 \cdot 1.5H_2O$ | 56.55 | 4.76 | 1.94 | 56.46 | 4.30 | 1.95 |
| 146 | $C_{31}H_{28}Cl_2NNaO_3S_2 \cdot 1.5H_2O$ | 57.49 | 4.83 | 2.16 | 57.41 | 4.41 | 2.09 |
| 147 | $C_{32}H_{28}Cl_2NNaS_2O_4 \cdot 1.5H_2O$ | 56.89 | 4.62 | 2.07 | 56.74 | 4.37 | 2.07 |
| 148 | $C_{36}H_{36}NCl_2O_3S_2Na \cdot 0.5H_2O$ | 61.97 | 5.35 | 2.01 | 61.85 | 5.47 | 2.09 |
| 149 | $C_{31}H_{27}Cl_3NNaO_3S_2 \cdot H_2O$ | 55.32 | 4.34 | 2.08 | 55.47 | 4.12 | 1.95 |
| 150 | $C_{30}H_{26}Cl_2NO_2S_2Na \cdot H_2O$ | 59.21 | 4.64 | 2.30 | 59.15 | 4.63 | 2.43 |
| 152 | $C_{31}H_{27}Cl_2BrNNaO_3S_2 \cdot H_2O$ | 51.89 | 4.07 | 1.95 | 52.28 | 3.90 | 1.84 |
| 153 | $C_{32}H_{28}S_2O_3Cl_2NNa \cdot H_2O$ | 60.00 | 4.68 | 2.18 | 59.91 | 4.55 | 2.34 |
| 154 | $C_{26}H_{22}N_3O_2S_3Cl_2Na \cdot H_2O$ | 50.65 | 3.92 | 6.8 | 50.55 | 3.94 | 6.76 |
| 155 | $C_{32}H_{31}NS_2O_3Cl_2Na \cdot H_2O$ | 58.80 | 5.08 | 2.14 | 58.65 | 4.92 | 1.94 |
| 157 | $C_{33}H_{31}Cl_2BrNNaO_3S_2 \cdot 0.5H_2O$ | 53.95 | 4.41 | 1.81 | 53.81 | 4.39 | 1.90 |
| 164 | $C_{38}H_{38}NS_2Cl_2O_4Na \cdot 3H_2O$ | 59.83 | 5.94 | 1.83 | 59.96 | 5.64 | 1.78 |
| 168 | $C_{33}H_{30}Cl_2NNaO_4S \cdot 1.5H_2O$ | 57.47 | 4.82 | 2.03 | 57.47 | 4.76 | 1.95 |
| 169 | $C_{35}H_{33}Cl_3NNaO_4S_2 \cdot 1.5H_2O$ | 55.89 | 4.82 | 1.86 | 55.74 | 4.69 | 1.71 |
| 170 | $C_{34}H_{36}NO_5Cl_2S_2P \cdot 0.5H_2O$ | 57.22 | 5.23 | 1.96 | 57.53 | 5.56 | 1.76 |
| 171 | $C_{33}H_{30}Cl_2NO_2S_3Na \cdot 0.8H_2O$ | 58.54 | 4.70 | 2.07 | 58.56 | 4.70 | 1.90 |

What is claimed is:

1. A compound of the formula:

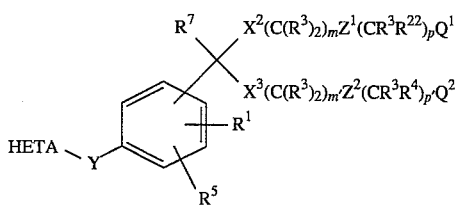

wherein:

$R^1$ is H or $R^2$;

$R^2$ is lower alkyl, lower alkenyl, lower alkynyl, $-CF_3$, $-CH_2F$, $-CHF_2$, $Ph(R^{26})_2$, $CH_2Ph(R^{26})_2$, or $CH_2CH_2Ph(R^{26})_2$ or two $R^2$ groups joined to the same atom may form a monocyclic or bicyclic ring of up to 8 members comprising carbon atoms and up to 2 heteroatoms chosen from O, S, and N;

$R^3$ is H or $R^2$;

$R^4$ is $R^3$, halogen, $-NO_2$, $-CN$, $-OR^3$, $-SR^3$, $N(R^3)_2$, $NR^3COR^7$, $S(O)R^2$, or $S(O)_2R^2$;

$CR^3R^{22}$ may be the radical of a standard amino acid;

$R^5$ is H, halogen, $-NO_2$, $-N_3$, $-CN$, $-SR^2$, $-S(O)R^2$, $S(O)_2R^2$, $-N(R^3)_2$, $-OR^3$, $-COR^3$, or lower alkyl;

$R^6$ is $-(CH_2)_s-C(R^7)_2-(CH_2)_s-R^8$ or $-CH_2CON(R^{20})_2$;

$R^7$ is H or lower alkyl;

$R^8$ is A) a monocyclic or bicyclic heterocyclic radical containing from 3 to 12 nuclear carbon atoms and 1 or 2 nuclear heteroatoms selected from N, S, and O and with each ring in the heterocyclic radical being formed of 5 or 6 atoms, or B) the radical $W-R^9$;

$R^9$ contains up to 21 carbon atoms and is (1) a hydrocarbon radical or (2) an acyl radical of an organic acyclic or monocyclic carboxylic acid containing not more than 1 heteratom in the ring;

$R^{10}$ is H, lower alkyl, or benzyl;

$R^{11}$ is lower alkyl, $-COR^{14}$, $Ph(R^{26})_2$, $CH_2Ph(R^{26})_2$, or $CH_2CH_2Ph(R^{26})_2$;

$R^{12}$ is H, $R^{11}$, or two $R^{12}$ groups joined to the same N may form a saturated ring of 5 or 6 members comprising carbon atoms and up to two heteroatoms chosen from O, S, and N;

$R^{13}$ is lower alkyl, lower alkenyl, lower alkynyl, —CF$_3$, Ph(R$^{26}$)$_2$, CH$_2$Ph(R$^{26}$)$_2$, or CH$_2$CH$_2$Ph(R$^{26}$)$_2$;

$R^{14}$ is H or $R^{13}$;

$R^{15}$ is H, oxetanyl or $R^{11}$;

$R^{16}$ is H, lower alkyl, or OH;

$R^{17}$ is lower alkyl, lower alkenyl, lower alkynyl, Ph(R$^{26}$)$_2$, CH$_2$Ph(R$^{26}$)$_2$, or CH$_2$CH$_2$Ph(R$^{26}$)$_2$;

$R^{18}$ is $R^{13}$;

$R^{19}$ is H, lower alkyl, lower alkenyl, lower alkynyl, —CF$_3$, Ph, CH$_2$Ph, or CH$_2$CH$_2$Ph;

$R^{20}$ is H, lower alkyl, Ph(R$^{26}$)$_2$, CH$_2$Ph(R$^{26}$)$_2$, or CH$_2$CH$_2$Ph(R$^{26}$)$_2$ or two $R^{20}$ groups joined to the same N may form a saturated ring of 5 or 6 members comprising carbon atoms and up to two heteroatoms chosen from O, S, and N;

$R^{21}$ is H or $R^{17}$;

$R^{22}$ is $R^4$, CHR$^7$OR$^3$, or CHR$^7$SR$^2$;

$R^{23}$, $R^{24}$, and $R^{25}$ is each independently H, lower alkyl, —CN, —CF$_3$, C(R$^3$)$_2$OH, COR$^3$, CO$_2$R$^7$, CON(R$^{20}$)$_2$, OR$^3$, SR$^2$, S(O)R$^2$, S(O)$_2$R$^2$, N(R$^{12}$)$_2$, halogen, or an electron pair;

$R^{26}$ is H, lower alkyl, —SR$^{27}$, —OR$^{28}$, —N(R$^{28}$)$_2$, —CO$_2$R$^7$, CON(R$^{28}$)$_2$, —COR$^7$, —CN, CF$_3$, NO$_2$, SCF$_3$, or halogen;

$R^{27}$ is lower alkyl, phenyl, or benzyl;

$R^{28}$ is $R^{27}$, H, or COR$^7$, or two $R^{28}$ groups joined to the same N may form a saturated ring of 5 or 6 members comprising carbon atoms and up to 2 heteroatoms chosen from O, S, or N;

m and m' are independently 0–8;

p and p' are independently 0–8;

m+p is 1–10 when $X^2$ is O, S, S(O), or S(O)$_2$ and $Z^1$ is a bond;

m+p is 0–10 when $Z^1$ is HET(R$^{23}$R$^{24}$R$^{25}$);

m+p is 0–10 when $X^2$ is CR$^3$R$^{16}$;

m'+p' is 1–10 when $X^3$ is O, S, S(O), or S(O)$_2$ and $Z^2$ is a bond;

m' +p' is 0–10 when $Z^2$ is HET(R$^{23}$R$^{24}$R$^{25}$);

m' +p' is 0–10 when $X^3$ is CR$^3$R$^{16}$;

s is 0–3;

$Q^1$ is tetrazol-5-yl, —CO$_2$R$^3$, —CO$_2$R$^6$, —CONHS(O)$_2$R$^{13}$, —CN, —CON(R$^{20}$)$_2$, NR$^{21}$S(O)$_2$R$^{13}$, —NR$^{21}$CON(R$^{20}$)$_2$, —NR$^{21}$COR$^{14}$, OCON(R$^{20}$)$_2$, —COR$^{19}$, —S(O)R$^{18}$, —S(O)$_2$R$^{18}$, —S(O)$_2$N(R$^{20}$)$_2$, —NO$_2$, NR$^{21}$CO$_2$R$^{17}$, —C(N(R$^{12}$)$_2$)=NR$^{21}$, —C(R$^{19}$)=NOH, P(O)(OR$^{10}$)$_2$ or C(R$^3$)$_2$OR$^3$; or if $Q^1$ is CO$_2$H and $R^{22}$ is —OH, —SH, CHR$^7$OH or —NHR$^3$, then $Q^1$ and $R^{22}$ and the carbons through which they are attached may form a heterocyclic ring by loss of water;

$Q^2$ is H, OR$^{15}$, lower alkyl, halogen, or $Q^1$;

W is O, S, or NR$^3$;

$X^1$ is O, S, —S(O)—, —S(O)$_2$—, =NR$^3$, —C(R$^3$)$_2$—, or a bond;

$X^2$ and $X^3$ are independently O, S, S(O), S(O)$_2$, CR$^3$R$^{16}$, or a bond;

Y is —CR$^3$=CR$^3$—, —C(R$^3$)$_2$—X$^1$—, —X$^1$—C(R$^3$)$_2$—, —C(R$^3$)$_2$—X$^1$—C(R$^3$)$_2$—, —CH(CH$_2$)CH—, —C≡C—, —CO—, —NR$^3$CO—, —CONR$^3$—, O, S, or NR$^3$;

$Z^1$ and $Z^2$ are independently HET(R$^{23}$R$^{24}$R$^{25}$) or a bond;

HET is the diradical of benzene, pyridine, furan, thiophene, thiazole, or 1,2,5-thiadiazole;

HETA is HE$^1$ or HE$^2$

HE$^1$ is

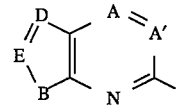

HE$^2$ is

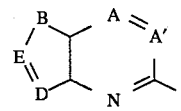

A and A$^1$ is each independently N or CR$^5$;

B is O, S, or S(O);

D is N or CR$^4$;

E is CR$^4$ when D is CR$^4$;

E is CR$^3$ when D is N;

or a pharmaceutically acceptable salt thereof.

2. A compound of claim 1 of the formula:

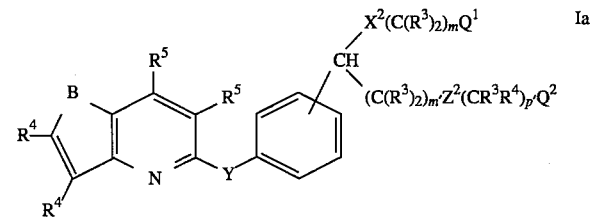

wherein:

B is S or O;

$R^4$ is H, lower alkyl, halogen, CN, CF$_3$, or S(O)$_2$R$^2$;

$R^5$ is H or halogen;

m and m' is each independently 1–6;

p' is 0 or 1;

$Q^1$ is CO$_2$R$^3$, CO$_2$R$^6$, —CONHS(O)$_2$R$^{13}$, Tetrazol-5-yl or C(R$^3$)$_2$OH;

$Q^2$ is H, C(R$^3$)$_2$OH, halogen, OR$^{15}$, CON(R$^{20}$)$_2$, P(O)(OR$^{10}$)$_2$, SO$_2$R$^{18}$, CO$_2$R$^3$ or lower alkyl;

$X^2$ is S or O;

Y is —CH=CH—, —CH$_2$—O—, —O—CH$_2$—, —CH$_2$—CH$_2$—, —C≡C—, —C(CH$_2$)$_2$— or —CH(CH$_2$)CH—;

$Z^2$ is HET (R$^{23}$R$^{24}$) or a bond; and

HET is a diradical of benzene, 1,2,5-thiadiazole, thiazole or thiophene; and the remaining substituents are as defined in claim 1.

3. A compound of claim 1 of the formula:

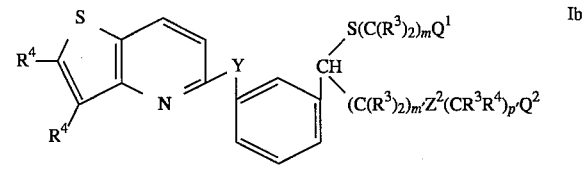

wherein:

R³ is H, lower alkyl, or two R³ joined to the same carbon may form a monocyclic ring from 3 to 6 members, optionally containing one oxygen or one sulfur;

R⁴ is H, lower alkyl, halogen, —CN, CF₃, or —S(O)₂R²;

R²³ and R²⁴ are independently H, halogen, lower alkyl, SR², CF₃, COR³ or C(R³)₂OR³;

m and m' are independently 1–5;

p' is 0 or 1;

$Q^1$ is —CO₂R³, tetrazol-5-yl, or —CONHS(O)₂R¹³; and $Q^2$ is H, C(R³)₂OH, P(O)(OR¹⁰)₂, SO₂R¹⁸, CO₂R³ or OR¹⁵;

Y is —CH=CH—, —CH₂O—, or —OCH₂—;

$Z^2$ is HET (R²³R²⁴); and

HET is a diradical of benzene, 1,2,5-thiadiazole, thiazole or thiophene; and the remaining substituents are as defined in claim 1.

4. A compound of claim 1 of the formula:

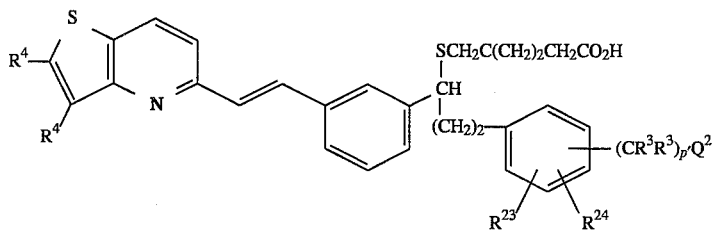

Ic wherein:

R² is lower alkyl or phenyl;

R³ is H, lower alkyl or two R³ joined to the same carbon may form a monocyclic ring from 3 to 6 members, optionally containing one oxygen or one sulfur;

R⁴ is H, halogen or —S(O)₂R²;

R¹⁵ is H, oxetanyl or lower alkyl;

R¹⁸ is lower alkyl;

R²³ and R²⁴ are independently H, halogen, lower alkyl, SR², CF₃, COR³ or C(R³)₂OH;

R¹⁰ is H, lower alkyl or benzyl; p1 p' is 0 or 1; and $Q^2$ is H, C(R³)₂H, P(O)(OR¹⁰)₂, SO₂R¹⁸, CO₂R³ or OR¹⁵.

5. A compound of claim 1 of the formula:

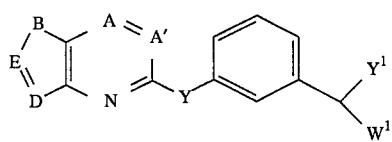

wherein the substituents are as follows:

TABLE 1

| EX | A | A' | B | D | E | Y | Y¹ | W¹ |
|---|---|---|---|---|---|---|---|---|
| 1 | CH | CH | S | CCl | CH | CH=CH | SCH$_2$(1,1-c-Pr)CH$_2$CO$_2$H | (CH$_2$)$_2$(1,2-phe)C(CH$_3$)$_2$OH |
| 2 | CH | CH | S | CH | CH | CH=CH | SCH$_2$(1,1-c-Pr)CH$_2$CO$_2$H | (CH$_2$)$_2$(1,2-phe)C(CH$_3$)$_2$OH |
| 3 | CH | CH | S | CBr | CH | CH=CH | SCH$_2$(1,1-c-Pr)CH$_2$CO$_2$H | (CH$_2$)$_2$(1,2-phe)C(CH$_3$)$_2$OH |
| 4 | CH | CH | S | CCl | CCl | CH=CH | SCH$_2$(1,1-c-Pr)CH$_2$CO$_2$H | (CH$_2$)$_2$(1,2-phe)C(CH$_3$)$_2$OH |
| 5 | CH | CH | S | CCl | CH | CH$_2$CH$_2$ | SCH$_2$(1,1-c-Pr)CH$_2$CO$_2$H | (CH$_2$)$_2$(1,2-phe)C(CH$_3$)$_2$OH |
| 6 | CH | CH | S | CH | CCl | CH=CH | SCH$_2$(1,1-c-Pr)CH$_2$CO$_2$H | (CH$_2$)$_2$(1,2-phe)C(CH$_3$)$_2$OH |
| 7 | CH | CH | S | CH | CF | CH=CH | SCH$_2$(1,1-c-Pr)CH$_2$CO$_2$H | (CH$_2$)$_2$(1,2-phe)C(CH$_3$)$_2$OH |
| 8 | CH | CH | S | CF | CF | CH=CH | SCH$_2$(1,1-c-Pr)CH$_2$CO$_2$H | (CH$_2$)$_2$(1,2-phe)C(CH$_3$)$_2$OH |
| 9 | CH | CH | S | CF | CCl | CH=CH | SCH$_2$(1,1-c-Pr)CH$_2$CO$_2$H | (CH$_2$)$_2$(1,2-phe)C(CH$_3$)$_2$OH |
| 10 | CH | CH | S | CCl | CF | CH=CH | SCH$_2$(1,1-c-Pr)CH$_2$CO$_2$H | (CH$_2$)$_2$(1,2-phe)C(CH$_3$)$_2$OH |
| 11 | CH | CH | S | CH | CS(O)$_2$PH | CH=CH | SCH$_2$(1,1-c-Pr)CH$_2$CO$_2$H | (CH$_2$)$_2$(1,2-phe)C(CH$_3$)$_2$OH |
| 12 | CH | CH | O | CCl | CCl | CH=CH | SCH$_2$(1,1-c-Pr)CH$_2$CO$_2$H | (CH$_2$)$_2$(1,2-phe)C(CH$_3$)$_2$OH |
| 13 | CH | CH | O | CCl | CH | CH=CH | SCH$_2$(1,1-c-pr)CH$_2$CO$_2$H | (CH$_2$)$_2$(1,2-phe)C(CH$_3$)$_2$OH |
| 14 | CH | CH | S | CCl | CCl | CH=CH | OCH$_2$(1,1-c-Pr)CH$_2$CO$_2$H | (CH$_2$)$_2$(1,2-phe)Br |
| 15 | CH | CH | S | CCl | CCl | CH=CH | OCH$_2$(1,1-c-Pr)CH$_2$CO$_2$H | (CH$_2$)$_2$(1,2-phe)C(CH$_3$)$_2$OH |
| 16 | CH | CH | S | CCl | CCl | CH=CH | SCH$_2$C(CH$_3$)$_2$CH$_2$COOH | (CH$_2$)$_2$(1,4-phe)c-Pr |
| 17 | CH | CH | S | CCl | CF | CH=CH | SCH$_2$C(CH$_3$)$_2$CH$_2$COOH | (CH$_2$)$_2$(1,4-phe)c-Pr |
| 18 | CH | CH | S | CCl | CCl | CH=CH | SCH$_2$C(CH$_3$)$_2$CH$_2$COOH | (CH$_2$)$_2$(1,4-phe)c-Pr |
| 19 | CH | CH | S | CF | CF | CH=CH | SCH$_2$C(CH$_3$)$_2$CH$_2$COOH | (CH$_2$)$_2$(1,4-phe)c-Pr |
| 20 | CH | CH | S | CF | CH | CH=CH | SCH$_2$(1,1-c-Pr)CH$_2$CO$_2$H | (CH$_2$)$_2$(1,2-phe)C(CH$_3$)$_2$OH |
| 21 | CH | CH | S | CS(O)$_2$CF$_3$ | CCl | CH=CH | SCH$_2$C(CH$_3$)$_2$CH$_2$COOH | (CH$_2$)$_2$(1,4-phe)c-Pr |
| 22 | CH | CH | S | CF | CS(O)$_2$CF$_3$ | CH=CH | SCH$_2$C(CH$_3$)$_2$CH$_2$COOH | (CH$_2$)$_2$(1,4-phe)c-Pr |
| 23 | CH | CH | S | CCl | CCN | CH=CH | SCH$_2$C(CH$_3$)$_2$CH$_2$COOH | (CH$_2$)$_2$(1,4-phe)c-Pr |
| 24 | CH | CH | S | CBr | CF | CH=CH | SCH$_2$C(CH$_3$)$_2$CH$_2$COOH | (CH$_2$)$_2$(1,4-phe)c-Pr |
| 25 | CH | CH | S | CS(O)$_2$CF$_3$ | CCl | CH=CH | SCH$_2$(1,1-c-Pr)CH$_2$CO$_2$H | (CH$_2$)$_2$(1,2-phe)C(CH$_3$)$_2$OH |
| 26 | CH | CH | S | CF | CS(O)$_2$CH$_3$ | CH=CH | SCH$_2$(1,1-c-Pr)CH$_2$CO$_2$H | (CH$_2$)$_2$(1,2-phe)C(CH$_3$)$_2$OH |
| 27 | CH | CH | S | CCl | CCN | CH=CH | SCH$_2$(1,1-c-Pr)CH$_2$CO$_2$H | (CH$_2$)$_2$(1,2-phe)C(CH$_3$)$_2$OH |
| 28 | CH | CH | O | CH | CCl | CH=CH | SCH$_2$(1,1-c-Pr)CH$_2$CO$_2$H | (CH$_2$)$_2$(1,2-phe)C(CH$_3$)$_2$OH |
| 29 | CH | CH | O | CH | CH | CH=CH | SCH$_2$(1,1-c-Pr)CH$_2$CO$_2$H | (CH$_2$)$_2$(1,2-phe)C(CH$_3$)$_2$OH |
| 30 | CH | CH | S | N | CCF$_3$ | CH=CH | SCH$_2$(1,1-c-Pr)CH$_2$CO$_2$H | (CH$_2$)$_2$(1,2-phe)Br |
| 31 | CH | CH | O | CH | CF | CH=CH | SCH$_2$(1,1-c-Pr)CH$_2$COOH | (CH$_2$)$_2$(1,2-phe)C(CH$_3$)$_2$OH |
| 32 | CH | CH | O | CF | CH | CH=CH | SCH$_2$(1,1-c-Pr)CH$_2$CO$_2$H | (CH$_2$)$_2$(1,2-phe)C(CH$_3$)$_2$OH |
| 33 | CH | CH | O | CF | CCl | CH=CH | SCH$_2$(1,1-c-Pr)CH$_2$CO$_2$H | (CH$_2$)$_2$(1,2-phe)C(CH$_3$)$_2$OH |
| 34 | CH | CH | O | CCl | CF | CH=CH | SCH$_2$(1,1-c-Pr)CH$_2$CO$_2$H | (CH$_2$)$_2$(1,2-phe)C(CH$_3$)$_2$OH |
| 35 | N | CH | S | CH | CF | CH=CH | SCH$_2$(1,1-c-Pr)CH$_2$COOH | (CH$_2$)$_2$Ph |
| 36 | CH | CH | O | CF | CF | CH=CH | SCH$_2$(1,1-c-Pr)CH$_2$CO$_2$H | (CH$_2$)$_2$(1,2-phe)C(CH$_3$)$_2$OH |
| 37 | CH | CH | O | CS(O)$_2$CF$_3$ | CCl | CH=CH | SCH$_2$(1,1-c-Pr)CH$_2$CO$_2$H | (CH$_2$)$_2$(1,2-phe)C(CH$_3$)$_2$OH |
| 38 | CH | CH | O | CF | CS(O)$_2$CF$_3$ | CH=CH | SCH$_2$(1,1-c-Pr)CH$_2$CO$_2$H | (CH$_2$)$_2$(1,2-phe)C(CH$_3$)$_2$OH |
| 39 | CH | CH | O | CCl | CCN | CH=CH | SCH$_2$(1,1-c-Pr)CH$_2$CO$_2$H | (CH$_2$)$_2$(1,2-phe)C(CH$_3$)$_2$OH |
| 40 | CH | CH | O | CBr | CF | CH=CH | SCH$_2$(1,1-c-Pr)CH$_2$CO$_2$H | (CH$_2$)$_2$(1,2-phe)C(CH$_3$)$_2$OH |
| 41 | CH | CH | S | CH | CH | CH=CH | SCH$_2$(1,1-c-Pr)CH$_2$CO$_2$H | (CH$_2$)$_2$(1,2-phe)Br |
| 42 | CH | CH | S | CH | CCl | CH=CH | SCH$_2$(1,1-c-Pr)CH$_2$CO$_2$H | (CH$_2$)$_2$(1,2-phe)Br |
| 43 | CH | CH | S | CCl | CH | CH=CH | SCH$_2$(1,1-c-Pr)CH$_2$CO$_2$H | (CH$_2$)$_2$(1,2-phe)Br |
| 44 | CH | CH | S | CH | CF | CH=CH | SCH$_2$(1,1-c-Pr)CH$_2$CO$_2$H | (CH$_2$)$_2$(1,2-phe)Br |
| 45 | CH | CH | S | CF | CH | CH=CH | SCH$_2$(1,1-c-Pr)CH$_2$CO$_2$H | (CH$_2$)$_2$(1,2-phe)Br |
| 46 | CH | CH | S | CF | CCl | CH=CH | SCH$_2$(1,1-c-Pr)CH$_2$CO$_2$H | (CH$_2$)$_2$(1,2-phe)Br |
| 47 | CH | CH | S | CCl | CF | CH=CH | SCH$_2$(1,1-c-Pr)CH$_2$CO$_2$H | (CH$_2$)$_2$(1,2-phe)Br |
| 48 | CH | CH | S | CCl | CCl | CH=CH | SCH$_2$(1,1-c-Pr)CH$_2$CO$_2$H | (CH$_2$)$_2$(1,4-phe)c-Pr |
| 49 | CH | CH | S | CF | CF | CH=CH | SCH$_2$(1,1-c-Pr)CH$_2$CO$_2$H | (CH$_2$)$_2$(1,2-phe)Br |
| 50 | CH | CH | S | CS(O)$_2$CF$_3$ | CCl | CH=CH | SCH$_2$(1,1-c-Pr)CH$_2$CO$_2$H | (CH$_2$)$_2$(1,2-phe)Br |
| 51 | CH | CH | S | CF | CS(O)$_2$CH$_3$ | CH=CH | SCH$_2$(1,1-c-Pr)CH$_2$CO$_2$H | (CH$_2$)$_2$(1,2-phe)Br |
| 52 | CH | CH | S | CCl | CCN | CH=CH | SCH$_2$(1,1-c-Pr)CH$_2$CO$_2$H | (CH$_2$)$_2$(1,2-phe)Br |
| 53 | CH | CH | O | CH | CCl | CH=CH | SCH$_2$(1,1-c-Pr)CH$_2$CO$_2$H | (CH$_2$)$_2$(1,2-phe)Br |
| 54 | CH | CH | S | CH | CH | CH=CH | SCH$_2$(1,1-c-Pr)CH$_2$CO$_2$H | (CH$_2$)$_2$(1,2-phe)Br |
| 55 | CH | CH | S | CCl | CH | CH=CH | SCH$_2$(1,1-c-Pr)CH$_2$CO$_2$H | (CH$_2$)$_2$(1,2-phe)Br |
| 56 | CH | CH | S | CH | CF | CH=CH | SCH$_2$(1,1-c-Pr)CH$_2$CO$_2$H | (CH$_2$)$_2$(1,2-phe)Br |
| 57 | CH | CH | S | CF | CH | CH=CH | SCH$_2$(1,1-c-Pr)CH$_2$CO$_2$H | (CH$_2$)$_2$(1,2-phe)Br |
| 58 | CH | CH | S | CF | CCl | CH=CH | SCH$_2$(1,1-c-Pr)CH$_2$CO$_2$H | (CH$_2$)$_2$(1,2-phe)Br |
| 59 | CH | CH | S | CCl | CF | CH=CH | SCH$_2$(1,1-c-Pr)CH$_2$CO$_2$H | (CH$_2$)$_2$(1,2-phe)Br |
| 60 | CH | CH | S | CCl | CCl | CH=CH | SCH$_2$(1,1-c-Pr)CH$_2$CO$_2$H | (CH$_2$)$_2$(1,2-phe)Br |
| 61 | CH | CH | S | CF | CF | CH=CH | SCH$_2$(1,1-c-Pr)CH$_2$CO$_2$H | (CH$_2$)$_2$(1,2-phe)Br |
| 62 | CH | CH | S | CS(O)$_2$CF$_3$ | CCl | CH=CH | SCH$_2$(1,1-c-Pr)CH$_2$CO$_2$H | (CH$_2$)$_2$(1,2-phe)Br |
| 63 | CH | CH | S | CF | CS(O)$_2$CF$_3$ | CH=CH | SCH$_2$(1,1-c-Pr)CH$_2$CO$_2$H | (CH$_2$)$_2$(1,2-phe)Br |
| 64 | CH | CH | S | CCl | CCN | CH=CH | SCH$_2$(1,1-c-Pr)CH$_2$CO$_2$H | (CH$_2$)$_2$(1,2-phe)Br |
| 65 | CH | CH | S | CBr | CF | CH=CH | SCH$_2$(1,1-c-Pr)CH$_2$CO$_2$H | (CH$_2$)$_2$(1,2-phe)Br |
| 66 | CH | CH | S | CH | CH | CH=CH | SCH$_2$(1,1-c-Pr)CH$_2$CO$_2$H | (CH$_2$)$_2$(1,4-phe)(1,1-c-Bu)OH |
| 67 | CH | CH | S | CH | CCl | CH=CH | SCH$_2$(1,1-c-Pr)CH$_2$CO$_2$H | (CH$_2$)$_2$(1,4-phe)(1,1-c-Bu)OH |
| 68 | CH | CH | S | CCl | CH | CH=CH | SCH$_2$(1,1-c-Pr)CH$_2$CO$_2$H | (CH$_2$)$_2$(1,4-phe)(1,1-c-Bu)OH |
| 69 | CH | CH | S | CH | CF | CH=CH | SCH$_2$(1,1-c-Pr)CH$_2$CO$_2$H | (CH$_2$)$_2$(1,4-phe)(1,1-c-Bu)OH |
| 70 | CH | CH | S | CF | CH | CH=CH | SCH$_2$(1,1-c-Pr)CH$_2$CO$_2$H | (CH$_2$)$_2$(1,4-phe)(1,1-c-Bu)OH |
| 71 | CH | CH | S | CF | CCl | CH=CH | SCH$_2$(1,1-c-Pr)CH$_2$CO$_2$H | (CH$_2$)$_2$(1,4-phe)(1,1-c-Bu)OH |
| 72 | CH | CH | S | CCl | CF | CH=CH | SCH$_2$(1,1-c-Pr)CH$_2$CO$_2$H | (CH$_2$)$_2$(1,4-phe)(1,1-c-Bu)OH |
| 73 | CH | CH | S | CCl | CCl | CH=CH | SCH$_2$(1,1-c-Pr)CH$_2$CO$_2$H | (CH$_2$)$_2$(1,4-phe)(1,1-c-Bu)OH |
| 74 | CH | CH | S | CF | CF | CH=CH | SCH$_2$(1,1-c-Pr)CH$_2$CO$_2$H | (CH$_2$)$_2$(1,4-phe)(1,1-c-Bu)OH |
| 75 | CH | CH | S | CS(O)$_2$CF$_3$ | CCl | CH=CH | SCH$_2$(1,1-c-Pr)CH$_2$CO$_2$H | (CH$_2$)$_2$(1,4-phe)(1,1-c-Bu)OH |
| 76 | CH | CH | S | CF | CS(O)$_2$CH$_3$ | CH=CH | SCH$_2$(1,1-c-Pr)CH$_2$CO$_2$H | (CH$_2$)$_2$(1,4-phe)(1,1-c-Bu)OH |
| 77 | CH | CH | S | CCl | CCN | CH=CH | SCH$_2$(1,1-c-Pr)CH$_2$CO$_2$H | (CH$_2$)$_2$(1,4-phe)(1,1-c-Bu)OH |

TABLE 1-continued

| EX | A | A' | B | D | E | Y | Y¹ | W¹ |
|---|---|---|---|---|---|---|---|---|
| 78 | CH | CH | O | CH | CCl | CH=CH | SCH$_2$(1,1-c-Pr)CH$_2$CO$_2$H | (CH$_2$)$_2$(1,4-phe)(1,1-c-Bu)OH |
| 79 | CH | CH | S | CH | CH | CH=CH | SCH$_2$(1,1-c-Pr)CH$_2$CO$_2$H | (CH$_2$)$_2$(1,4-phe)(1,1-c-Bu)OH |
| 80 | CH | CH | S | CCl | CH | CH=CH | SCH$_2$(1,1-c-Pr)CH$_2$CO$_2$H | (CH$_2$)$_2$(1,4-phe)(1,1-c-Bu)OH |
| 81 | CH | CH | S | CH | CF | CH=CH | SCH$_2$(1,1-c-Pr)CH$_2$CO$_2$H | (CH$_2$)$_2$(1,4-phe)(1,1-c-Bu)OH |
| 82 | CH | CH | S | CF | CH | CH=CH | SCH$_2$(1,1-c-Pr)CH$_2$CO$_2$H | (CH$_2$)$_2$(1,4-phe)(1,1-c-Bu)OH |
| 83 | CH | CH | S | CF | CCl | CH=CH | SCH$_2$(1,1-c-Pr)CH$_2$CO$_2$H | (CH$_2$)$_2$(1,4-phe)(1,1-c-Bu)OH |
| 84 | CH | CH | S | CCl | CF | CH=CH | SCH$_2$(1,1-c-Pr)CH$_2$CO$_2$H | (CH$_2$)$_2$(1,4-phe)(1,1-c-Bu)OH |
| 85 | CH | CH | S | CCl | CCl | CH=CH | SCH$_2$(1,1-c-Pr)CH$_2$CO$_2$H | (CH$_2$)$_2$(1,4-phe)(1,1-c-Bu)OH |
| 86 | CH | CH | S | CF | CF | CH=CH | SCH$_2$(1,1-c-Pr)CH$_2$CO$_2$H | (CH$_2$)$_2$(1,4-phe)(1,1-c-Bu)OH |
| 87 | CH | CH | S | CS(O)$_2$CF$_3$ | CCl | CH=CH | SCH$_2$(1,1-c-Pr)CH$_2$CO$_2$H | (CH$_2$)$_2$(1,4-phe)(1,1-c-Bu)OH |
| 88 | CH | CH | S | CF | CS(O)$_2$CF$_3$ | CH=CH | SCH$_2$(1,1-c-Pr)CH$_2$CO$_2$H | (CH$_2$)$_2$(1,4-phe)(1,1-c-Bu)OH |
| 89 | CH | CH | S | CCl | CCN | CH=CH | SCH$_2$(1,1-c-Pr)CH$_2$CO$_2$H | (CH$_2$)$_2$(1,4-phe)(1,1-c-Bu)OH |
| 90 | CH | CH | S | CBr | CF | CH=CH | SCH$_2$(1,1-c-Pr)CH$_2$CO$_2$H | (CH$_2$)$_2$(1,4-phe)(1,1-c-Bu)OH |
| 91 | CH | CH | S | CH | CH | CH=CH | SCH$_2$C(CH$_3$)$_2$CH$_2$COOH | (CH$_2$)$_2$(1,4-phe)c-Pr |
| 92 | CH | CH | S | CH | CCl | CH=CH | SCH$_2$C(CH$_3$)$_2$CH$_2$COOH | (CH$_2$)$_2$(1,4-phe)c-Pr |
| 93 | CH | CH | S | CCl | CH | CH=CH | SCH$_2$C(CH$_3$)$_2$CH$_2$COOH | (CH$_2$)$_2$(1,4-phe)c-Pr |
| 94 | CH | CH | S | CH | CF | CH=CH | SCH$_2$C(CH$_3$)$_2$CH$_2$COOH | (CH$_2$)$_2$(1,4-phe)c-Pr |
| 95 | CH | CH | S | CF | CH | CH=CH | SCH$_2$C(CH$_3$)$_2$CH$_2$COOH | (CH$_2$)$_2$(1,4-phe)c-Pr |
| 96 | CH | CH | S | CF | CCl | CH=CH | SCH$_2$C(CH$_3$)$_2$CH$_2$COOH | (CH$_2$)$_2$(1,4-phe)c-Pr |
| 97 | CH | CH | S | CCl | CF | CH=CH | SCH$_2$C(CH$_3$)$_2$CH$_2$COOH | (CH$_2$)$_2$(1,4-phe)c-Pr |
| 98 | CH | CH | S | CCl | CCl | CH=CH | OCH$_2$(1,1-c-Pr)CH$_2$CO$_2$H | (CH$_2$)$_2$(1,2-phe)Br |
| 99 | CH | CH | S | CF | CF | CH=CH | SCH$_2$C(CH$_3$)$_2$CH$_2$COOH | (CH$_2$)$_2$(1,4-phe)c-Pr |
| 100 | CH | CH | S | CS(O)$_2$CF$_3$ | CCl | CH=CH | SCH$_2$C(CH$_3$)$_2$CH$_2$COOH | (CH$_2$)$_2$(1,4-phe)c-Pr |
| 101 | CH | CH | S | CF | CS(O)$_2$CH$_3$ | CH=CH | SCH$_2$C(CH$_3$)$_2$CH$_2$COOH | (CH$_2$)$_2$(1,4-phe)c-Pr |
| 102 | CH | CH | S | CCl | CCN | CH=CH | SCH$_2$C(CH$_3$)$_2$CH$_2$COOH | (CH$_2$)$_2$(1,4-phe)c-Pr |
| 103 | CH | CH | O | CH | CCl | CH=CH | SCH$_2$C(CH$_3$)$_2$CH$_2$COOH | (CH$_2$)$_2$(1,4-phe)c-Pr |
| 104 | CH | CH | S | CH | CH | CH=CH | SCH$_2$C(CH$_3$)$_2$CH$_2$COOH | (CH$_2$)$_2$(1,4-phe)c-Pr |
| 105 | CH | CH | S | CCl | CH | CH=CH | SCH$_2$C(CH$_3$)$_2$CH$_2$COOH | (CH$_2$)$_2$(1,4-phe)c-Pr |
| 106 | CH | CH | S | CH | CF | CH=CH | SCH$_2$C(CH$_3$)$_2$CH$_2$COOH | (CH$_2$)$_2$(1,4-phe)c-Pr |
| 107 | CH | CH | S | CF | CH | CH=CH | SCH$_2$C(CH$_3$)$_2$CH$_2$COOH | (CH$_2$)$_2$(1,4-phe)c-Pr |
| 108 | CH | CH | S | CF | CCl | CH=CH | SCH$_2$C(CH$_3$)$_2$CH$_2$COOH | (CH$_2$)$_2$(1,4-phe)c-Pr |
| 124 | CH | CH | S | CCl | CCl | CH=CH | SCH$_2$(1,1-c-Pr)CH$_2$CO$_2$H | (CH$_2$)$_2$(1,3-phe)-O-c-Pr |
| 125 | CH | CH | S | CCl | CCl | CH=CH | SCH$_2$(1,1-c-Pr)CH$_2$CO$_2$H | (CH$_2$)$_2$(1,4-phe)-I |
| 126 | CH | CH | S | CCl | CCl | CH=CH | SCH$_2$(1,1-c-Pr)CH$_2$CO$_2$H | (CH$_2$)$_2$(1,4-phe)C((CH$_2$)$_3$)OH |
| 127 | CH | CH | S | CCl | CCl | CH=CH | SCH$_2$(1,1-c-pr)CH$_2$CO$_2$H | (CH$_2$)$_2$(1,4-phe)Br |
| 128 | CH | CH | S | CCl | CCl | CH=CH | SCH$_2$(1,1-c-pr)CH$_2$CO$_2$H | (CH$_2$)$_2$(1,4-phe)Oc-pr |
| 129 | CH | CH | S | CCl | CCl | CH=CH | SCH$_2$C(CH$_3$)$_2$CH$_2$COOH | (CH$_2$)$_2$(1,4-phe)Br |
| 130 | CH | CH | S | CCl | CCl | CH=CH | SCH$_2$(1,1-c-Pr)CH$_2$CO$_2$H | (CH$_2$)$_2$(2,5-thi)Cl |
| 131 | CH | CH | S | CCl | CCl | CH=CH | S(1,1-c-pr)CH$_2$CO$_2$H | (CH$_2$)$_2$(1,4-phe)Br |
| 132 | CH | CH | S | CCl | CCl | CH=CH | SCH$_2$(1,1-c-pr)CH$_2$CO$_2$H | (CH$_2$)$_2$(1,4-phe)C(CH$_2$)$_2$OCH$_3$ |
| 133 | CH | CH | S | CCl | CCl | CH=CH | SCH$_2$(1,1-c-pr)CH$_2$CO$_2$H | (CH$_2$)$_2$(1,4-phe)F |
| 134 | CH | CH | S | CCl | CCl | CH=CH | SCH$_2$(1,1-c-pr)CH$_2$CO$_2$H | (CH$_2$)$_2$(1,4-phe)C(CH$_3$)$_2$OH |
| 135 | CH | CH | S | CCl | CCl | CH=CH | SCH$_2$(1,1-c-pr)CH$_2$CO$_2$H | (CH$_2$)$_2$(1,4-phe)Cl |
| 136 | CH | CH | O | CCl | CCl | CH=CH | SCH$_2$(1,1-c-pr)CH$_2$CO$_2$H | (CH$_2$)$_2$(2-th) |
| 137 | CH | CH | S | CCl | CCl | CH=CH | SCH$_2$(1,1-c-pr)CH$_2$CO$_2$H | (CH$_2$)$_2$(1,4-phe)CF$_3$ |
| 138 | CH | CH | S | CCl | CCl | CH=CH | SCH$_2$(1,1-c-pr)CH$_2$CO$_2$H | (CH$_2$)$_2$(1,3-phe)(1,1-c-Bu)OH |
| 139 | CH | CH | S | CCl | CCl | CH=CH | SCH$_2$(1,1-c-pr)CH$_2$CO$_2$H | (CH$_2$)$_2$(1,4-phe)SO$_2$-c-pr |
| 140 | CH | CH | S | CCl | CCl | CH=CH | SCH$_2$(1,1-c-pr)CH$_2$CO$_2$H | (CH$_2$)$_2$(1,2-phe)(1,1-c-Bu)OH |
| 141 | CH | CH | S | CCl | CBr | CH=CH | SCH$_2$(1,1-c-pr)CH$_2$CO$_2$H | (CH$_2$)$_2$(1,2-phe)C(CH$_3$)$_2$OH |
| 142 | CH | CH | S | CCl | CBr | CH=CH | SCH$_2$(1,1-c-pr)CH$_2$CO$_2$H | (CH$_2$)$_2$(1,4-phe)C(CH$_3$)$_2$OH |
| 143 | CH | CH | S | CCl | CCl | CH=CH | SCH$_2$(1,1-c-pr)CH$_2$CO$_2$H | (CH$_2$)$_2$(4-F-1,2-phe)C(CH$_3$)$_2$OH |
| 144 | CH | CH | S | CCl | CCl | CH=CH | SCH$_2$(1,1-c-pr)CH$_2$CO$_2$H | (CH$_2$)$_2$(4-Cl-1,2-phe)C(CH$_3$)$_2$OH |
| 145 | CH | CH | S | CCl | CCl | CH=CH | SCH$_2$(1,1-c-pr)CH$_2$CO$_2$H | (CH$_2$)$_2$(4-Cl-1,2-phe)(1,1-c-Bu)OH |
| 146 | CH | CH | S | CCl | CCl | CH=CH | SCH$_2$(1,1-c-pr)CH$_2$CO$_2$H | (CH$_2$)$_2$(1,2-phe)CH$_2$OH |
| 147 | CH | CH | S | CCl | CCl | CH=CH | SCH$_2$(1,1-c-pr)CH$_2$CO$_2$H | (CH$_2$)$_2$(1,2-phe)CO$_2$CH$_3$ |
| 148 | CH | CH | S | CCl | CCl | CH=CH | SCH$_2$(1,1-c-pr)CH$_2$CO$_2$H | (CH$_2$)$_2$(1,2-phe)(1,1-c-Hex)OH |
| 149 | CH | CH | S | CCl | CCl | CH=CH | SCH$_2$(1,1-c-pr)CH$_2$CO$_2$H | (CH$_2$)$_2$(4-Cl-1,2-phe)CH$_2$OH |
| 150 | CH | CH | S | CCl | CCl | CH=CH | SCH$_2$(1,1-c-pr)CH$_2$CO$_2$H | (CH$_2$)$_2$Ph |
| 151 | CH | CH | S | CCl | CBr | CH=CH | SCH$_2$(1,1-c-pr)CH$_2$CO$_2$H | (CH$_2$)$_2$(1,2-phe)C(CH$_3$)$_2$OH |
| 152 | CH | CH | S | CCl | CCl | CH=CH | SCH$_2$(1,1-c-pr)CH$_2$CO$_2$H | (CH$_2$)$_2$(6-Br-1,2-phe)CH$_2$OH |
| 153 | CH | CH | S | CCl | CCl | CH=CH | SCH$_2$(1,1-c-pr)CH$_2$CO$_2$H | (CH$_2$)$_2$(1,2-phe)COCH$_3$ |
| 154 | CH | CH | S | CCl | CCl | CH=CH | SCH$_2$(1,1-c-pr)CH$_2$CO$_2$H | (CH$_2$)$_2$TdzH |
| 155 | CH | CH | S | CCl | CCl | CH=CH | SCH$_2$(1,1-c-pr)CH$_2$CO$_2$H | (CH$_2$)$_2$(1,2-phe)CH(OH)CH$_3$ |
| 156 | CH | CH | S | CCl | CCl | CH=CH | SCH$_2$(1,1-c-pr)CH$_2$CO$_2$H | (CH$_2$)$_2$(1,2-phe)C(CH$_3$)$_2$OCH$_3$ |
| 157 | CH | CH | S | CCl | CCl | CH=CH | SCH$_2$(1,1-c-pr)CH$_2$CO$_2$H | (CH$_2$)$_2$(6-Br-1,2-phe)C(CH$_3$)$_2$OH |
| 158 | CH | CH | S | CCl | CBr | CH=CH | SCH$_2$(1,1-c-pr)CH$_2$CO$_2$H | (CH$_2$)$_2$(1,3-Phe)Br |
| 159 | CH | CH | S | CCl | CBr | CH=CH | S(1,1-c-pr)CH$_2$CO$_2$H | (CH$_2$)$_2$(1,2-Phe)Br |
| 160 | CH | CH | S | CCl | CCl | CH=CH | SCH$_2$(1,1-c-pr)CH$_2$CO$_2$H | (CH$_2$)$_2$(1,3-Phe)F |
| 161 | CH | CH | S | CCl | CBr | CH=CH | SCH$_2$(1,1-c-pr)CH$_2$CO$_2$H | (CH$_2$)$_2$(1,3-Phe)Cl |
| 162 | CH | CH | S | CCl | CF | CH=CH | S(1,1-c-pr)CH$_2$CO$_2$H | (CH$_2$)$_2$(1,3-Phe)Cl |
| 163 | CH | CH | S | CCl | CF | CH=CH | SCH$_2$(1,1-c-pr)CH$_2$CO$_2$H | (CH$_2$)$_2$(1,3-Phe)C(CH$_3$)$_2$OH |
| 164 | CH | CH | S | CCl | CCl | CH=CH | SCH$_2$(1,1-c-pr)CH$_2$CO$_2$H | (CH$_2$)$_2$(5-((1,1-c-Bu)OH)-1,3-phe)-(1,1-c-Bu)OH |
| 165 | CH | CH | S | CCl | CCl | CH=CH | SCH$_2$(1,1-c-pr)CH$_2$CO$_2$H | (CH$_2$)$_2$(1,3-phe)F |
| 166 | CH | CH | S | CCl | CCl | CH=CH | SCH$_2$(1,1-c-pr)CH$_2$CO$_2$H | (CH$_2$)$_2$Thz |
| 167 | CH | CH | S | CCl | CCl | CH=CH | SCH$_2$(1,1-c-pr)CH$_2$CO$_2$H | (CH$_2$)$_2$(1,2-phe)CF$_3$ |
| 168 | CH | CH | S | CCl | CCl | CH=CH | SCH$_2$(1,1-c-pr)CH$_2$CO$_2$H | (CH$_2$)$_2$(1,2-phe)O-OX |

TABLE 1-continued

| EX | A | A' | B | D | E | Y | Y¹ | W¹ |
|---|---|---|---|---|---|---|---|---|
| 169 | CH | CH | S | CCl | CCl | CH=CH | SCH$_2$(1,1-c-pr)CH$_2$CO$_2$H | (CH$_2$)$_2$(1,2-phe)(4-OH-T4P) |
| 170 | CH | CH | S | CCl | CCl | CH=CH | SCH$_2$(1,1-c-pr)CH$_2$CO$_2$H | (CH$_2$)$_2$(1,3-phe)P(O)(OCH$_2$CH$_3$)$_2$ |
| 171 | CH | CH | S | CCl | CCl | CH=CH | SCH$_2$(1,1-c-pr)CH$_2$CO$_2$H | (CH$_2$)$_2$(1,4-phe)S-c-Pr |
| 172 | CH | CH | S | CCl | CF | CH=CH | SCH$_2$(1,1-c-pr)CH$_2$CO$_2$H | (CH$_2$)$_2$(1,4-phe)C(CH$_3$)$_2$OH |
| 173 | CH | CH | S | CCl | CF | CH=CH | SCH$_2$(1,1-c-pr)CH$_2$CO$_2$H | (CH$_2$)$_2$(1,3-phe)C(CH$_3$)$_2$OH |
| 174 | CH | CH | S | CCl | CH | O—CH$_2$ | SCH$_2$(1,1-c-Pr)CH$_2$CO$_2$H | (CH$_2$)$_2$(1,2-phe)C(CH$_3$)$_2$OH |
| 175 | CH | CH | S | CH | CH | O—CH$_2$ | SCH$_2$(1,1-c-Pr)CH$_2$CO$_2$H | (CH$_2$)$_2$(1,2-phe)C(CH$_3$)$_2$OH |
| 176 | CH | CH | S | CH | CCl | O—CH$_2$ | SCH$_2$(1,1-c-Pr)CH$_2$CO$_2$H | (CH$_2$)$_2$(1,2-phe)C(CH$_3$)$_2$OH |
| 177 | CH | CH | S | CH | CF | O—CH$_2$ | SCH$_2$(1,1-c-Pr)CH$_2$CO$_2$H | (CH$_2$)$_2$(1,2-phe)C(CH$_3$)$_2$OH |
| 178 | CH | CH | S | CCl | CCl | O—CH$_2$ | SCH$_2$(1,1-c-Pr)CH$_2$CO$_2$H | (CH$_2$)$_2$(1,2-phe)C(CH$_3$)$_2$OH |
| 179 | CH | CH | S | CH | CBr | O—CH$_2$ | SCH$_2$(1,1-c-Pr)CH$_2$CO$_2$H | (CH$_2$)$_2$(1,2-phe)C(CH$_3$)$_2$OH |
| 180 | CH | CH | S | CF | CH | O—CH$_2$ | SCH$_2$(1,1-c-Pr)CH$_2$CO$_2$H | (CH$_2$)$_2$(1,2-phe)C(CH$_3$)$_2$OH |
| 181 | CH | CH | S | CCl | CH | CH$_2$—O | SCH$_2$(1,1-c-Pr)CH$_2$CO$_2$H | (CH$_2$)$_2$(1,2-phe)C(CH$_3$)$_2$OH |
| 182 | CH | CH | S | CH | CH | CH$_2$—O | SCH$_2$(1,1-c-Pr)CH$_2$CO$_2$H | (CH$_2$)$_2$(1,2-phe)C(CH$_3$)$_2$OH |
| 183 | CH | CH | S | CH | CCl | CH$_2$—O | SCH$_2$(1,1-c-Pr)CH$_2$CO$_2$H | (CH$_2$)$_2$(1,2-phe)C(CH$_3$)$_2$OH |
| 184 | CH | CH | S | CH | CF | CH$_2$—O | SCH$_2$(1,1-c-Pr)CH$_2$CO$_2$H | (CH$_2$)$_2$(1,2-phe)C(CH$_3$)$_2$OH |
| 185 | CH | CH | S | CCl | CCl | CH$_2$—O | SCH$_2$(1,1-c-Pr)CH$_2$CO$_2$H | (CH$_2$)$_2$(1,2-phe)C(CH$_3$)$_2$OH |
| 186 | CH | CH | S | CH | CBr | CH$_2$—O | SCH$_2$(1,1-c-Pr)CH$_2$CO$_2$H | (CH$_2$)$_2$(1,2-phe)C(CH$_3$)$_2$OH |
| 187 | CH | CH | S | CF | CH | CH$_2$—O | SCH$_2$(1,1-c-Pr)CH$_2$CO$_2$H | (CH$_2$)$_2$(1,2-phe)C(CH$_3$)$_2$OH |
| 188 | CH | CH | S | CCl | CH | CH=CH | S(CH$_2$)$_2$CO$_2$H | S(CH$_2$)$_2$CON(CH$_3$)$_2$ |
| 189 | CH | CH | S | CH | CH | CH=CH | S(CH$_2$)$_2$CO$_2$H | S(CH$_2$)$_2$CON(CH$_3$)$_2$ |
| 190 | CH | CH | S | CH | CCl | CH=CH | S(CH$_2$)$_2$CO$_2$H | S(CH$_2$)$_2$CON(CH$_3$)$_2$ |
| 191 | CH | CH | S | CH | CF | CH=CH | S(CH$_2$)$_2$CO$_2$H | S(CH$_2$)$_2$CON(CH$_3$)$_2$ |
| 192 | CH | CH | S | CCl | CCl | CH=CH | S(CH$_2$)$_2$CO$_2$H | S(CH$_2$)$_2$CON(CH$_3$)$_2$ |
| 193 | CH | CH | S | CH | CPr | CH=CH | S(CH$_2$)$_2$CO$_2$H | S(CH$_2$)$_2$CON(CH$_3$)$_2$ |
| 194 | CH | CH | O | CH | CH | CH=CH | S(CH$_2$)$_2$CO$_2$H | S(CH$_2$)$_2$CON(CH$_3$)$_2$ |
| 195 | CH | CH | O | CCl | CH | CH=CH | S(CH$_2$)$_2$CO$_2$H | S(CH$_2$)$_2$CON(CH$_3$)$_2$ |
| 196 | CH | CH | O | CBr | CH | CH=CH | S(CH$_2$)$_2$CO$_2$H | S(CH$_2$)$_2$CON(CH$_3$)$_2$ |
| 197 | CH | CH | S | CF | CF | O—CH$_2$ | SCH$_2$(1,1-c-Pr)CH$_2$CO$_2$H | (CH$_2$)$_2$(1,2-phe)C(CH$_3$)$_2$OH |
| 198 | CH | CH | S | CF | CF | CH$_2$—O | SCH$_2$(1,1-c-Pr)CH$_2$CO$_2$H | (CH$_2$)$_2$(1,2-phe)C(CH$_3$)$_2$OH |
| 199 | CH | CH | S | CF | CF | CH=CH | S(CH$_2$)$_2$CO$_2$H | S(CH$_2$)$_2$CON(CH$_3$)$_2$ |
| 200 | CH | CH | S | CCl | CH | 1,2-c-Pr | SCH$_2$(1,1-c-Pr)CH$_2$CO$_2$H | (CH$_2$)$_2$(1,2-phe)C(CH$_3$)$_2$OH |
| 201 | CH | CH | S | CH | CH | 1,2-c-Pr | SCH$_2$(1,1-c-Pr)CH$_2$CO$_2$H | (CH$_2$)$_2$(1,2-phe)C(CH$_3$)$_2$OH |
| 202 | CH | CH | S | CH | CCl | 1,2-c-Pr | SCH$_2$(1,1-c-Pr)CH$_2$CO$_2$H | (CH$_2$)$_2$(1,2-phe)C(CH$_3$)$_2$OH |
| 203 | CH | CH | S | CH | CF | 1,2-c-Pr | SCH$_2$(1,1-c-Pr)CH$_2$CO$_2$H | (CH$_2$)$_2$(1,2-phe)C(CH$_3$)$_2$OH |
| 204 | CH | CH | S | CBr | CH | 1,2-c-Pr | SCH$_2$(1,1-c-Pr)CH$_2$CO$_2$H | (CH$_2$)$_2$(1,2-phe)C(CH$_3$)$_2$OH |
| 205 | CH | CH | O | CH | CH | 1,2-c-Pr | SCH$_2$(1,1-c-Pr)CH$_2$CO$_2$H | (CH$_2$)$_2$(1,2-phe)C(CH$_3$)$_2$OH |
| 206 | CH | CH | O | CCl | CH | 1,2-c-Pr | SCH$_2$(1,1-c-Pr)CH$_2$CO$_2$H | (CH$_2$)$_2$(1,2-phe)C(CH$_3$)$_2$OH |
| 207 | CH | CH | O | CBr | CH | 1,2-c-Pr | SCH$_2$(1,1-c-Pr)CH$_2$CO$_2$H | (CH$_2$)$_2$(1,2-phe)C(CH$_3$)$_2$OH |
| 208 | CH | CH | S | CH | CH | CH=CH | SCH$_2$(1,1-c-Pr)CH$_2$CO$_2$H | (CH$_2$)$_2$S(1,4-phe)F |
| 209 | CH | CH | S | CCl | CH | CH=CH | SCH$_2$(1,1-c-Pr)CH$_2$CO$_2$H | (CH$_2$)$_2$S(1,4-phe)F |
| 210 | CH | CH | S | CH | CCl | CH=CH | SCH$_2$(1,1-c-Pr)CH$_2$CO$_2$H | (CH$_2$)$_2$S(1,4-phe)F |
| 211 | CH | CH | S | CH | CF | CH=CH | SCH$_2$(1,1-c-Pr)CH$_2$CO$_2$H | (CH$_2$)$_2$S(1,4-phe)F |
| 212 | CH | CH | S | CH | CH | CH=CH | SCH$_2$(1,1-c-Pr)CH$_2$CO$_2$H | (CH$_2$)$_2$S(1,4-phe)F |
| 213 | CH | CH | S | CCl | CH | CH=CH | SCH$_2$(1,1-c-Pr)CH$_2$CO$_2$H | (CH$_2$)$_2$S(1,4-phe)F |
| 214 | CH | CH | S | CBr | CH | CH=CH | SCH$_2$(1,1-c-Pr)CH$_2$CO$_2$H | (CH$_2$)$_2$S(1,4-phe)F |
| 215 | CH | CH | S | CH | CH | CH=CH | SCH$_2$(1,1-c-Pr)CH$_2$CO$_2$H | (CH$_2$)$_2$S(1,4-phe)Cl |
| 216 | CH | CH | S | CCl | CH | CH=CH | SCH$_2$(1,1-c-Pr)CH$_2$CO$_2$H | (CH$_2$)$_2$S(1,4-phe)Cl |
| 217 | CH | CH | S | CBr | CH | CH=CH | SCH$_2$(1,1-c-Pr)CH$_2$CO$_2$H | (CH$_2$)$_2$S(1,4-phe)Cl |
| 218 | CH | CH | S | CCl | CCl | 1,2-c-Pr | SCH$_2$(1,1-c-Pr)CH$_2$CO$_2$H | (CH$_2$)$_2$(1,2-phe)C(CH$_3$)$_2$OH |
| 219 | CH | CH | S | CCl | CCl | CH=CH | SCH$_2$(1,1-c-Pr)CH$_2$CO$_2$H | (CH$_2$)$_2$S(1,4-phe)F. |

6. A compound of claim 1 of the formula:

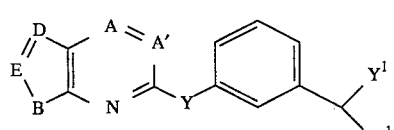

wherein A and A' are each —CH—; B is S; D is N; E is CCH$_3$; Y is —CH=CH—; Y¹ is SCH$_2$(1,1-c-Pr)CH$_2$CO$_2$H; and W¹is (CH$_2$)$_2$ (1,2-Phe)C(CH$_3$)$_2$OH.

7. A compound of claim 1 which is 1-(((1(R)-(3-(2 ( 2,3-dichlorothieno[3,2-b]pyridin-5-yl)-(E)-ethenyl) phenyl)-3-(2-(1 -hydroxy-1-methylethyl)phenyl)propyl)thio)methyl)cyclopropaneacetic acid, or a pharmaceutically acceptable salt thereof.

8. A compound of claim 7 which is sodium 1-(((1 (R)-(3-(2-(2,3-dichlorothieno[3,2-b ]pyridin-5-yl)-(E)-ethenyl)phenyl)-3-(2 -1-hydroxy-1-methylethyl)phenyl)propyl)thio)methyl)cyclopropaneacetate.

9. A pharmaceutical composition comprising a therapeutically effective amount of a compound of claim 1 and a pharmaceutically acceptable carrier.

10. The pharmaceutical composition of claim 9 additionally comprising an effective amount of a second active ingredient selected from the group consisting of non-steroidal anti-inflammatory drugs; peripheral analgesic agents; cycloxygenase inhibitors; leukotriene antagonists; leukotriene biosynthesis inhibitors; H$_1$- or H$_2$-receptor antagonists; antihistaminic agents; prostaglandin antagonists; and ACE antagonists.

11. A pharmaceutical composition of claim 10, wherein the second active ingredient is a non-steroidal anti-inflammatory drug.

12. A pharmaceutical composition of claim 11, wherein the weight ratio of said compound of claim 1 to said second active ingredient ranges from about 1000:1 to 1:1000.

13. A method of preventing the action of leukotrienes in a mammal which comprises administering to said mammal an effective amount of a compound of claim 1.

14. The method of claim 13 wherein the mammal is man.

15. A method of treating asthma in a mammal comprising administering to a mammal in need of such treatment a therapeutically effective amount of a compound of claim 1.

16. The method of claim 15 wherein the mammal is man.

17. A method of treating inflammatory diseases of the eye in mammal which comprises administering to a mammal in need of such treatment a therapeutically effective amount of a compound of claim 1.

* * * * *